United States Patent [19]

Eggler et al.

[11] Patent Number: 4,473,704

[45] Date of Patent: Sep. 25, 1984

[54] SUBSTITUTED DODECAHYDROTRIPHENYLENES, DECAHYDRO-1H-CYCLOPENTA[1]-PHENANTHRENES, DECAHYDRO-1H-PYRIDO[1,2-F]PHENAN-THRIDINES AND DECAHYDROPYRROLO[1,2-F]PHENAN-THRIDINES AS CNS AGENTS

[75] Inventors: James F. Eggler, Stonington; Michael R. Johnson, Gales Ferry; Lawrence S. Melvin, Jr., Ledyard, all of Conn.

[73] Assignee: Pfizer Inc., New York, N.Y.

[21] Appl. No.: 358,765

[22] Filed: Mar. 16, 1982

[51] Int. Cl.³ .................................... C07C 69/035
[52] U.S. Cl. .................................. 560/139; 544/125; 544/154; 544/361; 544/380; 546/71; 546/195; 546/200; 546/272; 546/285; 548/518; 548/528; 560/108; 564/97; 564/222; 568/714; 568/732
[58] Field of Search ............... 568/732, 714; 560/139, 560/108; 564/97, 222; 544/154, 380; 546/195, 285; 548/528

[56] References Cited

U.S. PATENT DOCUMENTS

| | | | |
|---|---|---|---|
| 4,087,545 | 5/1978 | Archer et al. | 424/283 |
| 4,152,450 | 5/1979 | Day et al. | 424/283 |
| 4,188,495 | 2/1980 | Althuis et al. | 568/633 |
| 4,228,169 | 10/1980 | Johnson et al. | 424/258 |
| 4,260,764 | 4/1981 | Johnson | 546/153 |
| 4,309,545 | 1/1982 | Johnson | 546/108 |

*Primary Examiner*—Paul M. Coughlan, Jr.
*Attorney, Agent, or Firm*—Charles J. Knuth; R. K. Blackwood; Mark Dryer

[57] ABSTRACT

1,2,3,4,4a,4b,5,6,7,8,8a,12b-Dodecahydro-7-(oxo, hydroxy or amino)-9-hydroxy-11-(alkyl, alkoxy or alkoxyalkyl)triphenylenes, 2,3,3a,3b,4,5,6,7,7a,11b-decahydro-6-(oxo, hydroxy or amino)-8-hydroxy-10-(alkyl, alkoxy or alkoxyalkyl)-1H-cyclopenta[1]phenanthrenes, 2,3,4,4a,4b,5,6,7,8,8a-decahydro-7-(oxo, hydroxy or amino)-9-hydroxy-11-(alkyl, alkoxy, alkoxyalkyl, aralkyl, aralkoxy, aryloxyalkyl or aralkoxyalkyl)-1H-pyrido[1,2-f]phenanthridines, and 1,2,3,3a,3b,4,5,6,7,7a-decahydro-6-(oxo, hydroxy or amino)-8-hydroxy-10-(alkyl, alkoxy or alkoxyalkyl)pyrrolo[1,2-f]phenanthridines and derivatives are valuable as central nervous system active agents or as intermediates to compounds having such activity.

9 Claims, No Drawings

SUBSTITUTED DODECAHYDROTRIPHENYLENES, DECAHYDRO-1H-CYCLOPENTA[1]PHENANTHRENES, DECAHYDRO-1H-PYRIDO[1,2-f]PHENANTHRIDINES AND DECAHYDROPYRROLO[1,2-f]PHENANTHRIDINES AS CNS AGENTS

BACKGROUND OF THE INVENTION

This invention relates to novel compounds which are substituted dodecahydrotriphenylenes, decahydro-1H-cyclopenta[1]phenanthrenes, decahydro-1H-pyrido[1,2-f]phenanthridines and decahydropyrrolo[1,2-f]phenanthridines and which are useful in mammals, including man, as CNS agents, especially as analgesics, tranquilizers, and antiemetics, as antidiarreals, as antitussives, as diuretics and as agents for the treatment of glaucoma; and as intermediates therefor.

Despite the current availability of a number of analgesic agents, the search for new and improved agents continues, thus pointing to the lack of an agent useful for the control of broad levels of pain and accompanied by a minimum of side-effects. The most commonly used agent, aspirin, is of no practical value for the control of severe pain and is known to exhibit various undesirable side-effects. Other, more potent analgesic agents such as d-propoxyphene, codeine, and morphine, possess addictive liability. The need for improved and potent analgesic agents is, therefore, evident.

There is also a continuing need for potent antiemetic agents having minimal side-effects, particularly in patients receiving cancer chemotherapy.

The analgesic properties of 9-nor-9beta-hydroxyhexahydrocannabinol and related compounds have been reported by Wilson and May, J. Med. Chem. 17, 475-476 (1974); 18, 700-703 (1975). The antiemetic activity of delta$^9$-tetrahydrocannabinol in patients undergoing cancer chemotherapy has been reported by Sallan et al. New England J. Med. 293, 795 (1975).

Various 5,6,6a,7,8,9,10,10a-octahydro-9-(oxo or hydroxy)-1-hydroxy-3-(alkyl, alkoxy, alkoxyalkyl, aralkyl, aralkoxy, aralkoxyalkyl, or aryloxyalkyl)phenanthridine derivatives have been reported to possess various medicinal properties particularly, analgesic activity, Johnson, U.S. Pat. No. 4,260,764, as well as antiemetic activity, Johnson and Milne, U.S. Pat. No. 4,228,169, 11/14/80.

Various 1,2,3,4,4a,9,10,10a-octahydro-3-(oxo or hydroxy)-5-hydroxy-7-(alkyl, alkoxy, alkoxyalkyl, aralkyl, aralkoxy, aralkoxyalkyl, or aryloxy)phenanthrenes are also reported to possess analgesic activity, Althuis et al., U.S. Pat. No. 4,188,495 (2/12/80).

Various 6a,7,8,9,10,10a-hexahydro-9-amino-1-hydroxy-3-alkyl-6H-benzo[c]chromene derivatives are reported to be useful as analgesics, antidepressants, antianxiety, and hypotensive agents, Day et al., U.S. Pat. No. 4,152,450 (5/1/79); while various 7,8,10,10a-tetrahydro-1-hydroxy-3-alkyl-6H, 6aH-benzo[c]chromen-9-one derivatives are reported as antiemetic drugs, Archer et al., U.S. Pat. No. 4,087,545 (5/2/78), and earlier as having antidepressant, analgesic and antianxiety properties, Archer, U.S. Pat. Nos. 3,953,603 (4/27/76), 3,944,673 (3/16/76) and 3,928,598 (12/23/75).

Johnson, U.S. Pat. No. 4,309,545 (1/5/82) discloses 5,6,6a,7,8,9,10,10a-octahydro-9-amino-1-hydroxy-3-(alkyl, alkoxy, alkoxyalkyl, aralkyl, aralkoxy, aralkoxyalkyl or aryloxyalkyl)phenanthridine derivatives as having CNS activity, particularly useful as analgesics and antiemetics.

Copending U.S. patent application, Ser. No. 358,569 filed concurrently herewith, discloses various 1,2,3,4,4a,9,10,10a-octahydro-9-(substituted)-8-hydroxy-6-(alkyl, alkoxy, alkoxyalkyl, aralkyl, aralkoxy, aralkoxyalkyl or aryloxyalkyl)phenanthrene, 2,3,3a,4,5,9b-hexahydro-5-(substituted)-6-hydroxy-8-(alkyl, alkoxy, alkoxyalkyl, aralkyl, aralkoxy, aralkoxyalkyl or aryloxyalkyl)cyclopenta[a]naphthalene, 2,3,4,4a,5,6-hexahydro-6-(substituted)-7-hydroxy-9-(alkyl, alkoxy, alkoxyalkyl, aralkyl, aralkoxy, aralkoxyalkyl or aryloxyalkyl)-1H-pyrido[1,2-a]quinoline and 1,2,3,3a,4,5-hexahydro-5-(substituted)-6-hydroxy-8-(alkyl, alkoxy, alkoxyalkyl, aralkyl, aralkoxy, aralkoxyalkyl or aryloxyalkyl)pyrrolo[1,2-a]quinoline derivatives having similar CNS activity.

The nomenclature employed herein is based on Rigaudy and Klesney, I.U.P.A.C. Nomenclature of Organic Chemistry - 1979 Edition, Permangon Press, N.Y., including the use of R and S to designate absolute stereochemistry and R* and S* to designate relative stereochemistry. Formulae showing dotted and heavy bonds are generally intended to specify relative stereochemistry, unless otherwise specified in the text.

SUMMARY OF THE INVENTION

Compounds of the present invention having pharmaceutical utility are of the formulae

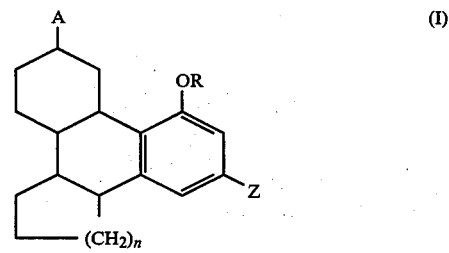

(I)

and

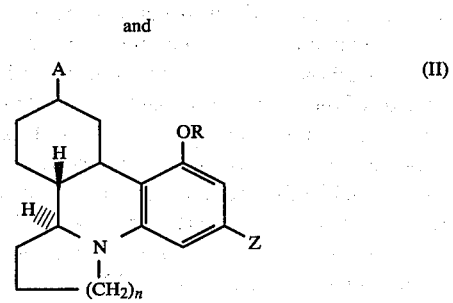

(II)

wherein n is 1 or 2;

A is OH, $(C_1-C_5)$alkanoyloxy, $(C_1-C_5)$alkanoylamino or $(C_1-C_4)$alkanesulfonamido;

R is H, benzoyl, $(C_1-C_5)$alkanoyl or —CO(CH$_2$)$_m$Y, wherein m is 1, 2, 3 or 4, Y is —COOH, or —NR'R", R' and R" when taken separately are each independently H or $(C_1-C_4)$alkyl, and R' and R" when taken together with the nitrogen to which they are attached are piperidino, pyrrolo, pyrrolidino, morpholino or N—[$(C_1-C_4)$alkyl]piperazino; and Z is $(C_5-C_{13})$alkyl, $(C_5-C_{13})$alkoxy, $(C_5-C_{13})$alkoxyalkyl, $(C_8-C_{13})$pyridylalkyl, $(C_8-C_{13})$pyridylalkoxy, $(C_8-C_{13})$pyridyloxyalkyl, $(C_8-C_{13})$pyridylalkoxyalkyl, $(C_9-C_{14})$phenylalkyl, $(C_9-C_{14})$phenylalkoxy, $(C_9-C_{14})$phenoxyalkyl or $(C_9-C_{14})$phenylalkoxyalkyl, wherein said phenyl groups are optionally substituted with a chloro or a fluoro.

Here and elsewhere in this application, the bracketed ranges of carbon atoms are intended to encompass the range of carbon atoms of the entire group which follows. For example $(C_1-C_5)$alkanoyl encompasses HCO— to $C_4H_9CO$—, while $(C_9-C_{14})$phenylalkyl encompasses $(C_6H_5)C_3H_6$— to $(C_6H_5)C_8H_{16}$—. Compounds of the present invention having particular utility as intermediates, in addition to pharmaceutical utility, are of the formulae

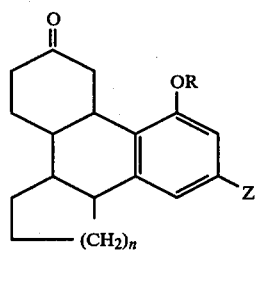

(III)

and

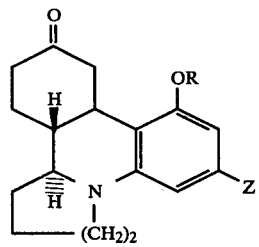

(IV)

wherein n, R and Z are as defined above.

Also encompassed by the present invention are pharmaceutically-acceptable acid addition salts of compounds of the formulae (II) and (IV), and of the formulae (I) and (III) wherein R is $—CO(CH_2)_mY$ and Y is $—NR'R''$, as well as the pharmaceutically-acceptable cationic salts of compounds of the formulae (I) to (IV) wherein R is $—CO(CH_2)Y$ and Y is —COOH.

The numbering and ring systems for the compounds of the present invention are as follows:

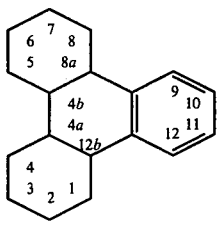

triphenylenes

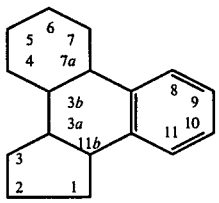

1H—cyclopenta[1]-
phenanthrenes

-continued

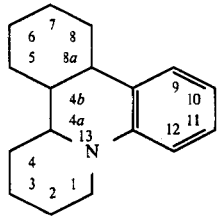

1H—pyrido[1,2-f]-
phenanthridines

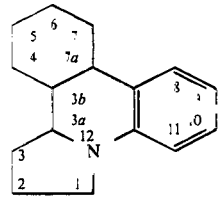

pyrrolo[1,2-f]-
phenanthridines

Thus the compounds of the formulae (I) to (IV) are named as follows:

(I), n=1: 2,3,3a,3b,4,5,6,7,7a,11b-decahydro-6-(A-substituent)-8-(OR-substituent)-10-(Z-substituent)-1H-cyclopenta[1]phenanthrene;

(III), n=1: 3,3a,3b,4,5,7,7a,11b-octahydro-8-(OR-substituent)-10-(Z-substituent)-1H,2H-cyclopenta[1]phenanthren-6-one;

(I), n=2: 1,2,3,4,4a,4b,5,6,7,8,8a,12b-dodecahydro-7-(A-substituent)-9-(OR-substituent)-11-(Z-substituent)triphenylene;

(III), n=2: 2,3,4,4a,4b,5,6,8,8a,12b-decahydro-9-(OR-substituent)-11-(Z-substituent)-1H-triphenylen-7-one;

(II), n=1: 1,2,3,3aS*,3bR*,4,5,6,7,7a-decahydro-6-(A-substituent)-8-(OR-substituent)-10-(Z-substituent)pyrrolo[1,2-f]phenanthridine;

(IV), n=1: 2,3,3aS*,3bR*,4,5,7,7a-octahydro-8-(OR-substituent)-10-(Z-substituent)-1H-pyrrolo[1,2-f]phenanthridin-6-one;

(II), n=2: 2,3,4,4aS*,4bR*,5,6,7,8,8a-decahydro-7-(A-substituent)-9-(OR-substituent)-11-(Z-substituent)-1H-pyrido[1,2-f]phenanthridine; and (IV), n=2: 3,4,4aS*,4bR*,5,6,8,8a-octahydro-9-(OR-substituent)-11-(Z-substituent)-1H, 2H-pyrido[1,2-f]phenanthridin-7-one.

Compounds of the present invention useful as intermediates are of the formulae

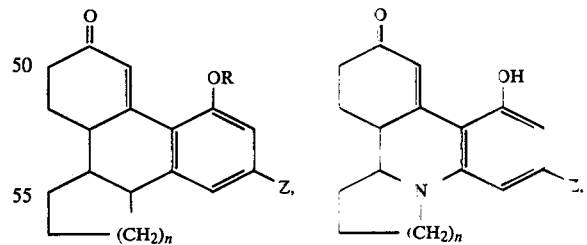

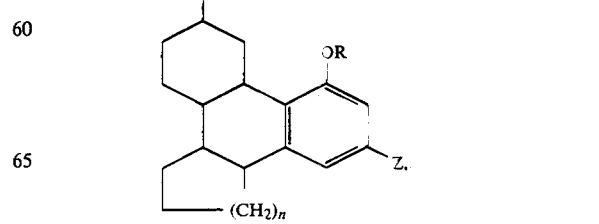

V)

(VI)
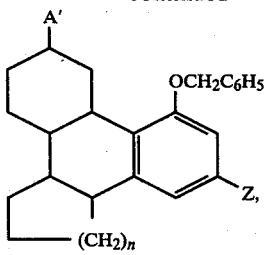

(VII)
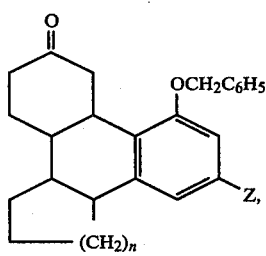

(VIII)
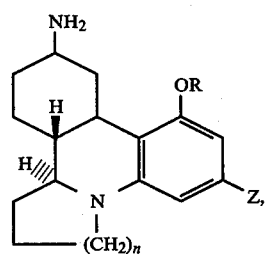

(IX)
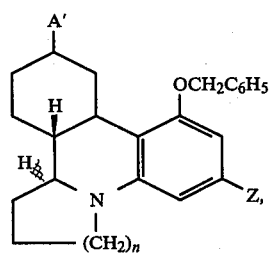

(X)
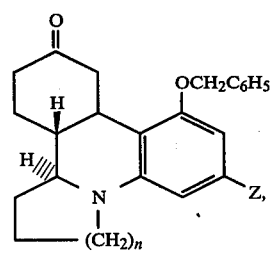

and (XI)
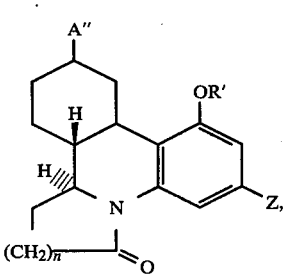

wherein
n, R and Z are as defined above;

A' is OH, $(C_1-C_5)$alkanoyloxy, $NH_2$, $(C_1-C_5)$alkanoylamino or $(C_1-C_4)$alkanesulfonamido;
A" is OH or $NH_2$; and
R' is H, benzoyl or $(C_1-C_5)$alkanoyl.

The compounds (V) to (XI) are named by analogy to the compounds (I) to (IV). For example, the compounds of the formula (XI) when n=1, are named as follows:
3,3aS*,3bR*,4,5,6,7,7a-hexahydro-6-(A"-substituent)-8-(OR'-substituent)-10-(Z-substituent)-2H-pyrrolo[1,2-f]phenanthridin-1-one.

The preferred relative stereochemistry for the compounds (I), (III), (V), (VI) and (VII) is 3aS*,3bS*-/4aS*,4bS*, i.e. 3a,3b/4a,4b trans. Within these groups, the more preferred stereochemistry is 3aS*,11bR*-/4aS*,12bR*, i.e. 3a,11b/4a,12b also trans. Within the latter group, even more preferred are compounds having 3bS*,7aR*/4bS*,8aR*, i.e. 3b,7a/4b,8a also trans. Finally, in those compounds of the last named group having a substituent A or A', said substituent is preferably equatorial (6R*/7R*), i.e. the group A or A' on the opposite side of the molecule from the 7a/8a-hydrogen. In the corresponding compounds which are optically active, the same considerations of relative stereochemistry apply, with the most highly preferred compounds having the 7aR/8aR configuration, e.g., (IX)
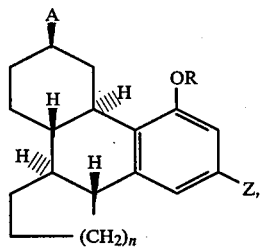

named (when n=2) as follows:
1,2,3,4,4aS,4bS,5,6,7R,8,8aR,12bR-dodecahydro-7-(A-substituent)-9-(OR-substituent)-11-(Z-substituent)-triphenylene.

The compounds of the formulae (II), (IV), (VIII), (IX), (X) and (XI) have relative stereochemistry specified as 3aS*,3bR*/4aS*,4bR*, i.e. 3a,3b/4a,4b-trans. Further preferred relative stereochemistry in all of these cases is 3bR*,7aR*/4bR*,8aR*, i.e. 3b,7a/4b,8a-trans. Within these groups of compounds which have a substituent A, A' or A", said substituent is preferably equatorial (6R*/7R*), i.e. on the opposite side of the molecule from the 7a/8a-hydrogen. In the corresponding compounds, which are optically active, the same considerations of relative stereochemistry apply, with the most highly preferred compounds having the 7aR/8aR configuration, e.g., (XIII)
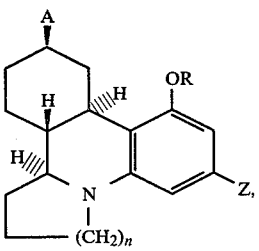

named (when n=2) as follows:

2,3,4,4aS,4bR,5,6,7R,8,8aR-decahydro-7-(A-substituent)-9-(OR-substituent)-11-(Z-substituent)-1H-pyrido[1,2-f]phenanthridine.

In all cases, the preferred value of Z is 5-phenyl-2-pentyloxy; 5-phenyl-2R-pentyloxy, i.e.,

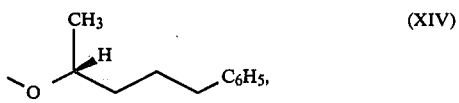

is most preferred. The preferred value of R is acetyl and that of A is hydroxy. The preferred value of n is 2.

Also encompassed by the present invention are oral and parenteral formulations of compounds of the formulae (I), (II), (III) and (IV), as well as methods of alleviating pain (analgesia), and preventing emesis in mammals, including man.

DETAILED DESCRIPTION OF THE INVENTION

Compounds of the formulae (I) and (II), wherein A is OH, are prepared by sodium borohydride reduction of corresponding compounds of the formulae (III) and (IV). It is preferred that the phenolic groups of the latter compounds be protected by an acyl group, i.e., R other than hydrogen. The reduction is generally carried out in a lower alkanol (e.g., methanol, ethanol, isopropanol) within the temperature range $-15°$ to $35°$ C., preferably $-5°$ to $15°$ C. when ethanol is the solvent, preferably below $-35°$ C. when methanol is the solvent, with at least one equivalent of sodium borohydride. Reaction time is not critical. For example at a 1% substrate concentration in ethanol, with a substantial excess of hydride, the reaction is essentially complete within 10 minutes at $0°$ C. By the same method, precursor compounds of the formulae (VII) and (X) are converted to the corresponding compounds of the formulae (VI) and (IX) wherein A' is hydroxy, and precursor compounds of the formula

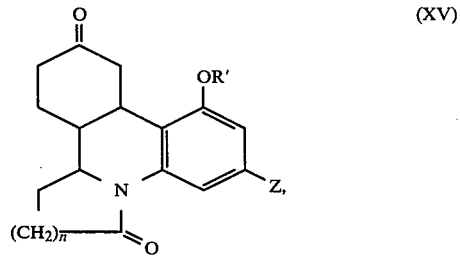

wherein n, R' and Z are as defined above, are reduced to compounds of the formula (XI). Alternatively the various ketone reductions of this paragraph are carried out by hydrogenation over a noble metal catalyst. Pressure is not critical, although, from the viewpoint of equipment cost, pressures from ambient to about 7 kg./cm.² are preferred. Temperature is likewise not critical, the range 0°–50° C. is preferred, ambient temperature being most preferred from the viewpoint of cost. Solvent is not critical; any solvent which does not react with reactants, products, or reagents to significantly reduce yield (i.e. reaction inert) being well suited; lower alkanols are particularly well suited for this purpose. The noble metal catalyst can be of the unsupported type (e.g. Pt black, PtO₂, PdCl₂, RhCl₃) or of the supported type (e.g. Rh/C, Pd/BaSO₄). The most highly preferred catalyst is Pd/C usually 1–10% Pd by weight. The hydrogenation is carried out until substantially one equivalent is taken up. When the substrate contains a benzyl group [compounds of the formulae (VII) and (X)], this method is not preferred if retention of the benzyl group is desired. However, by permitting the latter compounds to take up two equivalents of hydrogen under these conditions the alcoholic compounds of the formulae (I) and (II), wherein A is hydroxy and R is H, are formed directly, representing an alternative synthesis of these compounds. By either the hydride or catalytic hydrogenation methods of this paragraph, both isomeric alcohols are produced, but the equatorial alcohol predominates, especially under the preferred hydrogenation conditions.

The ketones of the formulae (III), (IV), (VII), (X) and (XV) are derived from the corresponding alpha,beta-unsaturated ketones, of the partial formula

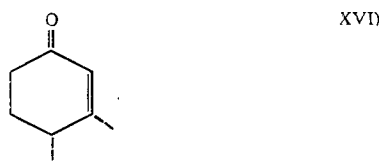

by Li/NH₃ reduction. If desired, the reduction is carried out in the presence of a reaction-inert diluent (as defined above) such as an ether, conveniently tetrahydrofuran. A slight excess of lithium metal is employed, determined by adding lithium portionwise until a blue color persists for several minutes. The reaction is carried out cold, e.g. $-20°$ to $-50°$ C., preferably at or below the boiling point of the reaction mixture so as to avoid the need for a pressure vessel. If the ketone derived by the present process has a free phenolic group, it can, if desired be acylated by any one of a number of methods standard to the organic chemist's art. Conveniently, at least one equivalent of an acylating agent (e.g. acetyl chloride, propionic anhydride, acetoformic acid reagent, benzoyl chloride, 3-dimethylaminopropionyl chloride hydrochloride, succinic anhydride, the mixed anhydride formed between benzoic acid and ethyl chloroformate, propyl chloroformate, etc.) is reacted with the phenolic ketone, usually in the presence of at least one equivalent of a tertiary organic amine (e.g. triethylamine, pyridine, 4-dimethylaminopyridine), and preferably an excess of said amine, in a reaction inert solvent (e.g. a chlorohydrocarbon such as methylene chloride) or in an excess of the amine (e.g. pyridine). When it is desired that the final product contain a phenolic acyl group and no alcoholic acyl group, it is preferred that the phenolic acyl group (if not already present) be introduced into compounds of the formulae (III) or (IV) at this stage of the overall process.

Alternatively, compounds of the formulae (I), (II) and (XI), wherein A or A" is hydroxyl, are prepared by hydrogenation of the corresponding compounds of the partial formula (XVI), accomplishing the reduction of the double bond, the ketone group and (if present) the benzyl group in a single step. The conditions are as specified above for ketone hydrogenation, except that substantially two equivalents of hydrogen are consumed (three equivalents if a benzyl group is also present and reduced). Little of the 3b,7a/4b,8a-cis or 6/7-axial alcohol compounds are formed under these conditions, particularly when the preferred catalyst (Pd/C) is employed.

In a further synthetic method, phenols of the formulae (I) and (II), wherein R is hydrogen, are obtained by the hydrogenolysis of the corresponding benzyl ethers of the formulae (VI) and (IX).

In the specific case of the alcohols of the formula (II), wherein A is hydroxy and R is H, such compounds are also obtained by relatively vigorous hydride reduction of the corresponding compounds of the formula (XI), wherein A″ is hydroxy. If acyl groups are present on either the alcohol or phenol groups, they will be reductively removed under the conditions employed for the reduction of the lactam. Suitable conditions are excess lithium aluminum hydride at an elevated temperature (45°–85° C.) in a higher boiling ether such as tetrahydrofuran or dimethoxyethane. When the reflux temperature of the mixture is exceeded, a pressure vessel is employed. Refluxing tetrahydrofuran represents conditions well suited for this reaction.

If desired, alcohols of the formulae (I), (II), (VI) and (IX), wherein A or A′ is hydroxy, are acylated according to conditions detailed above, yielding the corresponding compounds of the formulae (I), (II), (VI) and (IX), wherein A or A′ is ($C_1$–$C_5$)alkanoyloxy. When the alcohols also contain a free phenolic group, the phenolic group is also acylated under these conditions, necessitating the use of at least two equivalents each of acylating agent and base, and yielding the bis-($C_1$–$C_5$)alkanoates. The phenolic acyl group, if desired, is readily removed from these compounds by solvolysis in methanol in the presence of anhydrous potassium carbonate at reduced temperature (−15° to 15° C.), yielding compounds of the formula (I) or (II) wherein A is ($C_1$–$C_5$)alkanoyloxy and R is hydrogen. The same compounds are alternatively obtained by hydrogenolysis of compounds of the formulae (VI) or (IX) wherein A′ is ($C_1$–$C_5$)alkanoyloxy, using conditions as described above.

If desired, compounds of the formulae (I) and (II), wherein A is ($C_1$–$C_5$)alkanoyloxy and R is hydrogen, are further acylated to produce the corresponding compounds of the formula (I) and (II) wherein A is ($C_1$–$C_5$)alkanoyloxy and R is other than hydrogen, using a method of acylation as detailed above. This route has particular value in the preparation of mixed esters.

Compounds of the formulae (I) and (II) wherein A is ($C_1$–$C_5$)alkanoylamino or ($C_1$–$C_4$)alkanesulfonamido are prepared by acylation of the corresponding compounds of the formulae (V) and (VIII). Conditions as described above for the acylation of hydroxy compounds can be used for this purpose. When R is H in the substrate (V) or (VIII), the phenolic hydroxyl group is also acylated. If desired, the phenolic acyl group is removed by selective hydrolysis as described above for bis-esters. Alternatively, compounds of the formulae (I) and (II) wherein A is amino and R is hydrogen are selectively acylated on the amine function by using no more than one equivalent of the acylating agent (e.g. isobutyryl chloride, acetic anhydride, ethanesulfonyl chloride) and no extraneous base. Compounds of formulae (VI) and (IX) wherein A′ is amino are likewise acylated to the corresponding compounds of the formulae (VI) and (IX) wherein A′ is ($C_1$–$C_5$)alkanoylamino or ($C_1$–$C_4$)alkanesulfonamido according to the various methods of this paragraph. Hydrogenolysis of the latter compounds, under the conditions and preferred conditions detailed above, with uptake of substantially one equivalent of hydrogen, provides an alternative route to compounds of the formulae (I) and (II) wherein A is ($C_1$–$C_5$)alkanoylamino or ($C_1$–$C_4$)alkanesulfonamido and R is H.

If desired, the last-named compounds are acylated on the phenolic hydroxyl group according to methods detailed above to yield corresponding compounds of the formulae (I) and (II) wherein A is ($C_1$–$C_5$)alkanoylamino or ($C_1$–$C_4$)alkanesulfonamido and R is other than H.

A number of methods are available for the synthesis of the precursor amines of the formulae (V), (VIII), and (XI) wherein A″ is amino. One route, particularly preferred for a compound already having a phenolic acyl group in place or when the desired compound is an axial amine, is the catalytic hydrogenation of the corresponding oxime of the partial formula

under the same conditions and preferred conditions of hydrogenation as those detailed above, in this case with the uptake of essentially two equivalents of hydrogen. The required oximes are derived from the corresponding ketones of the partial formula (XVI) using conditions well known in the chemical art. For example reaction of the ketone with hydroxylamine hydrochloride is carried out in an excess of a tertiary amine such as pyridine, optionally in the presence of a reaction inert solvent, such as a lower alkanol. Temperature is not critical (e.g. 25°–50° C.), ambient temperature being well suited for the purpose.

Alternatively, the amines of the formulae (V), (VIII) and (XI) wherein A″ is amino and R′ is hydrogen are prepared by hydride reduction of the corresponding methoxyimines of the partial formula

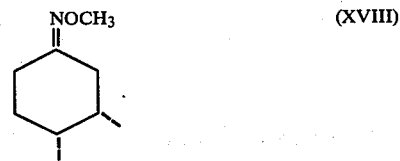

Relatively vigorous conditions are required for this hydride reduction, such that if an acyl group is present on the phenolic hydroxylic group, said group will usually also be reductively removed. A well suited method is to react at least an equivalent sodium borohydride with the methoxyimino compound in tetrahydrofuran - initially at reduced temperature, but ultimately for up to several hours at reflux temperature. The methoxyimine is prepared according to methods detailed above for oximes, substituting methoxyamine for hydroxylamine.

Amines of the formulae (V) and (VIII) wherein R is hydrogen, as well as amides of the formulae (I) and (II) wherein A is ($C_1$–$C_5$)alkanoyloxy or ($C_1$–$C_4$)alkanesulfonamido and R is hydrogen are also prepared by hydrogenolysis of the corresponding benzyl ethers of the formulae (VII) and (IX) wherein A′ is amino, ($C_1$–$C_5$)alkanoyloxy or ($C_1$–$C_4$)alkanesulfonamido according to methods detailed above for the debenzylation of related alcohols and esters. The precursors are derived from benzyl ketones via oxime or methoxyimine formation, reduction and ayclation as detailed above.

Amines of the formula (VIII) wherein R is hydrogen are also obtained by the lithium aluminum hydride reduction of either the corresponding amines of the formula (XI) or of the corresponding methoxyimine precursors of the partial formula (XVIII), using at least the appropriate number of equivalents of lithium aluminum hydride and otherwise under conditions as detailed above for the reduction of hydroxy lactams. The required methoxyimine is derived by methods detailed above from the corresponding ketone of the formula (XV).

In all of the above cases which involve the reduction of an oxime or methoxyimine, the dominant product is the equatorial amine.

The following synthetic sequence is essentially common to the preparation of all of the tetracyclic alpha,-beta-unsaturated ketones of the partial formula (XVI) from the corresponding tricyclic ketones:

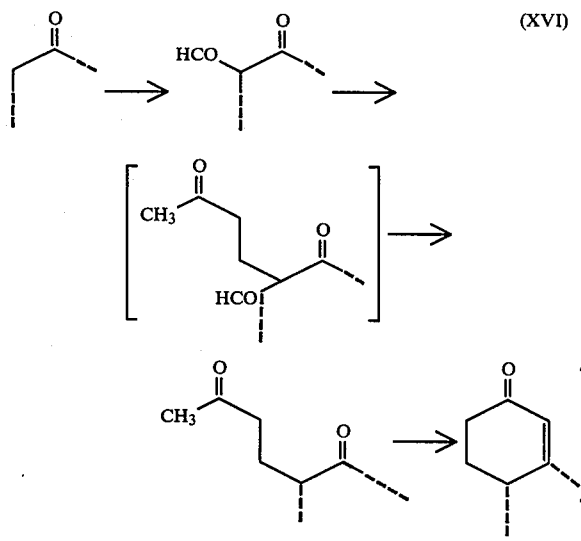
(XVI)

Typical conditions used for these transformations are detailed in the experimental section below. Typical tricyclic ketones used in this sequence are:

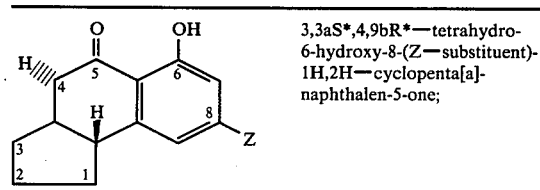

3,3aS*,4,9bR*—tetrahydro-6-hydroxy-8-(Z—substituent)-1H,2H—cyclopenta[a]naphthalen-5-one;

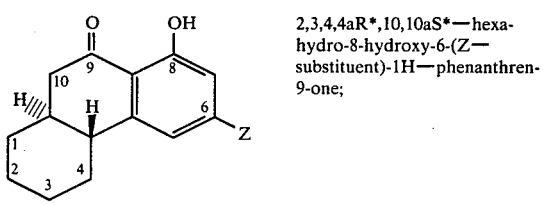

2,3,4,4aR*,10,10aS*—hexahydro-8-hydroxy-6-(Z—substituent)-1H—phenanthren-9-one;

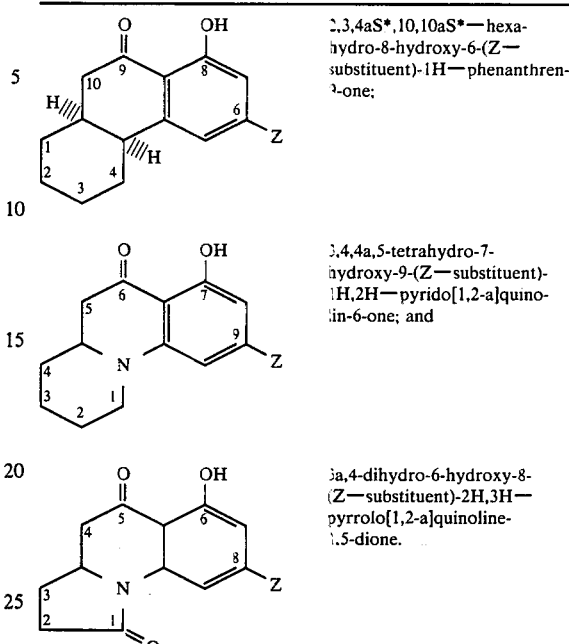

2,3,4aS*,10,10aS*—hexahydro-8-hydroxy-6-(Z—substituent)-1H—phenanthren-9-one;

3,4,4a,5-tetrahydro-7-hydroxy-9-(Z—substituent)-1H,2H—pyrido[1,2-a]quinolin-6-one; and 3a,4-dihydro-6-hydroxy-8-(Z—substituent)-2H,3H—pyrrolo[1,2-a]quinoline-1,5-dione.

In the case of tricyclic nitrogen and 3a,9b/4a,10a-trans carbocyclic analogs, this reaction sequence results in tetracyclic compounds wherein the 3a,3b/4a,4b-hydrogens are trans, i.e., the 3b,4/4b,5-bond is pseudo-equatorial to the center ring. However, with 3a,9b-/4a,10 a-cis tricyclic analogs, there is no marked preference, and significant quantities of both the 3a,3b/4a,4b-cis and trans compounds are formed in this reaction sequence. When it is desired that the phenolic hydroxy group be substituted by benzyl or an acyl group (R as defined above, other than hydrogen), it is preferred that this group be introduced at the end of the sequence by methods described above and in specific examples hereinafter. When Z is other than alkoxy or aralkoxy, this group will generally be in place at the beginning of the sequence. When Z is alkoxy or aralkoxy, said group is generally formed from a phenolic group and an alkyl or aralkyl mesylate or halide, generally in the presence of at least one equivalent of base. This alkylation can be carried out at any stage of the reaction sequence under discussion, provided that it is carried out before any acylation or benzylation of the other phenolic group. It is preferred however, to have the complete group Z in place prior to entering this reaction sequence.

Depending on structure, various methods are available for preparation of the tricyclic ketones used as starting materials for the synthetic sequence of the preceding paragraph.

One sequence available for the preparation of numerous tricyclic carbon analogs employs as a first stage the heating of cyclohexanone or cyclopentanone with a suitable substituted phenyl Grignard in a high boiling, reaction inert solvent to produce a compound of the formula

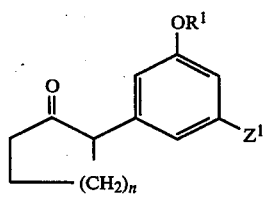

wherein n is as defined above, $R^1$ is methyl or benzyl and $Z^1$ is methoxy, benzyloxy, $(C_5-C_{13})$alkyl, $(C_5-C_{13})$alkoxyalkyl, $(C_9-C_{14})$phenylalkyl, or $(C_9-C_{14})$phenylalkoxyalkyl. Condensation with alkyl acetate, dehydration, and hydrolysis of intermediate ester produces unsaturated acids of the formulae

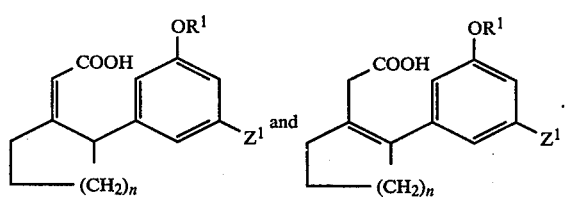

Equivalents such as malonate (decarboxylate to the acetate after hydrolysis) can be substituted for the alkyl acetate. Lithium in liquid ammonia reduction of the former yields the trans-form of the substituted acetic acid derivatives, while catalytic hydrogenation of the latter under conditions detailed above yields the cis-form of the acetic acid (with simultaneous debenzylation when $R^1$ is benzyl). Finally, cyclization, debenzylation or O-demethylation and alkylation when Z is a phenolic ether derivative, yields tricyclic ketones of the respective formulae

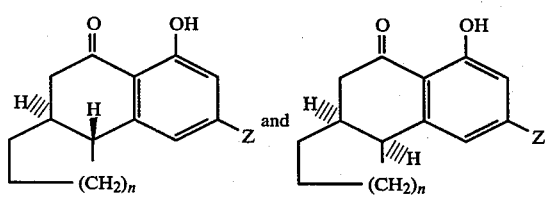

wherein n and Z are as hereinbefore defined.

Alternatively, suitable substituted aromatic aldehydes are condensed with nitromethane to yield trans-1-(disubstituted phenyl)-2-nitroethylenes of the formula

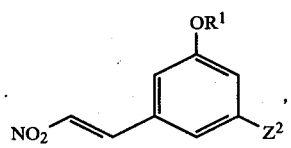

wherein $R^1$ is as defined above and $Z^2$ is methoxy, benzyloxy or Z is as defined above. Condensation of the latter with butadiene under Diehls-Alder conditions yields the corresponding 4-(substituted phenyl)-5-nitrocyclohexene. The Nef reaction converts the nitro compound to the unsaturated cyclohexanone derivative, viz, 6-(disubstituted phenyl)-3-cyclohexen-1-one which is hydrogenated according to methods detailed above (with simultaneous removal of benzyl, if present); demethylated if methyl ether is present (with simultaneous dealkylation if $Z^2$ is an alkoxy derivative); and alkylated if Z is an alkoxy derivative to yield a ketone of the formula

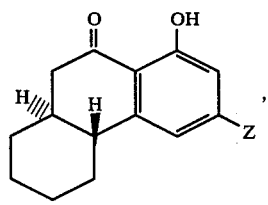

wherein Z is as defined above. It will be noted that inversion occurs in such alkylation reactions, e.g., 5-phenyl-2S-pentyl mesylate yields Z as 5-phenyl-2R-pentyloxy.

Corresponding tricyclic nitrogen analogs are conveniently prepared from 3,omega-dihalo acids and disubstituted anilines, e.g.,

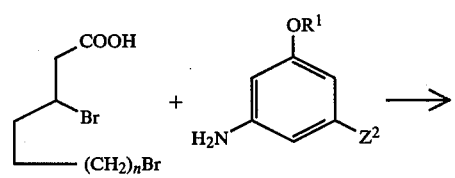

wherein n, $R^1$ and $Z^2$ are as defined above, followed by cyclization, debenzylation or demethylation (accompanied by dealkylation when $Z^2$ is an alkoxy derivative) and alkylation when Z is an alkoxy derivative to yield pyrrolo/pyrido[1,2-a] quinolinones of the formula

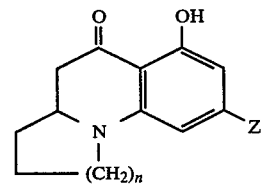

The corresponding tricyclic lactams are prepared from the same anilines by either initial alkylation-cyclizaiton with 3-halo diesters or reductive alkylation-cyclization with 3-keto diesters to yield intermediate esters which are hydrolyzed to acids of the formula

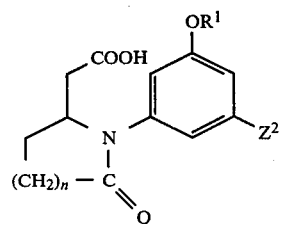

wherein n, $R^1$ and $Z^2$ are as defined above, followed by the further steps of the preceding paragraph to yield pyrrolo/pyrido[1,2-a] quinoline diones of the formula

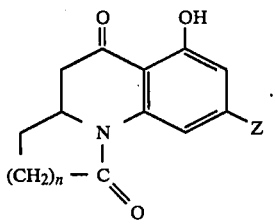

Many of the anilines, aromatic halides or aromatic aldehydes required as starting materials for the present syntheses are available commercially or their syntheses are reported in the literature. When not otherwise available, the anilines required for the present syntheses are prepared by methods previously set forth by Johnson, U.S. Pat. No. 4,260,764. The latter are converted to the corresponding aromatic bromides and chlorides according to procedures set forth by Bigelow, Organic Syntheses I, pp. 135–137 (1941) and then reacted with magnesium to provide the required Grignard reagents. While a variety of methods are available for the synthesis of the required aldehydes they are also broadly available from the anilines of Johnson. The anilines are converted to the corresponding nitriles by the method of Clarke and Read, Organic Syntheses I, pp. 514–516 (1941). The nitriles are subjected to the Stephen reduction to yield the aldehyde directly. Alternatively, the nitriles are hydrolyzed to acid, then converted to acid chloride and hydrogenated under Rosemund conditions. Acid chlorides can also be converted to the thiol ester and desulfurized to aldehydes according to Wolfram et al., J. Am. Chem. Soc. 68, pp. 1455–1546. Alternatively, aldehydes are obtained from the corresponding benzyl aldehydes by oxidation in dimethylsulfoxide according to Kornblum et al., J. Am. Chem. Soc. 81, pp. 4113–4114. The benzyl bromides are prepared according to methods set forth in Althuis et al., U.S. Pat. No. 4,188,495. Aldehydes are also available by reaction of aromatic Grignard reagents with ethyl orthoformate.

When Z is ($C_5$–$C_{13}$)alkoxy, ($C_8$–$C_{13}$)pyridylalkoxy, or ($C_9$–$C_{14}$)phenylalkoxy (the phenyl group optionally substituted with a chloro or fluoro), the required halide or mesylate, if not available commercially, is readily obtained from the corresponding alcohol using conditions standard in the chemical art. The alcohols in turn are available commercially or by literature methods. For example primary alcohols are available by hydride reduction of aldehydes, acids or esters, while secondary alcohols are available by hydride reduction of ketones. All varieties of alcohols are available by the hydration of olefins, or by the reaction of epoxides with Grignard reagents. Furthermore, many halides suitable for the introduction of the sidechain are available by direct halogenation of olefins or addition of hydrogen halides to olefins.

When the optically active variant of one of the compounds of the present invention is desired, resolution is accomplished by formation and separation of diastereomeric salts derived from an optically active amine/acid with an acidic/basic intermediate or end product according to methods well known in the chemical art. Alternatively, alcohol intermediates are resolved by formation of diasteromeric esters, e.g. optically active amine salts of hemiphthalate esters or are formed directly by use of optically active reagents. It is preferred, however, to carry out the resolution at an early stage in the process in order to avoid unnecessary processing of material which is not desired.

The pharmaceutically acceptable acid addition salts of the present invention are readily prepared by contacting the free base with the appropriate mineral or organic acid in either aqueous solution or in a suitable organic solvent. The salt can then be obtained by precipitation or by evaporation of the solvent. The pharmaceutically acceptable acid addition salts of this invention include, but are not limited to, those formed with hydrochloric, hydrobromic, nitric, phosphoric, sulfuric, benzenesulfonic, citric, laurylsulfonic, fumaric, oxalic, maleic, methanesulfonic, tartaric, p-toluenesulfonic, and succinic acid. With polybasic acids, the salt can include more than one mole of base per mole of acid. However, the acid addition salts which are mole for mole are preferred. If desired, these salts are isolated directly from reaction mixtures by suitable modification of the isolation procedure, without isolation of the intermediate free acid.

The pharmaceutically acceptable cationic salts of the compounds of the present invention are readily prepared by reacting the acid forms with an appropriate base, usually one equivalent, in a co-solvent. By the expression "pharmaceutically acceptable cationic salts" is intended salts such as the alkali metal salts, e.g., sodium and potassium; alkaline earth metal salts such as calcium and magnesium; aluminum salts; ammonium salts; and salts with organic bases, e.g., amines such as benzathine (N,N'-dibenzylethylenediamine), choline, diethanolamine, ethylenediamine, meglumine N-methylglucamine), benethamine (N-benzylphenethylamine), diethylamine, piperazine, and tromethamine (2-amino-2-hydroxymethyl-1,3-propanediol). Typical bases employed in the preparation of these cationic salts are sodium hydroxide, sodium methoxide, sodium ethoxide, sodium hydride, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of a different salt of the cation (e.g., sodium ethylhexanoate, magnesium oleate), employing a solvent in which the desired cationic salt precipitates, or can be otherwise isolated by concentration and/or addition of a non-solvent. If desired, these salts are isolated directly from reaction mixtures by suitable isolation procedures, without isolation of the intermediate free acid.

The analgesic properties of the compounds of this invention are determined by tests using thermal nociceptive stimuli, such as the mouse tail flick procedure, or chemical nociceptive stimuli, such as measuring the ability of a compound to suppress phenylbenzoquinone irritant-induced writhing in mice. These tests and others are described below.

Tests Using Thermal Nociceptive Stimuli (a) Mouse Hot Plate Analgesic Testing

The method used is modified after Woolfe and MacDonald, J. Pharmacol. Exp. Ther., 80, 300–307 (1944). A controlled heat stimulus is applied to the feet of mice on a ⅛" thick aluminum plate. A 250 watt reflector infrared heat lamp is placed under the bottom of the aluminum plate. A thermal regulator, connected to thermistors on the plate surface, programs the heat lamp to maintain a constant temperature of 57° C. Each mouse is dropped into a glass cylinder (6½" diameter) resting on the hot plate, and timing is begun when the animal's feet touch the plate. At 0.5 and 2 hours after treatment with the test compound the mouse is observed for the first "flicking" movements of one or both hind feet, or until 10 seconds elapse without such movements. Morphine has an $MPE_{50}=4-5.6$ mg./kg. (s.c.).

(b) Mouse Tail Flick Analgesic Testing

Tail flick testing in mice is modified after D'Amour and Smith, J. Pharmacol. Exp. Ther., 72, 74–79 (1941), using controlled high intensity heat applied to the tail. Each mouse is placed in a snug-fitting metal cycliner, with the tail protruding through one end. This cycliner is arranged so that the tail lies flat over a concealed heat lamp. At the onset of testing, an aluminum flag over the lamp is drawn back, allowing the light beam to pass through the slit and focus onto the end of the tail. A timer is simultaneously activated. The latency of a sudden flick of the tail is ascertained. Untreated mice usually react within 3–4 seconds after exposure to the lamp. The end point for protection is 10 seconds. Each mouse is tested at 0.5 and 2 hours after treatment with morphine and the test compound. Morphine has an $MPE_{50}$ of 3.2–5.6 mg./kg. (s.c.).

(c) Tail Immersion Procedure

The method is a modification of the receptacle procedure developed by Benbasset, et al., Arch. int. Pharmacodyn., 122, 434 (1959). Male albino mice (19–21 g.) of the Charles River CD-1 strain are weighed and marked for identification. Five animals are normally used in each drug treatment group with each animal serving as its own control. For general screening purposes, new test agents are first administered at a dose of 56 mg./kg. intraperitoneally or subcutaneously, delivered in a volume of 10 ml./kg. Preceding drug treatment and at 0.5 and 2 hours post drug, each animal is placed in the cylinder. Each cylinder is provided with holes to allow for adequate ventilation and is closed by a round nylon plug through which the animal's tail protrudes. The cylinder is held in an upright position and the tail is completely immersed in the constant temperature waterbath (56° C.). The endpoint for each trial is an energetic jerk or twitch of the tail coupled with a motor response. In some cases, the endpoint may be less vigorous post drug. To prevent undue tissue damage, the trial is terminated and the tail removed from the waterbath within 10 seconds. The response latency is recorded in seconds to the nearest 0.5 second. A vehicle control and a standard of known potency are tested concurrently with screening candidates. If the activity of a test agent has not retured to baseline values at the 2-hour testing point, response latencies are determined at 4 and 6 hours. A final measurement is made at 24 hours if activity is still observed at the end of the test day.

Test Using Chemical Nociceptive Stimuli

Suppression of Phenylbenzoquinone Irritant-Induced Writhing

Groups of 5 Carworth Farms CF-1 mice are pretreated subcutaneously or orally with saline, morphine, codeine or the test compound. Twenty minutes (if treated subcutaneously) or fifty minutes (if treated orally) later, each group is treated with intraperitoneal injection of phenylbenzoquinone, an irritant known to produce abdominal contractions. The mice are observed for 5 minutes for the presence or absence of writhing starting 5 minutes after the injection of the irritant. $MPE_{50}$'s of the drug pretreatments in blocking writhing are ascertained.

Tests Using Pressure Nociceptive Stimuli

Effect on the Haffner Tail Pinch Procedure

A modification of the procedure of Haffner, Experimentelle Prufung Schmerzstillender, Mittel Deutch Med. Wschr., 55, 731–732 (1929) is used to ascertain the effects of the test compound on aggressive attacking responses elicited by a stimulus pinching the tail. Male albino rats (50–60 g.) of the Charles River (Sprague-Dawley) CD strain are used. Prior to drug treatment, and again at 0.5, 1, 2 and 3 hours after treatment, a Johns Hopkins 2.5-inch "bulldog" clamp is clamped onto the root of the rat's tail. The endpoint at each trial is clear attacking and biting behavior directed toward the offending stimulus, with the latency for attack reported in seconds. The clamp is removed in 30 seconds if attacking has not yet occurred, and the latency of response is recorded as 30 seconds.

Tests Using Electrical Nociceptive Stimuli

The "Flinch-Jump" Test

A modification of the flinch-jump procedure of Tenen, Psychopharmacologia, 12, 278–285 (1968) is used for determining pain thresholds. Male albino rats (175–200 g.) of the Charles River (Sprague-Dawley) CD strain are used. Prior to receiving the drug, the feet of each rat are dipped into a 20% glycerol/saline solution. The animals are then placed in a chamber and presented with a series of 1-second shocks to the feet which are delivered in increasing intensity at 30-second intervals. These intensities are 0.26, 0.39, 0.52, 0.78, 1.05, 1.31, 1.58, 1.86, 2.13, 2.42, 2.72, and 3.04 mA. Each animal's behavior is rated for the presence of (a) flinch, (b) squeak and (c) jump or rapid forward movement at shock onset. Single upward series of shock intensities are presented to each rat just prior to, and at 0.5, 2, 4 and 24 hours subsequent to drug treatment.

Results of the above tests are recorded as percent maximum possible effect (% MPE). The % MPE of each group is statistically compared to the % MPE of the standard and the predrug control values. The % MPE is calculated as follows:

$$\% \ MPE = \frac{\text{test time} - \text{control time}}{\text{cutoff time} - \text{control time}} \times 100$$

The compounds of the present invention are active analgesics via oral and parenteral administration and are conveniently administered in composition form. Such compositions include a pharmaceutical carrier selected on the basis of the chosen route of administration and standard pharmaceutical practice. For example, they are administered in the form of tablets, powders or granules containing such excipients as starch, milk sugar, certain types of clay, etc. Alternatively, they are administered in capsules, in admixtures with the same or equivalent excipients, or in the form of oral suspensions, solutions, emulsions, syrups and elixirs which can contain flavoring and coloring agents. For oral administration of the therapeutic agents of this invention, tablets or capsules containing from about 0.01 to about 100 mg. are suitable for most applications.

The physician will determine the dosage which will be most suitable for an individual patient and it will vary with the age, weight and response of the particular patient and the route of administration. Generally, however, the initial analgesic dosage in adults is from 0.01 to 500 mg. per day in single or divided doses. In many instances, it is not necessary to exceed 100 mg. daily. The favored oral dosage range is from 0.01 to about 300 mg./day; the preferred range is from 0.10 to about 50 mg./day. The favored parenteral dose is from 0.01 to 100 mg./day; the preferred range is from 0.01 to 20 mg./day.

The use of these compounds for the treatment of glacuoma is believed to be due to their ability to reduce intraocular pressure. Their effects on intraocular pressure are determined by tests on dogs. The test drug is instilled into the eye of a dog in the form of a solution or is administered systemically at various periods of time after which the eye is anesthetized by instillation of tetracaine hydrochloride, $\frac{1}{2}\%$, 2 drops. A few minutes after this local anesthesia, intraocular pressure readings are taken with a Schiotz mechanical tonometer and after fluorescein dye is administereed, with a Holberg hand application tonometer. The test drug is conveniently used in a solution such as the following: test drug (1 mg.), ethanol (0.05 ml.), Tween 80 (polyoxyalkylene derivative of sorbitan mono-oleate, available from Atlas Powder Co., Wilmington, Del. 19899; 50 mg.) and saline (to make 1 ml.), or in a more concentrated solution wherein the ingredients are present in proportions of 10 mg., 0.10 ml., 100 mg. and 1 ml., respectively. Alternatively the compounds of the present invention are tested for their ability to reduce intraocular pressure in normal rabbits according to the method of Elsohly et al., J. Clin. Pharmacol. 21, pp. 472S–478S (1981). For human use, concentrations of drug from 0.01 mg./kg. to 10 mg./kg. are useful.

Their activity as diuretic agents is determined by the procedure of Lipschitz et al., J. Pharmacol., 79, 97 (1943) which utilizes rats as the test animals. The dosage range for this use is the same as that noted above with respect to their use as analgesic agents.

The antiemetic properties of the compounds of the present invention are determined in unanesthetized unrestrained cats according to the procedure described in Proc. Soc. Exptl. Biol. and Med., 160, 437-440 (1979). The dosage ranges for this utility is also the same as that noted above with respect to their analgesic utility.

This invention also provides pharmaceutical compositions, including unit dosage forms, valuable for the use of the herein described compounds as analgesics and other utilities disclosed herein. The dosage form may be given in single or multiple doses, as previously noted, to achieve the daily dosage effective for a particular utility.

The compounds (drugs) described herein can be formulated for administration in solid or liquid form for oral or parenteral administration. Capsules containing drugs of this invention; i.e.; compounds of formulae (I) to (IV) are prepared by mixing one part by weight of drug with nine parts of excipient such as starch or milk sugar and then loading the mixture into telescoping gelatin capsules such that each capsule contains 100 parts of the mixture. Tablets containing the same compounds are prepared by compounding suitable mixtures of drug and standard ingredients used in preparing tablets, such as starch, binders and lubricants, such that each tablet contains from 0.01 to 100 mg. of drug per tablet.

Suspensions and solutions of these drugs, particularly those wherein A (formulae I and II) is hydroxy, are generally prepared just prior to use in order to avoid problems of stability of the drug (e.g. oxidation) or of suspensions or solution (e.g. precipitation) of the drug upon storage. Compositions suitable for such are generally dry solid compositions which are reconstituted for injectable administration.

The present invention is illustrated by the following examples. However, it should be understood that the invention is not limited to the specific details of these examples.

When compounds containing more than one asymmetric center contain a center of unspecified absolute or relative stereochemistry (e.g. 5-phenyl-2-pentyl) it will be understood by those skilled in the art that the product is a mixture of two diasteroisomers or two racemates, respectively, usually in a ratio of about 1:1.

EXAMPLE 1

$O^1$-Ethyl $O^7$-Methyl 3-Oxoheptanedioate

A five liter round bottom flask was fitted with a mechanical stirrer, thermometer and a one liter addition funnel. The addition funnel was in turn fitted with a septum into which was introduced a $N_2$ line, an equalizing line and a liquid reagent inlet line. The equalizing line was further connected with tubing to a straight vacuum adapter and this adapter was fitted between the addition funnel and the flask. The flask was charged with $N_2$ and then with 976 ml. (2.05 moles=2.25 equiv.) n-butyllithium in 800 ml. of anhydrous tetrahydrofuran (THF), and the mixture cooled to $-78°$ C. in a dry ice/acetone bath. To this was added 408 ml. (2.05 moles) of dicyclohexylamine in 375 ml. THF dropwise over 45 minutes (temperature kept below $-67°$ C.). After equilibrating to $-78°$ C., 201 ml. (2.05 moles) of ethyl acetate in 100 ml. THF was added dropwise over 45 minutes (temperature kept below $-67°$ C.). The mixture was allowed to stir at $-78°$ C. for 15 minutes and then 150 g. (0.91 mole) of methyl 4-(chloroformyl)-butyrate in 200 ml. THF was added dropwise over 30 minutes (temperature kept below $-70°$ C.). After stirring for 1 hour at $-78°$ C., 231 ml. (2.05 moles) of glacial acetic acid was added dropwise over 25 minutes, after which the dry ice/acetone bath was removed, and the reaction allowed to warm to $0°$ C., diluted with one liter $Et_2O$, and the white inorganics filtered. The solids were washed well with ether. The combined filtrate and washes were evaporated in vacuo and the residue was partitioned between one liter ether and one liter water. The ether was separated, washed in sequence $2\times$ with 500 ml. 0.5N HCl, $1\times$ with 500 ml. $H_2O$, $1\times$ with 500 ml. saturated $NaHCO_3$, $1\times$ with 500 ml. $H_2O$ and $1\times$ with 500 ml. brine, dried over $MgSO_4$, filtered and evaporated in vacuo to yield 108.5 g. (55.1%) of title product as a gold colored mobile liquid. Nmr ($CDCl_3$): 4.1 (q, 2H), 3.6 (s, 3H), 3.4 (s, 2H), 1.7–2.7 (m, 6H), 1.25 (t, 3H). M/e: 216 (m+).

EXAMPLE 2

4-[2,3-dihydro-5,7-dihydroxy-1H-quinolin-4-on-2-yl]butyric Acid

In a Parr apparatus 41.0 g. (0.19 mole) of title product of the preceding Example was combined with 1.0 g. of PtO$_2$ catalyst and 29.1 g. (0.19 mole) of 3,5-dimethoxyaniline in 80 ml. glacial acetic acid, and the mixture hydrogenated at 50 psi for 36 hours, at which time TLC indicated the reaction was complete. Catalyst was recovered by filtration, with the aid of diatomaceous earth, washed well with acetic acid and the combined filtrate and washes concentrated in vacuo to 100 ml.

In a two liter three neck round bottom flask fitted with mechanical stirrer, thermometer, and water cooled condenser under a N$_2$ atmosphere was placed 360 ml. of 48% aqueous HBr and 200 ml. of glacial acetic acid. This mixture was heated to reflux and the 100 ml. acetic acid solution from the alkylation step above was added dropwise over 30 minutes. After addition the solution was refluxed an additional 30 minutes. The condenser was then replaced with a distilling head and the thermometer replaced with a N$_2$ stream. A colorless liquid was then allowed to distill out of the reaction. In all 500 ml. was collected over 3 hours. The dark residue was then cooled to room temperature, poured onto 500 ml. ice, and extracted 4× with 500 ml. ethyl acetate. The combined organic layers were dried over MgSO$_4$, filtered and evaporated in vacuo to yield 33 g. (65.5%) of title product as a light brown gum. TLC: R$_f$ 0.25 (19:1 ether:methanol). M/e: 265 (m+). IR (KBr): 1700 cm$^{-1}$.

Analysis: Calcd. for C$_{13}$H$_{15}$O$_5$N: C, 58.86; H, 5.70; N, 5.28. Found: C, 59.22; H, 5.70; N, 5.02.

EXAMPLE 3

4a,5-Dihydro-7,9-dihydroxy-2H,3H,4H-pyrido[1,2-a]quinoline-1,6-dione

Title product of the preceding Example (26 g., 0.098 mole) was combined with 260 ml. methanesulfonic acid and heated to 140° C. with stirring under a N$_2$ atmosphere. After two hours the reaction was cooled to room temperature and poured into one liter of ice. To this was added four liters of ethyl acetate along with one liter H$_2$O and ½ lb. salt, and the mixture stirred at room temperature for 16 hours. The layers were separated and the aqueous layer was extracted 4× with 500 ml. ethyl acetate. The combined ethyl acetate layers were washed with multiple portions of NaHCO$_3$ until pH 7 and no effervescense was observed. The ethyl acetate was then washed 1× with one liter H$_2$O, 1× with one liter brine, dried over MgSO$_4$, filtered and evaporated in vacuo. The residue was redissolved in a small amount of hot ethyl acetate, diluted with diethyl ether and cooled to 0° C. The solids were filtered and dried in vacuo to yield 9.4 g. (38.8%) of title product. M.p. 259–268° C. d. M/e: 247 (m+).

Analysis: Calcd. for C$_{13}$H$_{13}$O$_4$N: C, 63.15; H, 5.30; N, 5.67. Found: C, 63.22; H, 5.44; N, 5.35.

EXAMPLE 4

4a,5-Dihydro-7-hydroxy-9-(5-phenyl-2-pentyl-oxy)-2H,3H,4H-pyrido[1,2-a]quinoline-1,6-dione In a 250 ml. three neck round bottom flask under a nitrogen atmosphere fitted with a mechanical stirrer, thermometer, addition funnel and water cooled condenser was placed 19.5 g. (0.079 mole) product of the preceding Example and 24.0 g. (0.174 mole) anhydrous K$_2$CO$_3$ in 110 ml. of dry dimethylformamide (DMF). This mixture was warmed to an internal temperature of 90° C. for 10 minutes, then cooled to room temperature. To this mixture was added 21.0 g. (0.087 mole) of 5-phenyl-2-pentyl methanesulfonate (U.S. Pat. No. 4,260,764) in 20 ml. DMF dropwise over 5 minutes. The reaction was warmed to 90° C. for one hour. TLC at one hour shows the reaction to be complete. The reaction was poured into 800 ml. H$_2$O and extracted 4× with 500 ml. ethyl acetate. The ethyl acetate layers were combined and washed 3× with 300 ml. saturated NaHCO$_3$, 1× with 300 ml. H$_2$O and 1× with 300 ml. brine, dried over MgSO$_4$, filtered and evaporated in vacuo leaving a residual yellow liquid. The latter was chromatographed on 1.5 kg. silica gel (0.063–0.20 mm) with 2:1 toluene:ether as eluant and TLC monitoring. Product fractions were combined and evaporated in vacuo to yield 13.6 g. (43.7%) of title product (a mixture of two racemic pairs) as a viscous yellow-orange oil. TLC: R$_f$ 0.40 (49:1 ether:methanol). M/e: 393 (m+).

EXAMPLE 5

5-Formyl-4a,5-dihydro-7-hydroxy-9-(5-phenyl-2-pentyloxy)-2H,3H,4H-pyrido[1,2-a]quinoline-1,6-dione Using a flame dried 500 ml. three neck round bottom flask equipped with a mechanical stirrer, a water cooled condenser and an addition funnel with a N$_2$ inlet, a solution of 6.6 g. (0.017 mole) of title product of the preceding Example in 33 g. (0.420 mole) ethyl formate was added dropwise to 2.35 g. (0.098 mole) of NaH slurried in 40 ml. of ether. The addition rate was adjusted to maintain a gentle reflux. After 45 minutes TLC indicated the reaction was complete. The reaction was then diluted with 250 ml. ethyl acetate, poured into 25 ml. ice-water, acidified to pH 1.0 with 10% HCl, stirred 10 minutes, and the phases separated. The organic layer was washed 2× with 125 ml. H$_2$O, dried over MgSO$_4$, filtered and evaporated in vacuo to yield 6.7 g. (93% crude) of title product (a mixture of two racemic pairs) as an orange liquid. TLC: R$_f$ 0.2–0.5, stretched, Fast Blue positive. M/e: 421 (m+).

EXAMPLE 6

4aS*,5S*-Dihydro-7-hydroxy-5-(3-oxo-1-butyl)-9-(5-phenyl-2-pentyloxy)-2H,3H,4H-pyrido[1,2-a]quinoline-1,6-dione To a stirred solution of 6.7 g. (0.016 mole) of title product of the preceding Example in 25 ml. of methanol in a nitrogen atmosphere was added 0.8 ml. (0.0057 mole) of triethylamine followed by 3.0 ml. (0.037 mole) of methyl vinylketone. After stirring for 16 hours at room temperature the reaction was shown to be complete by TLC and was diluted with 300 ml. of ether and washed successively 4× with 100 ml. 10% Na$_2$CO$_3$, 2× with 100 ml. H$_2$O, 1× with 100 ml. brine, dried over MgSO$_4$, filtered and evaporated in vacuo, leaving a residual oil. TLC: R$_f$ 0.35–0.4, 2 spots (1:1 toluene:ether).

This intermediate oil was immediately dissolved in 50 ml. of methanol and stirred at room temperature under N$_2$ with 0.5 g. (0.0036 mole) of anhydrous K$_2$CO$_3$. After 4 hours TLC indicated the deformylation to be complete. To this suspension was added 0.43 g. (0.0072 mole) glacial acetic acid and the methanol was removed in vacuo. The residue was partitioned between 200 ml. water and 200 ml. ethyl acetate. The layers were separated and the aqueous layer was extracted 1× with 200 ml. ethyl acetate. The combined ethyl acetate layers were washed 2× with 200 ml. H$_2$O, 1× with 200 ml. brine, dried over MgSO$_4$, filtered and evaporated in vacuo leaving 5.1 g. of a crude brown oil. The oil was chromatographed on 300 g. silica gel eluting with 3:1 toluene/ether. Product fractions were combined and evaporated in vacuo yielding 2.6 g. (35.1%) of title product (a mixture of two racemic pairs, because of the side chain asymmetric carbon) as a yellow liquid. TLC: R$_f$0.35. M/e: 463 (m+). NMR (CDCl$_3$) includes methyl ketone peak (s, 2.1 ppm).

EXAMPLE 7

4aS*,4bR*,5,6-Tetrahydro-9-hydroxy-11-(5-phenyl-2-pentyloxy)-2H,3H,4H-pyrido[1,2-f]phenanthridine-1,7-dione A stirred solution of 2.6 g. (0.0056 mole) of title product of the preceding Example in 95 ml. (0.190 mole) of methanolic 2N KOH (freshly prepared by dissolving 1.32 g. of 85% KOH in 100 ml. of methanol) and 95 ml. methanol was heated at reflux for 18 hours under a nitrogen atmosphere, cooled to 10° C. in an ice-water bath, and quenched by adding 11.4 g. (0.19 mole) of glacial acetic acid dropwise over 10 minutes. The reaction was concentrated in vacuo to a semi-solid, which was washed 2× with 100 ml. H$_2$O and then extracted 2× with 100 ml. ethyl acetate. The combined ethyl acetate layers were washed 4× with 100 ml. saturated NaHCO$_3$ solution, 2× with 100 ml. H$_2$O, and stirred over 2 g. MgSO$_4$/2 g. activated carbon for 30 minutes. This mixture was filtered over diatomaceous earth, washing well with ethyl acetate. The solvent was removed in vacuo to yield 0.6 g. (24%) of title product (a mixture of two racemic pairs) as a yellow oil. TLC: R$_f$ 0.1 (ethyl acetate).

EXAMPLE 8

9-Acetoxy-4aS*,4bR*,5,6-tetrahydro-11-(5-phenyl-2-pentyloxy)-2H,3H,4H-pyrido[1,2-f]phenanthridine-1,7-dione Title product of the preceding Example (0.60 g., 0.0013 mole) was dissolved in 50 ml. of methylene chloride. While stirring under a N$_2$ amtosphere, 0.151 g. (0.0015 mole) of triethylamine, then 0.183 g. (0.0015 mole) of 4-(dimethylamino)pyridine, and finally 0.153 g. (0.0015 mole) of acetic anhydride were added. The reaction mixture was stirred at room temperature for 90 minutes then checked by TLC. The reaction was poured into 25 ml. H$_2$O, the methylene chloride was separated, washed 3× with 25 ml. 10% HCl, 1× with H$_2$O, 2× with 25 ml. saturated NaHCO$_3$ solution, 1× with 25 ml. H$_2$O, dried over MgSO$_4$ filtered and concentrated in vacuo to an oil. The oil was chromatographed on 35 g. silica gel (0.063-0.20 mm), eluting with ethyl acetate. Clean product fractions were combined and solvent removed in vacuo to yield 0.30 g. (47.3%) of title product (a mixture of two racemic pairs) as a yellow gum. TLC: R$_f$ 0.25 (ethyl acetate). M/e: 487 (m+).

EXAMPLE 9

9-Acetoxy-4,4aS*,4bR*,5,6,7R*,8,8aR*-octahydro-7-hydroxy-11-(5-phenyl-2-pentyl)2H,3H-pyrido[1,2-f]phenanthridin-1-one In a Parr apparatus, 0.3 g. (0.0006 mole) of title product of the preceding Example was combined with 0.3 g. 5% Pd/C and 25 ml. methanol and the mixture hydrogenated at 50 psi for 1.5 hours, at which time TLC indicated the reaction was complete. The catalyst was recovered by filtration over diatomaceous earth, washing well with methanol. The combined filtrate and washes were removed in vacuo to yield 0.26 g. (88.1%) of title product (a mixture of two racemic pairs) as a colorless oil. TLC: R$_f$0.20 (ethyl acetate).

EXAMPLE 10

2,3,4,4aS*,4bR*,5,6,7R*,8,8aR*-decahydro-7,9-dihydroxy-11-(5-phenyl-2-pentyl)-1H-pyrido[1,2-f]phenanthridine Title product of the preceding Example (0.26 g., 0.0005 mole) was dissolved in 25 ml. distilled THF. Lithium aluminum hydride (0.13 g.) was added in one portion and the suspension warmed to reflux for 1 hour at which time TLC indicated no starting material. The mixture was diluted with 100 ml. ethyl acetate and 50 ml. H$_2$O, stirred 10 minutes, the layers separated and the aqueous layer extracted 1× with 50 ml. ethyl acetate. The combined organic layers were dried over MgSO$_4$, filtered and solvent removed in vacuo to yield 0.21 g. (95.4%) of title product (a mixture of two racemic pairs) as a colorless oil. TLC: R$_f$0.1 (1:1 toluene:ether).

EXAMPLE 11

9-Acetoxy-2,3,4,4aS*,4bR*,5,6,7R*,8,8aR*-decahydro-7-hydroxy-11-(5-phenyl-2R*-pentyl)-1H-pyrido[1,2-f]phenanthridine Hydrochloride and 9-Acetoxy-2,3,4,4aS*,4bR*,5,6,7R*,8,8aR*-decahydro-7-hydroxy-11-(5-phenyl-2S*-pentyl)-1H-pyrido[1,2-f]phenanthridine Hydrochloride Title product from the preceding Example (0.21 g., 0.00043 mole) was dissolved in 5 ml. methylene chloride. Triethylamine (0.044 g., 0.00043 mole) was added, followed by 0.053 g. (0.00043 mole) of 4-(dimethylamino)-pyridine and then by 0.044 g. (0.00043 mole) of acetic anhydride. The solution was stirred at room temperature under a N$_2$ atmosphere for 45 minutes. After checking the reaction by TLC, the reaction mixture was diluted with 50 ml. methylene chloride, washed 1× with 50 ml. 10% HCl, 1× with 50 ml. H$_2$O, 1× with 50 ml. saturated NaHCO$_3$ solution and 1× with 50 ml. brine, dried over MgSO$_4$, filtered and solvent removed in vacuo to yield a brown oil. The oil was chromatographed on 25 g. silica gel (0.063-0.20 mm), eluting with 3:1 toluene:ether. Similar fractions were combined and solvent removed in vacuo to yield a second brown oil. The latter was dissolved in 25 ml. ether and 25 ml. hexane, dry HCl was bubbled in, and the white solid precipitate was filtered and dried in vacuo to yield 0.04 g. (18.1%) of an approximately 1:1 mixture of title products, m.p. 110°-130° C. d. TLC: R$_f$0.2 (1:1 toluene:ether).

Analysis: Calcd. for C$_{30}$H$_{39}$O$_4$N.HCl:

C, 70.10; H, 7.84; N, 2.73; m/e 477. Found: C, 69.23; H, 7.91; N, 2.75; m/e 477.

By the same method, substituting for acetic anhydride, one equivalent of propionyl chloride, butyryl chloride, isovaleryl chloride, benzoyl chloride, the mono acid chloride of malonic acid, succinic anhydride, glutaric anhydride, 4-morpholinobutyryl chloride hydrochloride, 3-dimethylaminopropionyl chloride hydrochloride, 5-piperidinovaleryl chloride hydrochloride and 2-pyrrolidinoacetyl chloride hydrochloride, the corresponding 9-propionyloxy-, 9-butyryloxy-9-isovaleryloxy-, 9-benzoyloxy-, 9-(2-carboxyacetyloxy-, 9-(3-carboxypropionyloxy)-, 9-(5-carboxyvaleroyloxy)-, 9-(4-morpholinobutyryloxy)-, 9-(3-dimethylaminopropionyloxy)-, 9-(5-piperidinovaleroyloxy)- and 2-pyrrolidinoacetoxy-derivatives are prepared.

Using two equivalents of acetic anhydride, propionyl chloride, butyryl chloride or isovaleryl chloride and two equivalents of 4-(dimethylamino)pyridine, the same process is employed to prepare 7,9-bis(acetoxy)-2,3,4aS*,4bR*,5,6,7R*,8,8aR*-decahydro- 11-(5-phenyl-2R*-pentyl)-1H-pyrido[1,2-f]phenanthridine and 7,9-bis(acetoxy)-2,3,4aS*,4bR*,5,6,7R*,8,8aR*-decahydro-11-(5-phenyl-2S*-pentyl)-1H-pyrido[1,2-f]-phenanthridine, as well as the corresponding 7,9-bis(propionyloxy)-, 7,9-bis-(butyryloxy)- and 7,9-bis-(isovaleroyloxy)-derivatives.

Using the same process, but substituting an equivalent of the appropriate 7-hydroxy-9-acyloxy compound as substrate, the corresponding 7-acetoxy-9-propionyloxy-, 7-acetoxy-9-(4-morpholinobutyryloxy)- 0 and 7-acetoxy-9-(2-carboxyacetyl)-derivatives are prepared.

Substituting the appropriate 7-hydroxy-9-acyloxy compound as substrate, and substituting acetic anhydride with equivalent propionyl chloride, isovaleryl chloride, methyl chloroformate, isobutyl chloroformate, methanesulfonyl chloride, 1-pentanesulfonyl chloride or 2-pentansulfonyl chloride, the corresponding 7-propionyloxy-9-acetoxy-7-isovaleroyloxy-9-acetoxy-, 7-methoxycarbonyloxy-9-propionyloxy-, 7-isobutoxycarbonyloxy-9-isobutyryloxy-, 7-methanesulfonyloxy-9-acetoxy-, 7-(1-pentanesulfonyloxy)-9-acetoxy- and 7-(2-pentanesulfonyloxy)-9-acetoxy-derivatives are prepared.

EXAMPLE 12

3a,4-Dihydro-6,8-dihydroxy-2H,3H-pyrrolo[1,2-a]quinoline-1,5-dione

By the procedures of Examples 2 and 3, diethyl 3-oxohexanedioate [Tetrahedron 23, p. 897 (1967)] and 3,5-dimethoxyaniline were converted to title product, recrystallized from ethyl acetate/cyclohexane, in 77% yield, m.p. 254°–256° C.; m/e 233 (m+); ir (KBr) 3448, 2857, 1680, 1639 cm$^{-1}$.

EXAMPLE 13

3a,4-Dihydro-6-hydroxy-8-(5-phenyl-2-pentyl)-2H,3H-pyrrolo[1,2-a]quinoline-1,5-dione By the procedure of Example 4, the product of the preceding Example was converted to title product in 39% yield, m.p. 127°–130° C.; ir (KBr) 1250 cm$^{-1}$.

Analysis: Calcd. for $C_{23}H_{25}O_4N$:

C, 72.80; H, 6.64; N, 3.69. Found: C, 72.62; H, 6.56; N, 3.63.

EXAMPLE 14

4-Formyl-3a,4-dihydro-6-hydroxy-8-(5-phenyl-2-pentyl)-2H,3H-pyrrolo[1,2-a]quinoline-1,5-dione By the procedure of Example 5, the product of the preceding Example was converted to title product as a brown foam in 78% yield. $^1$H—NMR (CDCl$_3$) includes characteristic singlet at 7.6 ppm. TLC: R$_f$ 0.1 stretched (1:1 toluene:ether).

EXAMPLE 15

3aS*,4S*-Dihydro-6-hydroxy-4-(3-oxo-1-butyl)-8-(5-phenyl-2-pentyloxy)-2H,3H-pyrrolo[1,2-a]quinoline-1,5-dione By the procedure of Example 6, the product of the preceding Example was converted to title product (a mixture of two racemic pairs) as a light brown oil in 85% yield. TLC: R$_f$ 0.2, 0.3 (1:1 toluene:ether), R$_f$ 0.2 (19:1 ether:methanol). $^1$H—NMR (CDCl$_3$) includes characteristic methyl singlet at 2.15 ppm.

EXAMPLE 16

3aS*,3bR*,4,5-Tetrahydro-8-hydroxy-10-(5-phenyl-2-pentyloxy)-2H, 3H-pyrrolo[1,2-f]phenanthridine-1,6-dione By the procedure of Example 7, the product of the preceding Example was converted to title product (a mixture of two racemic pairs) in the same yield, recrystallized from methanol, m.p. 208°–210° C.; TLC: R$_f$ 0.5 (19:1 ether:methanol), R$_f$ 0.5 (9:1 ether: methanol).

Analysis: Calcd. for $C_{27}H_{29}O_4N$: C, 75.15; H, 6.77; N, 3.25. Found: C, 75.57; H, 6.78; N, 3.44.

EXAMPLE 17

3,3aS*,3bR*,4,5,6R*,7,7aR*-Octahydro-6,8-dihydroxy-10-(5-phenyl-2-pentyloxy)-2H-pyrrolo[1,2-f]phenanthridin-1-one By the procedure of Example 9, product of the preceding Example was converted to the title product (a mixture of two racemic pairs) in 83% yield, m.p. 205°–206° C. TLC: R$_f$ 0.7 (9:1 ether:methanol), R$_f$ 0.1 (1:1 toluene:ether).

Analysis: Calcd. for $C_{29}H_{37}O_4N$: C, 75.13; H, 8.05; N, 3.02; m/e 463. Found: C, 75.31; H, 8.16; N, 3.14; m/e 463.

EXAMPLE 18

8-Acetoxy-1,2,3,3aS*,3bR*,4,5,6R*,7,7aR*-decahydro-6-hydroxy-10-(5-phenyl-2S*-pentyloxy)pyrrolo[1,2-f]phenanthridine (Isomer A)

and

8-Acetoxy-1,2,3,3aS*,3bR*,4,5,6R*,7,7aR*-decahydro-6-hydroxy-10-(5-phenyl-2R*-pentyloxy)pyrrolo[1,2-f]phenanthridine (Isomer B)

Lithium aluminum hydride (1.6 g.) was suspended by stirring in 50 ml. of distilled THF. Product of the preceding Example (3.64 g.) was dissolved in 100 ml. of additional THF and added dropwise to the suspension over 10 minutes. Minor foaming and warming was noted. The mixture was heated to reflux for one hour, by which time TLC indicated starting material had been consumed [R$_f$ of starting material 0.3, R$_f$ of product 0.5 (20:1 ether:methanol)]. The reaction mixture was cooled, poured into 500 ml. of ethyl acetate, slowly diluted with 250 ml. of 5% acetic acid, stirred 10 minutes, the layers separated, and the aqueous phase extracted with 250 ml. of fresh ethyl acetate. The organic layers were combined, washed 1×500 ml. H$_2$O, 2×500 ml. saturated NaHCO$_3$ and 1×brine, dried (MgSO$_4$) and concentrated to yield 3 g. (0.0071 mole) of intermediate 6,8-hydroxy compound as a colorless oil, having R$_f$ as noted above.

The entire batch of intermediate 6,8-dihydroxy compound was taken up in 150 ml. of CH$_2$Cl$_2$ and acetylated with 690 mg. (0.0069 mole) of acetic anhydride in the presence of 690 mg. (0.0069 mole) of triethylamine and 842 mg. (0.0069 mole) of 4-dimethylaminopyridine. After 2 hours at room temperature, crude products were isolated following the isolation procedure of Example 8. The resulting oil was chromatographed on 300 g. of silica gel, using 3:1 toluene:ether as eluant, TLC monitoring and collecting 400 25 ml. fractions. Clean product fractions 161-400 were combined and evaporated to a second oil (2.4 g.). The oil was taken up in 20 ml. of ether and crude title isomer A crystallized by the addition of 40 ml. of hexane and scratching (1.1 g.). A portion of the crude (1 g.) was triturated with 50 ml. of ether, filtered away from 22 mg. of brown solids, and the filtrate cooled and diluted with 250 ml. of hexane to yield purified isomer A [0.49 g.; m/e 463; ir (KBr) 3390, 1767 cm$^{-1}$; $^1$H—NMR (CDCl$_3$) includes 7.3 (5H, m), 5.9 (quintet, 2H), 4.35 (quintet, 1H), 3.8 (m, 1H), 2.36 (s, 3H) ppm].

Analysis: Calcd. for C$_{29}$H$_{37}$O$_4$N: C, 75.13; H, 8.05; N, 3.02. Found: C, 75.31; H, 8.16; N, 3.14.

The ether/hexane mother liquor from the isolation of crude isomer A was concentrated to dryness to yield crude isomer B (850 mg.). A portion of the latter crude (750 mg.) was taken into 35 ml. of ether, filtered away from a small amount of insoluble matter and rechromatographed on 40 g. of silica gel using 1:1 toluene:ether as eluant, collecting 50 15 ml. fractions. Clean product fractions 21-40 were combined and evaporated to yield isomer B (400 mg.), as a colorless oil. The latter was converted to solid hydrochloride salt (300 mg.) by dissolving in 40 ml. of ether and bubbling in excess HCl gas.

Analysis: Calcd. for C$_{29}$H$_{37}$O$_4$N.HCl: C, 69.66; H, 7.66; N, 2.80; m/e 463. Found: C, 71.36; H, 7.78; N, 2.89; m/e 463.

EXAMPLE 19

Methyl dl-2-[1-(3,5-dimethoxyphenyl)pyrrolidin-2-yl]acetate

Under a nitrogen atmosphere, a mixture of 52 g. (0.340 mole) 3,5-dimethoxyaniline, 108.8 g. (0.378 mole) methyl dl-3,6-dibromocaproate, 60 ml. pyridine and 160 ml. tetrahydrofuran were stirred at room temperature overnight. The tetrahydrofuran was distilled off at atmospheric pressure and the remaining mixture heated at 100° C. for 2.5 hours. Additional methyl dl-3,6-dibromocaproate (5.7 g.) and pyridine (3.16 ml.) was added and heating at 100° C. resumed for an additional 2.5 hours. The pyridine was evaporated in vacuo, the residue partitioned between water and methylene chloride, the aqueous phase extracted with 4×150 ml. methylene chloride and the combined organic layers washed with 75 ml. brine. The washed extracts were dried (MgSO$_4$) and solvent evaporated to afford 57.5 g. of orange solid. The latter was placed on a silica gel column and eluted with methylene chloride for 42 fractions, methylene chloride containing 5% (v/v) ethyl acetate for 10 fractions, then the latter solvent alone for three fractions. Fractions 4-44 were combined and evaporated in vacuo to afford 53.6 g. (56%) of product. $^1$H—NMR (CDCl$_3$) ppm (delta): 3.70 (s, 3H, —COOCH$_3$), 3.78 (s, 6H, OCH$_3$), 5.80 (s, 3H, aromatic).

EXAMPLE 20 dl-2-[1-(3,5-Dimethoxyphenyl)pyrrolidin-2-yl]acetic Acid

A mixture of 53.6 g. (0.192 mole) methyl dl-2-[1-(3,5-dimethoxyphenyl)pyrrolidin-2-yl]acetate and 250 ml. methanol was warmed to obtain a solution and 22.8 g. (0.57 mole) sodium hydroxide in 200 ml. water was added. The resulting mixture was stirred at room temperature for 2.5 hours, the methanol evaporated and the aqueous residue cooled in ice. To this was added dropwise 48 ml. concentrated hydrochloric acid, the mixture extracted with 4×150 ml. methylene chloride, the extract washed with water, dried (MgSO$_4$) and the solvent evaporated to afford 48.9 g. (96%) of product. $^1$H—NMR (CDCl$_3$) ppm (delta): 3.80 (s, 6H, OCH$_3$), 4.10 (m, 1H, N—CH), 5.82 (s, 3H, aromatic), 11.0 (s, 1H, COOH). Mass spectrum (m/e): 206 (base peak), 265 (m+).

EXAMPLE 21

Resolution via alpha-Methylbenzylamine Salt

A. Dextrorotatory salt

A mixture of 52.3 g. 0.197 mole) dl-2-[1-(3,5-dimethylphenyl)pyrrolidin-2-yl]acetic acid and 370 ml. ethyl acetate was heated to effect solution, 24.4 g. (0.201 mole) d-(+)-alpha-methylbenzylamine was added. The mixture was stirred for 10 minutes, then allowed to stand at room temperature for three hours to initiate crystallization. Then 370 ml. ethyl ether was added and the resulting mixture refrigerated overnight. Filtration, washing with cold ether gave 72.2 g. of solids. Evaporation of the mother liquors afforded an additional 4.7 g. of brown solid.

To the first crop (72.2 g.) was added 1440 ml. ethyl acetate and the mixture heated until a solution was obtained. The solution was allowed to stand overnight at room temperature, filtered, and the crystals washed with cold ether and dried in vacuo to afford 40.9 g., m.p. 129°-130° C., [alpha]$_D$+13.5° (c=1, CHCl$_3$). After two recrystallizations from ethyl acetate, 9.7 g. of pure salt was obtained, m.p. 141°-142° C., [alpha]D+32° C.(c=1, CHCl$_3$).

B. Levorotatory salt

The mother liquors from above were acidified with 167 ml. 1N hydrochloric acid, extracted with 5 x 125 ml. ethyl acetate, the extracts combined, washed with brine, dried (MgSO$_4$) and the solvent evaporated to obtain 49 g. of residue. This was dissolved in 350 ml. warm ethyl acetate, 22.4 g. l-(−)-alpha-methylbenzylamine added and the solution cooled to room temperature. Ethyl ether, 350 ml., was added and the mixture refrigerated overnight. The precipitated solid was collected by filtration, washed with cold ether and dried in vacuo to obtain 44.0 g. of salt. This was dissolved in 880 ml. ethyl acetate and set aside at room temperature for six hours. Filtration gave 12.4 g., m.p. 139°-140° C. After standing overnight, the mother liquor afforded a second crop, 11.66 g., m.p. 139°-140° C. The optical rotation (in chloroform) for the first crop was [alpha]$_D$−30.9°, and [alpha]$_D$−26.6° (c=1, CHCl$_3$) for the second crop.

The two crops were combined and recrystallized from 480 ml. ethyl acetate to afford 18.0 g. of salt, m.p. 141°-142° C., [alpha]$_D$−34.4° (c=1, CHCl$_3$).

EXAMPLE 22

A.
d-(+)-2-[1-(3,5-dimethoxyphenyl)pyrrolidin-2-yl]-acetic Acid

The dextrorotatory salt, obtained in the previous Example, 22.0 g., was recrystallized from ethyl acetate (440 ml.) to obtain 17.5 g. of salt, m.p. 142°–143° C., $[alpha]_D+33.8°$. This was treated with 47 ml. 1N hydrochloric acid, extracted with 4×100 ml. ethyl acetate, and the extracts washed with brine and dried over magnesium sulfate. Evaporation of solvent in vacuo gave 12.9 g. of d-(+)-acid as a green oil. A portion was decolorized by passing it through a short column of silica gel, $[alpha]_D+31.4°$ (c=1, CHCl$_3$).

B.
1-(−)-2-[1-(3,5-dimethoxyphenyl)pyrrolidin-2-yl]-acetic Acid

To 18.0 g. of the levorotatory salt obtained in the previous Example, was added 46.5 ml. 1N hydrochloric acid and the resulting mixture worked up as in Part A, above, to obtain 13.2 g. of product $[alpha]_D-36.4°$ (c=1, CHCl$_3$).

EXAMPLE 23 dl-, d-(+)- and 1-(−)-6,8-Dimethoxy-2,3,3a,4-tetrahydro-1H-pyrrolo[1,2-a]quinolin-5-one

A. Dextrorotatory isomers

A mixture of 13.2 g. (46.5 mmole) 1-(−)-2-[1-(3, 5-dimethoxyphenyl)pyrrolidin-2-yl]acetic acid, 6.5 g. sodium acetate, 100 ml. acetic acid and 100 ml. acetic anhydride was heated on the steam bath for 35 minutes. The volatiles were evaporated in vacuo, the residue mixed with methylene chloride, and the organic layer separated. After washing the organic phase with sodium bicarbonate solution (3×50 ml.), drying (MgSO$_4$) and evaporation of solvent, 11.2 g. (91%) of crude product was obtained. A 300 mg. portion was crystallized from methylene chloride/hexane, m.p. 126°–127° C., $[alpha]_D+141°$ (c=1, CHCl$_3$). Mass spectrum (m/e): 247 M+.

B. Levorotatory isomers

A mixture of 12.9 g. (48.6 mole) d-(+)-2-[1-(3,5-dimethoxyphenyl)pyrrolidin-2-yl]acetic acid, 6.4 g. sodium acetate and 50 ml. each of acetic acid and acetic anhydride gave 11.2 g. of crude product by the above procedure. Recrystallization of a portion from methylene chloride gave purified isomer, m.p. 129°–130° C., $[alpha]_D-146.2°$ (c=1, CHCl$_3$).

C. Racemate

By the same procedure, dl-2-[1-(3,5-dimethoxyphenyl)pyrrolidin-2-yl]acetic acid is converted to dl-6,8-dimethoxy-2,3,3a,4-tetrahydro-1H-pyrrolo[1,2-a]quinolin-5-one.

EXAMPLE 24 dl-, d-(+)- and 1-(−)-6,8-Dihydroxy-2,3,3a,4-tetrahydro-1H-pyrrolo[1,2-a]quinolin-5-one

A. Dextrorotatory isomer

A mixture of 11.2 g. (45.3 mmole) d-(+)-6,8-dimethoxy-2,3,3a,4-tetrahydro-1H-pyrrolo[1,2-a]quinolin-5-one and 100 ml. each of acetic acid and 48% hydrobromic acid was heated under a nitrogen atmosphere at 67° C. for 2.5 hours. The reaction mixture was concentrated in vacuo, the residue mixed with water and adjusted to pH 7.0 with sodium bicarbonate solution. The neutral mixture was extracted with 6×100 ml. ethyl acetate, the combined extracts washed with brine, dried (MgSO$_4$) and the solvent evaporated in vacuo to afford 9.0 g. (91%) of product as a yellow solid. A 100 mg. sample was crystallized from chloroform, m.p. 202°–203° C., $[alpha]_D+108°$ (c=1, CHCl$_3$) Mass spectrum (m/e): 218 (base peak), 219 (M+).

B. Levorotatory isomer

By the same procedure 10.2 g. 1-(−)-6,8-dimethoxy-b 2,3,3a,4-tetrahydro-1H-pyrrolo[1,2-a]quinolin-5-one and 50 ml. each of acetic acid and 48% hydrobromic acid afforded 9.2 g. of product, m.p. 190°–192° C., $[alpha]_D-91.4°$ (c=1, CHCl$_3$)

C. Racemate

By the same procedure d1-6,8-dimethoxy-2,3,3a,4-tetrahydro-1H-pyrrolo[1,2-a]quinolin-5-one is converted to d1-6,8-dihydroxy-2,3,3a,4-tetrahydro-1H-pyrrolo[1,2-a]quinolin-5-one.

EXAMPLE 25

By the method of Example 4, the appropriate racemic or optically active dihydroxy compound of the preceding Example is reacted with the appropriate racemic or optically active 5-phenyl-2-pentyl mesylate to produce:
2,3,3a,4-tetrahydro-6-hydroxy-8-(5-phenyl-2-pentyloxy)-1H-pyrrolo[1,2-a]quinolin-5-one, as a mixture of two racemates;
2,3,3aR,4-tetrahydro-6-hydroxy-8-(5-phenyl-2R-pentyloxy)-1H-pyrrolo[1,2-a]quinolin-5-one;
2,3,3aR,4-tetrahydro-6-hydroxy-8-(5-phenyl-2S-pentyloxy)-1H-pyrrolo[1,2-a]quinolin-5-one;
2,3,3aS,4-tetrahydro-6-hydroxy-8-(5-phenyl-2S-pentyloxy)-1H-pyrrolo[1,2-a]quinolin-5-one; and
2,3,3aS,4-tetrahydro-6-hydroxy-8-(5-phenyl-2R-pentyloxy)-1H-pyrrolo[1,2-a]quinolin-5-one.

Note that since this reaction occurs with inversion, the precursor mesylate has configuration opposite to that of the product.

EXAMPLE 26

Methyl dl-2-[1-(3,5-dimethoxyphenyl)piperidin-2-yl]acetate

By the procedure of Example 19, 23.7 g. (0.155 mole) 3,5-dimethoxyaniline and 52.3 g. (0.173 mole) of methyl 3,7-dibromoheptanoate, 26.9 g. pyridine and 80 ml. tetrahydrofuran (THF) were combined and stirred overnight at room temperature. The THF was removed by distillation at atmospheric pressure and an additional 5.8 g. 3,7-dibromoheptanoate and 3.3 g. of pyridine were added. The mixture was heated at 100° C. for five hours, then concentrated in vacuo. The residue was dissolved in methylene chloride and worked up as described in Example 19 to afford 38 g. of crude product. The crude material was taken up in toluene and placed on a column of 400 g. of silica gel (230–400 mesh) and eluted with 2:1 (v/v) ethyl acetate:methanol taking 300 ml. fractions. Fractions 3–10 were combined and evaporated to dryness to give 14.6 g. of product. $^1$H—NMR (CDCl$_3$) ppm (delta): 2.58 (d, 2H, C$\underline{H}$ $_2$CO$_2$CH$_3$), 3.64

(s, 3H, CO$_2$CH$_3$), 3.78 (s, 6H, OCH$_3$), 4.30 (m, 1H, —NC<u>H</u>—CH$_2$CO$_2$CH$_3$), 6.2–5.8 (m, 3H, aromatic).

EXAMPLE 27 d-, l- and dl-2-[1-(3,5-Dimethoxyphenyl)piperidin-2-yl]acetic Acid

A mixture of 14.5 g. (0.049 mole) methyl dl-2-[1-3,5-dimethoxyphenyl)piperidin-2-yl]acetate, 49 ml. 5N sodium hydroxide and 100 ml. methanol was stirred at room temperature overnight. Water, 250 ml. was added, the mixture acidified with 1N hydrochloric acid to pH 5 and extracted with ethyl acetate. The extracts were combined, washed with brine, dried (MgSO$_4$) and evaporated in vacuo to yield 12.2 g. (90%) of dl product as an oil. $^1$H—NMR (CDCl$_3$) ppm (delta): 2.55 (d, 2H, C<u>H</u>$_2$COOH), 3.80 (s, 6H), 6.30–5.80 (m, 3H), 11.0 (s, 1H, CO<u>O</u>H).

By the methods of Examples 21 and 22, the above acid is resolved into its enantiomeric forms:

d-2-[1-(3,5-dimethoxyphenyl)piperidin-2-yl]-acetic acid; and l-2-[1-(3,5-dimethoxyphenyl)piperidin-2-yl]-acetic acid.

EXAMPLE 28 d-, l- and dl-3,4,4a,5-tetrahydro-7,9-dimethoxy-1H,2H-pyrido[1,2-a]quinolin-6-one Under a nitrogen atmosphere, a mixture of 12.1 g. (0.043 mole) dl-2-[1-(3,5-dimethoxyphenyl)piperidin-2-yl]acetic acid, 100 ml. glacial acetic acid, 6.0 g. sodium acetate and 100 ml. acetic anhydride was stirred at room temperature overnight. The acetic acid and acetic anhydride were removed by evaporation in vacuo, the residue partitioned between methylene chloride and saturated aqueous sodium bicarbonate solution, and the organic phase washed with sodium bicarbonate, water, brine and dried (MgSO$_4$) The extracts were evaporated to dryness to give 13 g. of a green oil. The oil was purified by chromatography on a column containing 300 g. of silica gel (230–400 mesh), eluting with ethyl acetate. Fractions of 300 ml. each were taken. Fractions 7–12 were combined and evaporated to afford 5.5 g. of the desired dl product, M.P. 91°–94° C. $^1$H—NMR (CDCl$_3$) ppm (delta): 2.50 (m, 2H, C<u>H</u>$_2$CO), 3.79 (s, 3H), 3.81 (s, 3H), 5.90 (m, 2H). After recrystallization from isopropyl ether, 2.6 g. of crystals were obtained, M.P. 92°–93° C.

By the same method, the optically active acids of the preceding Example are converted to the corresponding d- and l-forms of the title product.

EXAMPLE 29 d-, l- and dl-3,4,4a,5-tetrahydro-7,9-dihydroxy-1H,2H-pyrido[1,2-a]quinolin-2-one By the procedure of Example 24, the compounds of the preceding Example are each hydrolyzed to the corresponding title compound.

EXAMPLE 30

3,4,4a,5-Tetrahydro-7-hydroxy-9-(5-phenyl-2-pentyloxy)-1H,2H-pyrido[1,2-a]quinolin-6-one By the method of Example 4, dl-3,4,4a,5-tetrahydro-7,9-dihydroxy-1H,2H-pyrido[1,2-a]quinolin-2-one of the preceding Example is reacted with racemic 5-phenyl-2-pentyl mesylate to yield title product, a mixture of two racemates.

By the same method, the appropriate optically active dihydroxy compound of the preceding Example is reacted with the appropriate optically active 5-phenyl-2-pentyl mesylate to yield:

3,4,4aR,5-tetrahydro-7-hydroxy-9-(5-phenyl-2R-pentyloxy)-1H,2H-pyrido[1,2-a]quinolin-6-one;

3,4,4aR,5-tetrahydro-7-hydroxy-9-(5-phenyl-2S-pentyloxy)-1H,2H-pyrido[1,2-a]quinolin-6-one;

3,4,4aS,5-tetrahydro-7-hydroxy-9-(5-phenyl-2S-pentyloxy)-1H,2H-pyrido[1,2-a]quinolin-6-one; and 3,4,4aS,5-tetrahydro-7-hydroxy-9-(5-phenyl-2R-pentyloxy)-1H,2H-pyrido[1,2-a]quinolin-6-one.

By the same method, the appropriate mesylate (Preparations 1–6) is reacted with the appropriate optically active or racemic dihydroxy compound of the preceding Example to yield:

3,4,4a,5-tetrahydro-7-hydroxy-9-(2-phenyl-1-butoxy)-1H,2H-pyrido[1,2-a]quinolin-6-one (two racemates);

3,4,4a,5-tetrahydro-7-hydroxy-9-(3-phenyl-1-butoxy)-1H,2H-pyrido[1,2-a]quinolin-6-one (two racemates);

3,4,4a,5-tetrahydro-7-hydroxy-9-(4-phenyl-1-butoxy)-1H,2H-pyrido[1,2-a]quinolin-6-one;

3,4,4a,5-tetrahydro-7-hydroxy-9-(1-phenyl-2-butoxy)-1H,2H-pyrido[1,2-a]quinolin-6-one (two racemates);

3,4,4a,5-tetrahydro-7-hydroxy-9-(4-phenyl-2-butoxy)-1H,2H-pyrido[1,2-a]quinolin-6-one (two racemates);

3,4,4a,5-tetrahydro-7-hydroxy-9-(5-phenyl-1-pentoxy)-1H,2H-pyrido[1,2-a]quinolin-6-one;

3,4,4a,5-tetrahydro-7-hydroxy-9-[3-(3-pyridyl)-1-propoxy]-1H,2H-pyrido[1,2-a]quinolin-6-one;

3,4,4a,5-tetrahydro-7-hydroxy-9-(1-tridecyloxy)-1H,2H-pyrido[1,2-a]quinolin-6-one;

3,4,4a,5-tetrahydro-7-hydroxy-9-(1-dodecyloxy)-1H,2H-pyrido[1,2-a]quinolin-6-one;

3,4,4a,5-tetrahydro-7-hydroxy-9-(2-decyloxy)-1H,2H-pyrido[1,2-a]quinolin-6-one (two racemates);

3,4,4a,5-tetrahydro-7-hydroxy-9-(4-decyloxy)-1H,2H-pyrido[1,2-a]quinolin-6-one (two racemates);

3,4,4a,5-tetrahydro-7-hydroxy-9-(3-octyloxy)-1H,2H-pyrido[1,2-a]quinolin-6-one (two racemates);

3,4,4a,5-tetrahydro-7-hydroxy-9-(4-heptyloxy)-1H,2H-pyrido[1,2-a]quinolin-6-one;

3,4,4a,5-tetrahydro-7-hydroxy-9-(5-methyl-2-hexyloxy)-1H,2H-pyrido[1,2-a]quinolin-6-one (two racemates);

3,4,4a,5-tetrahydro-7-hydroxy-9-(4-methyl-1-pentoxy)-1H,2H-pyrido[1,2-a]quinolin-6-one;

3,4,4a,5-tetrahydro-7-hydroxy-9-[1-(3-chlorophenyl)-1-butoxy]-1H,2H-pyrido[1,2-a]quinolin-6-one two racemates);

3,4,4a,5-tetrahydro-7-hydroxy-9-[1-(3-fluorophenyl)-1-propoxy]-1H,2H-pyrido[1,2-a]quinolin-6-one two racemates);

3,4,4aS,5-tetrahydro-7-hydroxy-9-(2S-octyl)-1H,2H-pyrido[1,2-a]quinolin-6-one; and 3,4,4aS,5-tetrahydro-7-hydroxy-9-(2R-octyl)-1H,2H-pyrido[1,2-a]quinolin-6-one.

EXAMPLE 31

4-Formyl-2,3,3a,4-tetrahydro-6-hydroxy-8-(5-phenyl-2-pentyloxy)-1H-pyrrolo[1,2-a]quinolin-5-one By the method of Example 5, the title compound of the preceding Example is converted to present title product.

By the same method, the other compounds of Examples 25 and 30 are converted to the corresponding 4-formyl-1H-pyrrolo[1,2-a]quinolin-5-ones and 5-formyl-1H,2H-pyrido[1,2-a]quinolin-6-ones.

EXAMPLE 32

By the method of Example 6, the compounds of the preceding Example are condensed with methyl vinyl ketone and then deformylated to yield the corresponding 4-(3-oxo-1-butyl)-1H-pyrrolo[1,2-a]quinolin-5-ones and 5-(3-oxo-1-butyl)-1H,2H-pyrido[1,2-a]quinolin-6-ones.

EXAMPLE 33

By the method of Example 7, the compounds of the preceding Example are cyclized to produce 3a,3b-trans/4a,4b-trans compounds as follows:

2,3,3aS*,3bR*,4,5-hexahydro-8-hydroxy-10-(5-phenyl-2-pentyloxy)-1H-pyrrolo[1,2-f]phenanthridin-6-one, a mixture of two racemates;

2,3,3aR,3bS,4,5-hexahydro-8-hydroxy-10-(5-phenyl-2R-pentyloxy)-1H-pyrrolo[1,2-f]phenanthridin-6-one;

2,3,3aR,3bS,4,5-hexahydro-8-hydroxy-10-(5-phenyl-2S-pentyloxy)-1H-pyrrolo[1,2-f]phenanthridin-6-one;

2,3,3aS,3bR,4,5-hexahydro-8-hydroxy-10-(5-phenyl-2S-pentyloxy)-1H-pyrrolo[1,2-f]phenanthridin-6-one;

2,3,3aS,3bR,4,5-hexahydro-8-hydroxy-10-(5-phenyl-2R-pentyloxy)-1H-pyrrolo[1,2-f]phenanthridin-6-one;

3,4,4aS*,4bR*,5,6-hexahydro-9-hydroxy-11-(5-phenyl-2-pentyloxy)-1H,2H-pyrido[1,2-f]phenanthridin-7-one, as a mixture of racemates;

3,4,4aR,4bS,5,6-hexahydro-9-hydroxy-11-(5-phenyl-2R-pentyloxy)-1H,2H-pyrido[1,2-f]phenanthridin-7-one;

3,4,4aR,4bS,5,6-hexahydro-9-hydroxy-11-(5-phenyl-2S-pentyloxy)-1H,2H-pyrido[1,2-f]phenanthridin-7-one;

3,4,4aS,4bR,5,6-hexahydro-9-hydroxy-11-(5-phenyl-2S-pentyloxy)-1H,2H-pyrido[1,2-f]phenanthridin-7-one;

3,4,4aS,4bR,5,6-hexahydro-9-hydroxy-11-(5-phenyl-2R-pentyloxy)-1H,2H-pyrido[1,2-f]phenanthridin-7-one;

3,4,4aS*,4bR*,5,6-hexahydro-9-hydroxy-11-(2-phenyl-1-butoxy)-1H,2H-pyrido[1,2-f]phenanthridin-7-one (two racemates);

3,4,4aS*,4bR*,5,6-hexahydro-9-hydroxy-11-(3-phenyl-1-butoxy)-1H,2H-pyrido[1,2-f]phenanthridin-7-one (two racemates);

3,4,4aS*,4bR*,5,6-hexahydro-9-hydroxy-11-(4-phenyl-1-butoxy)-1H,2H-pyrido[1,2-f]phenanthridin-7-one;

3,4,4aS*,4bR*,5,6-hexahydro-9-hydroxy-11-(1-phenyl-2-butoxy)-1H,2H-pyrido[1,2-f]phenanthridin-7-one (two racemates);

3,4,4aS*,4bR*,5,6-hexahydro-9-hydroxy-11-(4-phenyl-2-butoxy)-1H,2H-pyrido[1,2-f]phenanthridin-7-one (two racemates);

3,4,4aS*,4bR*,5,6-hexahydro-9-hydroxy-11-(5-phenyl-1-pentyloxy)-1H,2H-pyrido[1,2-f]phenanthridin-7-one;

3,4,4aS*,4bR*,5,6-hexahydro-9-hydroxy-11-[3-(3-pyridyl-1-propoxy]-1H,2H-pyrido[1,2-f]phenanthridin-7-one;

3,4,4aS*,4bR*,5,6-hexahydro-9-hydroxy-11-(1-tridecyloxy)-1H,2H-pyrido[1,2-f]phenanthridin-7-one;

3,4,4aS*,4bR*,5,6-hexahydro-9-hydroxy-11-(1-dodecyloxy)-1H,2H-pyrido[1,2-f]phenanthridin-7-one;

3,4,4aS*,4bR*,5,6-hexahydro-9-hydroxy-11-(2-decyloxy)-1H,2H-pyrido[1,2-f]phenanthridin-7-one (two racemates);

3,4,4aS*,4bR*,5,6-hexahydro-9-hydroxy-11-(4-decyloxy)-1H,2H-pyrido[1,2-f]phenanthridin-7-one (two racemates);

3,4,4aS*,4bR*,5,6-hexahydro-9-hydroxy-11-(3-octyloxy)-1H,2H-pyrido[1,2-f]phenanthridin-7-one (two racemates);

3,4,4aS*,4bR*,5,6-hexahydro-9-hydroxy-11-(4-heptyloxy)-1H,2H-pyrido[1,2-f]phenanthridin-7-one;

3,4,4aS*,4bR*,5,6-hexahydro-9-hydroxy-11-(5-methyl-2-hexyloxy)-1H,2H-pyrido[1,2-f]phenanthridin-7-one (two racemates);

3,4,4aS*,4bR*,5,6-hexahydro-9-hydroxy-11-(4-methyl-1-pentoxy)-1H,2H-pyrido[1,2-f]phenanthridin-7-one;

3,4,4aS*,4bR*,5,6-hexahydro-9-hydroxy-11-[1-(3-chlorophenyl)-1-butoxy]-1H,2H-pyrido[1,2-f]phenanthridin-7-one;

3,4,4aS*,4bR*,5,6-hexahydro-9-hydroxy-11-[1-(3-fluorophenyl)-1-propoxy]-1H,2H-pyrido[1,2-f]phenanthridin-7-one;

3,4,4aS,4bR,5,6-hexahydro-9-hydroxy-11-(2S-octyloxy)-1H,2H-pyrido[1,2-f]phenanthridin-7-one; and 3,4,4aS,4bR,5,6-hexahydro-9-hydroxy-11-(2R-octyloxy)-1H,2H-pyrido[1,2-f]phenanthridin-7-one.

EXAMPLE 34

By the procedure of Example 8, the compounds of the preceding Example are acetylated to yield the corresponding 8-acetoxy-1H-pyrrolo[1,2-f]phenanthridin-6-ones and 9-acetoxy-1H,2H-pyrido[1,2-f]phenanthridin-7-ones.

EXAMPLE 35

By the procedure of Example 9 the products of the preceding Example are hydrogenated to yield as the principle isomeric products:

8-acetoxy-1,2,3,3aS*,3bR*,4,5,6R*,7,7aR*-decahydro-6-hydroxy-10-(5-phenyl-2R*-pentyloxy)pyrrolo-1,2-f]phenanthridine and 8-acetoxy-1,2,3,3aS*,3bR*,4,5,6R*,7,7aR*-decahydro-6-hydroxy-10-(5-phenyl-2S*-pentyloxy)pyrrolo[1,2-f]phenanthridine;

8-acetoxy-1,2,3,3aR,3bS,4,5,6S,7,7aS-decahydro-6-hydroxy-10-(5-phenyl-2R-pentyloxy)pyrrolo[1,2-f]-phenanthridine;

8-acetoxy-1,2,3,3aR,3bS,4,5,6S,7,7aS-decahydro-6-hydroxy-10-(5-phenyl-2S-pentyloxy)pyrrolo[1,2-f]-phenanthridine;

8-acetoxy-1,2,3,3aS,3bR,4,5,6R,7,7aR-decahydro-6-hydroxy-10-(5-phenyl-2S-pentyloxy)pyrrolo[1,2-f]-phenanthridine;

8-acetoxy-1,2,3,3aS,3bR,4,5,6R,7,7aR-decahydro-6-hydroxy-10-(5-phenyl-2S-pentyloxy)pyrrolo[1,2-f]-phenanthridine;

9-acetoxy-2,3,4,4aS*,4bR*,5,6,7R*,8,8aR*-decahydro-7-hydroxy-11-(5-phenyl-2R*-pentyloxy)-1H-pyrido[1,2-f]phenanthridine and 9-acetoxy-2,3,4,4aS*,4bR*,5,6,7R*,8,8aR*-decahydro-7-hydroxy-11-(5-phenyl-2S*-pentyloxy)-1H-pyrido[1,2-f]phenanthridine;

9-acetoxy-2,3,4,4aR,4bS,5,6,7S,8,8aS-decahydro-7-hydroxy-11-(5-phenyl-2R-pentyloxy)-1H-pyrido[1,2-f]-phenanthridine;

9-acetoxy-2,3,4,4aR,4bS,5,6,7S,8,8aS-decahydro-7-hydroxy-11-(5-phenyl-2S-pentyloxy)-1H-pyrido[1,2-f]-phenanthridine;

9-acetoxy-2,3,4,4aS,4bR,5,6,7R,8,8aR-decahydro-7-hydroxy-11-(5-phenyl-2S-pentyloxy)-1H-pyrido[1,2-f]-phenanthridine;

9-acetoxy-2,3,4,4aS,4bR,5,6,7R,8,8aR-decahydro-7-hydroxy-11-(5-phenyl-2R-pentyloxy)-1H-pyrido[1,2-f]-phenanthridine;

9-acetoxy-2,3,4aS*,4bR*,5,6,7R*,8,8aR*-decahydro-7-hydroxy-11-(2R*-phenyl-1-butoxy)-1H-pyrido-[1,2-f]phenanthridine and 9-acetoxy-2,3,4aS*,4bR*,5,6,7R*,8,8aR*-decahydro-7-hydroxy-11-(2S*-phenyl-1-butoxy)-1H-pyrido[1,2-f]phenanthridine;

9-acetoxy-2,3,4aS*,4bR*,5,6,7R*,8,8aR*-decahydro-7-hydroxy-11-(3R*-phenyl-1-butoxy)-1H-pyrido-[1,2-f]phenanthridine and 9-acetoxy-2,3,4aS*,4bR*,5,6,7R*,8,8aR*-decahydro-7-hydroxy-11-(3S*-phenyl-1-butoxy)-1H-pyrido[1,2-f]phenanthridine;

9-acetoxy-2,3,4aS*,4bR*,5,6,7R*,8,8aR*-decahydro-7-hydroxy-11-(4-phenyl-1-butoxy)-1H-pyrido-[1,2-f]phenanthridine;

9-acetoxy-2,3,4aS*,4bR*,5,6,7R*,8,8aR*-decahydro-7-hydroxy-11-(1-phenyl-2R*-butoxy)-1H-pyrido-[1,2-f]phenanthridine and 9-acetoxy-2,3,4aS*,4bR*,5,6,7R*,8,8aR*-decahydro-7-hydroxy-11-(1-phenyl-2S*-butoxy)-1H-pyrido[1,2-f]phenanthridine;

9-acetoxy-2,3,4aS*,4bR*,5,6,7R*,8,8aR*-decahydro-7-hydroxy-11-(4-phenyl-2R*-butoxy)-1H-pyrido-[1,2-f]phenanthridine and 9-acetoxy-2,3,4aS*,4bR*,5,6,7R*,8,8aR*-decahydro-7-hydroxy-11-(4-phenyl-2S*-butoxy)-1H-pyrido[1,2-f]phenanthridine;

9-acetoxy-2,3,4aS*,4bR*,5,6,7R*,8,8aR*-decahydro-7-hydroxy-11-(5-phenyl-1-pentoxy)-1H-pyrido[1,2-f]-phenanthridine;

9-acetoxy-2,3,4aS*,4bR*,5,6,7R*,8,8aR*-decahydro-7-hydroxy-11-[3-(3-pyridyl)-1-propoxy]-1H-pyrido[1,2-f]phenanthridine;

9-acetoxy-2,3,4aS*,4bR*,5,6,7R*,8,8aR*-decahydro-7-hydroxy-11-(1-tridecyloxy)-1H-pyrido[1,2-f]phenanthridine;

9-acetoxy-2,3,4aS*,4bR*,5,6,7R*,8,8aR*-decahydro-7-hydroxy-11-(1-dodecyloxy)-1H-pyrido[1,2-f]phenanthridine;

9-acetoxy-2,3,4aS*,4bR*,5,6,7R*,8,8aR*-decahydro-7-hydroxy-11-(2R*-decyloxy)-1H-pyrido[1,2-f]phenanthridine and 9-acetoxy-2,3,4aS*,4bR*,5,6,7R*,8,8aR*-decahydro-7-hydroxy-11-(2S*-decyloxy)-1H-pyrido[1,2-f]phenanthridine;

9-acetoxy-2,3,4aS*,4bR*,5,6,7R*,8,8aR*-decahydro-7-hydroxy-11-(4R*-decyloxy)-1H-pyrido[1,2-f]phenanthridine and 9-acetoxy-2,3,4aS*,4bR*,5,6,7R*,8,8aR*-decahydro-7-hydroxy-11-(4S*-decyloxy)-1H-pyrido[1,2-f]phenanthridine;

9-acetoxy-2,3,4aS*,4bR*,5,6,7R*,8,8aR*-decahydro-7-hydroxy-11-(3R*-octyloxy)-1H-pyrido[1,2-f]phenanthridine and 9-acetoxy-2,3,4aS*,4bR*,5,6,7R*,8,8aR*-decahydro-7-hydroxy-11-(3S*-octyloxy)-1H-pyrido[1,2-f]phenanthridine;

9-acetoxy-2,3,4aS*,4bR*,5,6,7R*,8,8aR*-decahydro-7-hydroxy-11-(4-heptyloxy)-1H-pyrido[1,2-f]phenanthridine;

9-acetoxy-2,3,4aS*,4bR*,5,6,7R*,8,8aR*-decahydro-7-hydroxy-11-(5-methyl-2R*-hexyloxy)-1H-pyrido-[1,2-f]phenanthridine and 9-acetoxy-2,3,4aS*,4bR*,5,6,7R*,8,8aR*-decahydro-7-hydroxy-11-(5-methyl-2S*- 0 hexyloxy)-1H-pyrido[1,2-f]phenanthridine;

9-acetoxy-2,3,4aS*,4bR*,5,6,7R*,8,8aR*-decahydro-7-hydroxy-11-(4-methyl-1-pentoxy)-1H-pyrido-[1,2-f]phenanthridine;

9-acetoxy-2,3,4aS*,4bR*,5,6,7R*,8,8aR*-decahydro-7-hydroxy-11-[1R*-(3-chlorophenyl)-1-butoxy]-1H-pyrido[1,2-f]phenanthridine and 9-acetoxy-2,3,4aS*,4bR*, 5,6,7R*,8,8aR*-decahydro-7-hydroxy-11-[1S*-(3-chlorophenyl)-1-butoxy]-1H-pyrido[1,2-f]phenanthridine;

9-acetoxy-2,3,4aS*,4bR*,5,6,7R*,8,8aR*-decahydro-7-hydroxy-11-[1R*-(3-fluorophenyl)-1-propoxy]-1H-pyrido[1,2-f]phenanthridine and 9-acetoxy-2,3,4aS*,4bR*, 5,6,7R*,8,8aR*-decahydro-7-hydroxy-11-[1S*-(3-fluorophenyl)-1-propoxy]-1H-pyrido[1,2-f]phenanthridine;

9-acetoxy-2,3,4aS,4bR,5,6,7R,8,8aR-decahydro-7-hydroxy-11-(2R-octyl)-1H-pyrido[1,2-f]phenanthridine; and 9-acetoxy-2,3,4aS,4bR,5,6,7R,8,8aR-decahydro-7-hydroxy-11-(2S-octyl)-1H-pyrido[1,2-f]phenanthridine.

As minor products of this reduction, generally isolatable by chromatography, are isomeric products such as follows:

9-acetoxy-2,3,4aS*,4bR*,5,6,7S*,8,8aR*-decahydro-7-hydroxy-11-(5-phenyl-2R*-pentyloxy)-1H-pyrido[1,2-f]phenanthridine and 9-acetoxy-2,3,4aS*,4bR*,5,6,7S*,8,8aR*-decahydro-7-hydroxy-11-(5-phenyl-2S*-pentyloxy)-1H-pyrido[1,2-f]phenanthridine;

9-acetoxy-2,3,4aS*,4bR*,5,6,7S*,8,8aS*-decahydro-7-hydroxy-11-(5-phenyl-2R*-pentyloxy)-1H-pyrido[1,2-f]phenanthridine and 9-acetoxy-2,3,4aS*,4bR*,5,6,7S*,8,8aS*-decahydro-7-hydroxy-11-(5-phenyl-2S*-pentyloxy)-1H-pyrido[1,2-f]phenanthridine; and 9-acetoxy-2,3,4aS*,4bR*,5,6,7R*,8,8aS*-decahydro-7-hydroxy-11-(5-phenyl-2R*-pentyloxy))-1H-pyrido[1,2-f]phenanthridine and 9-acetoxy-2,3,4aS*,4bR*,5,6,7R*,8,8aS*-decahydro-7-hydroxy-11-(5-phenyl- 0 2S*-pentyloxy)-1H-pyrido[1,2-f]phenanthridine.

EXAMPLE 36

2,3,3aS*,3bR*,4,5,7,7aR*-Octahydro-8-hydroxy-10-(5-phenyl-2-pentyloxy)-1H-pyrrolo[1,2-f]phenanthridin-6-one (3b,7a-trans)

and 2,3,3aS*,3bR*,4,5,7,7aS*-Octahydro-8-hydroxy-10-(5-phenyl-2-pentyloxy)-1H-pyrrolo[1,2-f]phenanthridin-6-one (3b,7a-cis)

2,3,3aS*,3bR*,4,5-Hexahydro-8-hydroxy-10-(5-phenyl-2-pentyloxy)-1H-pyrrolo[1,2-f]phenanthridine-6-one (1.0 g.) from Example 33 is mixed with 20 ml. of THF and added dropwise via an addition funnel to a rapidly stirred solution of lithium (0.1 g.) in liquid ammonia (75 ml., distilled through potassium hydroxide pellets). The addition funnel is rinsed with tetrahydrofuran (10 ml.). The mixture is stirred for 10 minutes and then solid ammonium chloride is added to discharge the blue color. The excess ammonia is allowed to evaporate and the residue taken up in water (100 ml.) and ethyl acetate (50 ml.). The ethyl acetate layer is separated and the aqueous phase extracted with ethyl acetate (2×50 ml.). The combined extracts are washed with brine, dried (MgSO4), concentrated under reduced pressure, and the residue triturated with ether/pentane to yield title products as a mixture. If desired the mixture can be further purified by chromatography on silica gel using benzene containing a minor portion of ether as eluant.

By the same procedure, other alpha,beta-unsaturated ketones of Example 33 are reduced to mixtures of cis- and trans-fused products as follows:

2,3,3aS,3bR,4,5,7,7aR-octahydro-8-hydroxy-10-(5-phenyl-2S-pentyloxy)-1H-pyrrolo[1,2-f]phenanthridin-6-one and 2,3,3aS,3bR,4,5,7,7aS-octahydro-8-hydroxy-10-(5-phenyl-2S-pentyloxy)-1H-pyrrolo[1,2-f]phenanthridin-6-one;

2,3,3aR,3bS,4,5,7,7aR-octahydro-8-hydroxy-10-(5-phenyl-2S-pentyloxy)-1H-pyrrolo[1,2-f]phenanthridin-6-one and 2,3,3aR,3bS,4,5, 7,7aS-octahydro-8-hydroxy- 10 -(5-phenyl-2S-pentyloxy)-1H-pyrrolo[1,2-f]phenanthridin-6-one;

3,4,4aS*,4bR*,5,6,8, 8aR*-octahydro-9-hydroxy-11-(5-phenyl-2-pentyloxy)-1H, 2H-pyrido[1,2-f]phenanthridin-6-one and 3,4,4aS*,4bR*,5,6,8,8aS*-octahydro-9-hydroxy-11-(5-phenyl-2-pentyloxy)-1H,2H-pyrido[1,2-f]phenanthridin-6-one.

If desired, these isomers are separated by chromatography on silica gel.

EXAMPLE 37

8-Acetoxy-2,3,3aS*,3bR*,4,5,7,7aR*-octahydro-10-(5-phenyl-2-pentyloxy)-1H-pyrrolo[1,2-f]phenanthridin-6-one (3b,7a-trans)

and

8-Acetoxy-2,3,3aS*,3bR*,4,5,7,7aS*-octahydro-10-(5-phenyl-2-pentyloxy)-1H-pyrrolo[1,2-f]phenanthridin-6-one (3b,7a-cis)

The mixed title products of the preceding Example (222 mg.) are combined with pryidine (2.2 ml.) and acetic anhydride (2.2 ml.) and the mixture stirred for 2 hours at room temperature. The reaction mixture is quenched with ice and water and the product extracted into multiple portions of ether. The combined organic layers are washed with water and then brine, dried (MgSO4), filtered and evaporated to yield a mixture of title products. These products are separated by chromatography on silica gel using pentane-ether as eluant.

The same method is used to acetylate and separate the other cis- and trans-fused isomers of the other keto-phenols of the preceding Example.

Substitution of acetic anhydride with butyric anhydride, benzoic anhydride, glutaric anhydride or 3-morpholinopropionyl chloride hydrochloride affords the corresponding 8-butyryloxy-, 8-benzoyloxy-, 8-(4-carboxybutyryloxy)- and 8-(3-morpholinopropionyloxy)- derivatives.

EXAMPLE 38

8-Acetoxy-1,2,3,3aS*,3bR*,4,5,6,7,7aR*-decahydro-6-oximino-10-(5-phenyl-2-pentyloxy)pyrrolo[1,2-f]phenanthridine To 3b,7a-trans title product of the preceding Example (1 g.) dissolved in 5 ml. of dry pyridine is added 0.24 g. of hydroxylamine hydrochloride. After 18 hours stirring at room temperature, the title product is precipitated by dropwise addition of the reaction mixture to excess cold aqueous hydrochloric acid.

By the same procedure the other ketone esters of the preceding Example are converted to the corresponding 6-oximinopyrrolo[1,2-f]phenanthridines and 7-oximino-1H-pyrido[1,2-f]phenanthridines.

EXAMPLE 39

8-Acetoxy-6-amino-1,2,3,3aS*,3bR*,4,5,6R*,7,7aR*-decahydro-10-(5-phenyl-2-pentyloxy)pyrrolo[1,2-f]phenanthridine Title product of the preceding Example (3.2 g.) is combined with 1.5 g. 5% palladium-on-carbon catalyst and 100 ml. methanol in a pressure bottle and hydrogenated at 50 psi (3.5 kg./cm.$^2$) until substantially 1 equivalent of H$_2$ is taken up. The catalyst is recovered by filtration over diatomaceous earth, washing well with methanol. The combined filtrate and washes are evaporated in vacuo to yield the title product containing some of the 6S* isomer. If desired, the isomers are separated by chromatography on silica gel.

Substituting one of the other products of the preceding Example affords the following compounds:

8-acetoxy-6-amino-1,2,3aS*,3bR*,4,5,6S*,7,7aS*-dodecahydro-10-(5-phenyl-2-pentyloxy)pyrrolo[1,2-f]phenanthridine;

8-acetoxy-6-amino-1,2,3aS,3bR,4,5,6R,7,7aR-dodecahydro-10-(5-phenyl-2S-pentyloxy)pyrrolo[1,2-f]phenanthridine;

8-acetoxy-6-amino-1,2,3aS,3bR,4,5,6S,7,7aS-dodecahydro-10-(5-phenyl-2S-pentyloxy)pyrrolo[1,2-f]phenanthridine;

8-acetoxy-6-amino-1,2,3aR,3bS,4,5,6R,7,7aR-dodecahydro-10-(5-phenyl-2S-pentyloxy)pyrrolo[1,2-f]phenanthridine;

8-acetoxy-6-amino-1,2,3aR,3bS,4,5,6S,7,7aS-dodecahydro-10-(5-phenyl-2S-pentyloxy)pyrrolo[1,2-f]phenanthridine;

9-acetoxy-7-amino-2,3,4,4aS*,4bR*,5,6,7S*,8,8aS*-dodecahydro-10-(5-phenyl-2S-pentyloxy)-1H-pyrido-[1,2-f]phenanthridine;

9-acetoxy-7-amino-2,3,4,4aS*,4bR*,5,6,7R*,8,8aS*-dodecahydro-10-(5-phenyl-2-pentyloxy)-1H-pyrido-[1,2-f]phenanthridine;

9-acetoxy-7-amino-2,3,4,4aS*,4bR*,5,6,7S*,8,8aR*-dodecahydro-10-(5-phenyl-2-pentyloxy)-1H-pyrido-[1,2-f]phenanthridine;

9-acetoxy-7-amino-2,3,4,4aS*,4bR*,5,6,7R*,8,8aR*-dodecahydro-10-(5-phenyl-2-pentyloxy)-1H-pyrido-[1,2-f]phenanthridine;

8-butyryloxy-6-amino-1,2,3aS*,3bR*,4,5,6R*,7,7aR*-dodecahydro-10-(5-phenyl-2-pentyloxy)pyrrolo[1,2-f]phenanthridine;

8-benzoyloxy-6-amino-1,2,3aS*,3bR*,4,5,6R*,7,7aR*-dodecahydro-10-(5-phenyl-2-pentyloxy)pyrrolo[1,2-f]phenanthridine;

8-(4-carboxybutyryloxy)-6-amino-1,2,3aS*,3bR*, 4,5,6R*,7,7aR*-dodecahydro-10-(5-phenyl-2-pentyloxy)pyrrolo[1,2-f]phenanthridine; and 8-(3-morpholinopropionyloxy)-6-amino-1,2,3aS*,3bR*, 4,5,6R*,7,7aR*-dodecahydro-10-(5-phenyl-2-pentyloxy)pyrrolo[1,2-f]phenanthridine.

EXAMPLE 40

6-Acetamido-8-acetoxy-1,2,3,3aS*,3bR*,4,5,6R*,7,7aR*-decahydro-10-(5-phenyl-2-pentyloxy)pyrrolo[1,2-f]phenanthridine Title product of the preceding Example (0.75 g.) is combined with 15 ml. of pyridine and acetic anhydride (5 ml.) added dropwise with stirring over 15 minutes. After stirring for 5 hours at room temperature, the reaction mixture is concentrated, poured onto ice and extracted with ether. The organic layer is washed with water, dried (MgSO₄), filtered and reevaporated to yield title product. An equivalent amount of acetyl chloride can be substituted for the acetic anhydride, if desired.

By the same method, the other amino-esters of the preceding Example are converted to the corresponding 6-acetamidopyrrolo[1,2-f]phenanthridines and 7-acetamido-1H-pyrido[1,2-f]phenanthridines.

Substituting acetic anhydride or acetyl chloride with isobutyric anhydride, benzoyl chloride, or ethanesulfonyl chloride affords the corresponding 6- 0 isobutyramido-, 6-benzamido- and 6-ethanesulfonamido-pyrrolo[1,2-f]phenanthridines and 7-isobutyramido-, 7-benzamido- and 7-ethanesulfonamido-1H-pyrido[1,2-f]phenanthridines.

EXAMPLE 41

8-Acetoxy-1,2,3,3aS*,3bR*,4,5,6,7,7aR*-decahydro-6-methoxyimino-10-(5-phenyl-2-pehtyloxy)pyrrolo[1,2-f]phenanthridine By the procedure of Example 87 below, the 3b,7a-trans ketone of Example 37 is converted to title product.

The other acetate esters of Example 37 are likewise converted to the corresponding 6-methoxy-iminopyrrolo[1,2-f]phenanthridines and 7-methoximino-H-pyrido[1,2-f]phenanthridines.

EXAMPLE 42

6-Amino-1,2,3,3aS*,3bR*,4,5,6R*,7,7aR*-decahydro-8-hydroxy-10-(5-phenyl-2-pentyloxy)pyrrolo[1,2-f]phenanthridine By the procedure of Example 88 below, the title compound of the preceding Example is converted to title product.

The other methoxyimino-acetates of the preceding Example are likewise converted to the corresponding 6-amino-8-hydroxypyrrolo[1,2-f]phenanthridines and 7-amino-9-hydroxy-1H-pyrido[1,2-f]phenanthridines.

EXAMPLE 43

6-Acetamido-1,2,3,3aS*,3bR*,4,5,6R*,7,7aR*-decahydro-8-hydroxy-10-(5-phenyl-2-pentyloxy)pyrrolo[1,2-f]phenanthridine The title amine-phenol of the preceding Example (1 g.) is combined with 20 ml. of acetone and 1 equivalent of triethylamine. Acetyl chloride (1 equivalent), is added dropwise over 5 minutes with vigorous sitrring. After stirring an additional 15 minutes at room temperature, the reaction mixture is evaporated to dryness and taken up in ether and water. The ether layer is separated, dried (MgSO₄), filtered and evaporated to title product.

In like manner, the other amine-phenols of the preceding Example are converted to the corresponding 6-acetamido-8-hydroxypyrrolo[1,2-f]phenanthridines and 7-acetamido-9-hydroxy-1H-pyrido[1,2-f]phenanthridines.

Substituting an equivalent of acetoformic acid reagent, valeryl chloride, benzoyl chloride or methanesulfonyl chloride for acetyl chloride, affords the corresponding 6-formamido-, 6-valeramido-, 6-benzamido- and 6-methanesulfonamido-8-hydroxypyrrolo-[1,2-f]phenanthridines and 7-formamido-, 7-valeramido-, 7-benzamido- and 7-methanesulfonamido-9-hydroxy-1H-pyrido[1,2-f]phenanthridines.

Compounds of the present Example are also prepared by selective hydrolysis of compounds of the next Example using the process of Example 90 below.

EXAMPLE 44

6-Acetamido-8-acetoxy-1,2,3,3aS*,3bR*,4,5,6R*,7-,7aR*-decahydro-10-(5-phenyl-2-pentyloxy)pyrrolo[1,2-f]phenanthridine The procedure of the preceding Example is repeated, except to use at least two equivalents of triethylamine and two equivalents of acetyl chloride. The title product is isolated in like manner.

This process applied to the other amine-phenols of Example 42 affords the corresponding 6-acetamido-8-acetoxypyrrolo[1, 2-f]phenanthridines and 7-acetamido-9-acetoxy-1H-pyrido[1, 2-f]phenanthridines.

Substituting equivalent acetoformic acid reagent, butyryl chloride or benzoyl chloride affords the corresponding 6-formamido-8-formoxy-, 6-butyramido-8-butyroxy- and 6-benzamido-8-benzoyloxypyrrolo[1, 2-f]-phenanthridines and 7-formamido-9-formoxy-, 7-butyramido-9-butyroxy- and 7-benzamido-9-benzoyloxy-1H-pyrido[1, 2-f]phenanthridines.

EXAMPLE 45

6-Acetamido-8-benzoyloxy-1,2,3,3aS*,3bR*,4,5,6R*,7-,7aR*-decahydro-10-(5-phenyl-2-pentyloxy)pyrrolo[1,2-f]phenanthridine Using the title compound of Example 43 as substrate, the procedure of Example 43 is repeated, substituting 1 equivalent of benzoyl chloride for acetyl chloride. Title product is thereby produced.

In like manner the other amide-phenols of Example 43 are converted to the corresponding 6-amido-8-benzoyl- and 7-amido-9-benzoyl-derivatives.

Substituting succinic anhydride, the monoacid chloride of malonic acid or 4-dimethylaminobutyryl chloride hydrochloride for benzoyl chloride affords the corresponding 6-amido-8-(3-carboxypropionyloxy)-, 6-amido-8-(2-carboxyacetoxy)-, 6-amido-8-(4-dimethylaminobutyryloxy)-, 7-amido-9-(3-carboxypropionyloxy)-, 7-amido-9-(2-carboxyacetoxy)- and 7-amido-9-(4-dimethylaminobutyroxy)-derivatives.

EXAMPLE 46

By the procedure of Example 26, the appropriate 3-methoxy-5-substituted-aniline, prepared as set forth in U.S. Pat. No. 4,260,764, is reacted with methyl 3,7-dibromoheptanoate to yield:
methyl 2-[1-(3-methoxy-5-(5-phenyl-2-pentyl)-phenyl)-piperidin-2-yl]acetate (two racemates);
methyl 2-[1-(3-methoxy-5-(4-phenyl-1-butyl)-phenyl)-piperidin-2-yl]acetate;
methyl 2-[1-(3-methoxy-5-(4-phenyl-2-methyl-1-butyl)-phenyl)piperidin-2-yl]acetate (two racemates);
methyl 2-[1-(3-methoxy-5-(2-(3-chlorophenyl)-1-pentyl)phenyl)piperidin-2-yl]acetate (two racemates);
methyl 2-[1-(3-methoxy-5-(1-tridecyl)phenyl)piperidin-2-yl]acetate;
methyl 2-[1-(3-methoxy-5-(3-undecyl)phenyl)piperidin-2-yl]acetate (two racemates);
methyl 2-[1-(3-methoxy-5-(2-nonyl)phenyl)piperidin-2-yl]acetate (two racemates);
methyl 2-[1-(3-methoxy-5-(3-pentyl)phenyl)piperidin-2-yl]acetate;
methyl 2-[1-(3-methoxy-5-(4-phenoxy-2-butyl)phenyl)-piperidin-2-yl]acetate (two racemates);

methyl 2-[1-(3-methoxy-5-(4-benzyloxy-1-butyl)-phenyl)piperidin-2-yl]acetate;

methyl 2-[1-(3-methoxy-5-(3-(2-(4-chlorophenyl)ethoxy)-1-propyl)phenyl)piperidin-2-yl]acetate;

methyl 2-[1-(3-methoxy-5-(1-(4-(4-fluorophenyl)-1-butoxy)-3-pentyl)phenyl)piperidin-2-yl]acetate (two racemates);

methyl 2-[1-(3-methoxy-5-(4-(4-pyridyloxy)-1-butyl)-phenyl)piperidin-2-yl]acetate;

methyl 2-[1-(3-methoxy-5-(3-(1-(2-pyridyl)ethoxy)-1-propyl)phenyl)piperidin-2-yl]acetate;

methyl 2-[1-(3-methoxy-5-(4-(1-pentoxy)-2-butyl)-phenyl)piperidin-2-yl]acetate (two racemates); and methyl 2-[1-(3-methoxy-5-(1-isopropoxy-3-pentyl)-phenyl)piperidin-2-yl]acetate.

EXAMPLE 47

By the procedure of Example 27 the methyl esters of the preceding Example are hydrolyzed to the corresponding 2-[1-(3-methoxy-5-(substituted)phenyl)piperidin-2-yl]acetic acids.

EXAMPLE 48

By the procedure of Example 28, the acetic acids of the preceding Example are converted to the corresponding 3,4,4a,5-tetrahydro-7-methoxy-9-(substituted)-1H,2H-pyrido[1,2-a]quinolin-6-ones.

EXAMPLE 49

By the procedure of Example 24, the methyl ethers of the preceding Example are hydrolyzed to the corresponding 3,4,4a,5-tetrahydro-7-hydroxy-9-(substituted)-1H,2H-pyrido[1,2-a]quinolin-6-ones.

EXAMPLE 50

By the procedure of Example 5, the compounds of the preceding Example are converted to the corresponding 5-formyl-3,4,4a,5-tetrahydro-7-hydroxy-9-(substituted)-1H,2H-pyrido[1,2-a]quinolin-6-ones.

EXAMPLE 51

By the procedure of Example 6, the compounds of the preceding Example are converted to the corresponding 3,4,4aS*,5R*-tetrahydro-6-hydroxy-5-(3-oxo-1-butyl)-9-(substituted)-1H,2H-pyrido[1,2-a]quinolin-6-ones.

EXAMPLE 52

By the procedure of Example 7, the compounds of the preceding Example are converted to the corresponding 3,4,4aS*,4bR*,5,6-hexahydro-9-hydroxy-11-(substituted)-1H,2H-pyrido[1,2-f]phenanthridin-7-ones.

EXAMPLE 53

By the procedure of Example 8, the compounds of the preceding Example are acetylated to yield the corresponding 9-acetoxy-3,4,4aS*,4bR*,5,6-hexahydro-11-(substituted)-1H,2H-pyrido[1,2-f]phenanthridin-7-ones.

EXAMPLE 54

By the procedure of Example 9, the compounds of the preceding Example are hydrogenated to yield:

9-acetoxy-2,3,4,4aS*,4bR*,5,6,7R*,8,8aR*-decahydro-7-hydroxy-11-(5-phenyl-2R*-pentyl)-1H-pyrido-[1,2-f]phenanthridine and 9-acetoxy-2,3,4,4aS*,4bR*,5,6,7R*,8,8aR*-decahydro-7-hydroxy-11-(5-phenyl-2S*-pentyl)-1H-pyrido[1,2-f]phenanthridine;

9-acetoxy-2,3,4,4aS*,4bR*,5,6,7R*,8,8aR*-decahydro-7-hydroxy-11-(4-phenyl-1-butyl)-1H-pyrido-[1,2-f]phenanthridine;

9-acetoxy-2,3,4,4aS*,4bR*,5,6,7R*,8,8aR*-decahydro-7-hydroxy-11-(2R*-methyl-4-phenyl-1-butyl)-1H-pyrido[1,2-f]phenanthridine and 9-acetoxy-2,3,4,4aS*,4bR*,5,6,7R*,8,8aR*-decahydro-7-hydroxy-11-(2S*-methyl-4-phenyl-1-butyl)-1H-pyrido[1,2-f]phenanthridine;

9-acetoxy-2,3,4,4aS*,4bR*,5,6,7R*,8,8aR*-decahydro-7-hydroxy-11-[2R*-(3-chlorophenyl)-1-pentyl]-1H-pyrido[1,2-f]phenanthridine and 9-acetoxy-2,3,4,4aS*,4bR*,5,6,7R*,8,8aR*-decahydro-7-hydroxy-11-[2S*-(3-chlorophenyl)-1-pentyl]-1H-pyrido[1,2-f]phenanthridine;

9-acetoxy-2,3,4,4aS*,4bR*,5,6,7R*,8,8aR*-decahydro-7-hydroxy-11-(1-tridecyl)-1H-pyrido[1,2-f]phenanthridine;

9-acetoxy-2,3,4,4aS*,4bR*,5,6,7R*,8,8aR*-decahydro-7-hydroxy-11-(3R*-undecyl)-1H-pyrido[1,2-f]phenanthridine and 9-acetoxy-2,3,4,4aS*,4bR*,5,6,7R*, 8,8aR*-decahydro-7-hydroxy-11-(3S*-undecyl)-1H-pyrido[1,2-f]phenanthridine;

9-acetoxy-2,3,4,4aS*,4bR*,5,6,7R*,8,8aR*-decahydro-7-hydroxy-11-(2R*-nonyl)-1H-pyrido[1,2-f]phenanthridine and 9-acetoxy-2,3,4,4aS*,4bR*,5,6,7R*,8,8aR*-decahydro-7-hydroxy-11-(2S*-nonyl)-1H-pyrido-[1,2-f]phenanthridine;

9-acetoxy-2,3,4,4aS*,4bR*,5,6,7R*,8,8aR*-decahydro-7-hydroxy-11-(3-pentyl)-1H-pyrido[1,2-f]phenanthridine;

9-acetoxy-2,3,4,4aS*,4bR*,5,6, 7R*,8,8aR*-decahydro-7-hydroxy-11-(4-phenoxy-2R*-butyl)-1H-pyrido-[1,2-f]phenanthridine and 9-acetoxy-2,3,4,4aS*,4bR*,5,6,7R*,8,8aR*-decahydro-7-hydroxy-11-(4-phenoxy-2S*-butyl)-1H-pyrido[1,2-f]phenanthridine;

9-acetoxy-2,3,4,4aS*,4bR*,5,6,7R*,8,8aR*-decahydro-7-hydroxy-11-(4-benzyloxy-1-butyl)-1H-pyrido-[1,2-f]phenanthridine;

9-acetoxy-2,3,4,4aS*,4bR*,5,6,7R*,8,8aR*-decahydro-7-hydroxy-11-[3-(2-(4-chlorophenyl)ethoxy)-1-propyl]-1H-pyrido[1,2-f]phenanthridine;

9-acetoxy-2,3,4,4aS*,4bR*,5,6,7R*,8,8aR*-decahydro-7-hydroxy-11-[1-(4-(4-fluorophenyl)-1-butoxy)-3R*-pentyl]-1H-pyrido[1,2-f]phenanthridine and 9-acetoxy -2,3,4,4aS*,4bR*,5,6,7R*,8,8aR*-decahydro-7-hydroxy-11-[1-(4-(4-fluorophenyl)-1-butoxy)-3S*-pentyl]-1H-pyrido[1,2-f]phenanthridine;

9-acetoxy-2,3,4,4aS*,4bR*,5,6,7R*,8,8aR*-decahydro-7-hydroxy-11-[4-(4-pyridyloxy)-1-butyl]-1H-pyrido[1,2-f]phenanthridine;

9-acetoxy-2,3,4,4aS*,4bR*,5,6,7R*,8,8aR*-decahydro-7-hydroxy-11-[3-(1-(2-pyridyl)ethoxy)-1-propyl]-1H-pyrido[1,2-f]phenanthridine;

9-acetoxy-2,3,4,4aS*,4bR*,5,6,7R*,8,8aR*-decahydro-7-hydroxy-11-[4-(1-pentoxy)-2R*-butyl]-1H-pyrido[1,2-f]phenanthridine and 9-acetoxy-2,3,4,4aS*, 4bR*,5,6,7R*,8,8aR*-decahydro-7-hydroxy-11-[4-(1-pentoxy)-2S*-butyl]-1H-pyrido[1,2-f]phenanthridine; and 9-acetoxy-2,3,4,4aS*,4bR*,5,6,7R*,8,8aR*-decahydro-7-hydroxy-11-(1-isopropoxy-3-pentyl)-1H-pyrido-[1,2-f]phenanthridine.

EXAMPLE 55

By the procedure of Example 36, the compounds of Example 52 are reduced to Li/NH₃ to yield the corresponding 3,4,4aS*,4bR*,5,6,8,8aR*-octahydro-9-hydroxy-11-(substituted)-1H,2H-pyrido[1,2-f]phenanthridine-7-ones (4b,8a-trans isomer) and 3,4,4aS*,4bR*,5,6,8,8aS*-octahydro-9-hydroxy-11-(substituted)-1H,2H-pyrido-[1,2-f]phenanthridin-7-ones (4b,8a-cis isomer).

EXAMPLE 56

By the procedure of Example 37, the compounds of the preceding Example are acylated to produce various 9-acyloxy-3,4,4aS*,4bR*,5,6,8,8aR*-octahydro-11-(substituted)-1H,2H-pyrido[1,2-f]phenanthridin-7-ones (4b,8a-trans) and 9-acyloxy-3,4,4aS*,4bR*,5,6,8,8aS*-octahydro-11-(substituted)-1H,2H-pyrido[1,2-f]phenanthridin-7-ones (4b,8a-cis).

EXAMPLE 57

By the procedure of Example 84 below, the ketones of the previous Example are reduced with sodium borohydride. The 4b,8a-trans isomers yield primarily the corresponding equatorial alcohols, viz., 9-acyloxy-2,3,4,4aS*,4bR*,5,6,7R*,8,8aR*-decahydro-7-hydroxy-11-(substituted)-1H-pyrido[1,2-f]phenanthridines.

EXAMPLE 58

By the procedure of Example 87 below, the equatorial 4b,8a-trans acetate esters of Example 56 are reacted with methoxyamine to produce the corresponding 9-acetoxy-2,3,4,4aS*,4bR*,5,6,7,8,8aR*-decahydro-7-methoxyimino-11-(substituted)-1H-pyrido-[1,2-f]phenanthridines.

EXAMPLE 59

By the procedure of Example 88 below, the methoxy oximes of the preceding Example are reduced with hydride to yield the corresponding 7-amino-2,3,4,4aS*,4bR*,5,6,7R*,8,8aR*-decahydro-7-hydroxy-11-(substituted)-1H-pyrido[1,2-f]phenanthridines.

EXAMPLE 60

By the procedure of Example 89 below, the amine-phenols of the preceding Example are acetylated to 7-acetamido-9-acetoxy-2,3,4,4aS*,4bR*,5,6,7R*-8,8aR*-decahydro-11-(substituted)-1H-pyrido[1,2-f]phenanthridines.

EXAMPLE 61

By the procedure of Example 90 below, the phenolic acetates of the preceding Example are hydrolyzed to 7-acetamido-2,3,4,4aS*,4bR*,5,6,7R*,8,8aR*-decahydro-9-hydroxy-11-(substituted)-1H-pyrido[1,2-f]phenanthridines.

EXAMPLE 62

8-Benzyloxy-2,3,3aS*,3bR*,4,5,7,7aR*-octahydro-10-(5-phenyl-2-pentyloxy)-1H-pyrrolo[1,2-f]phenanthridin-6-one 2,3,3aS*,3bR*, 4,5,7,7aR*-octahydro-8-hydroxy-10-(5-phenyl-2-pentyloxy)-1H-pyrrolo[1, 2-f]phenanthridine-6-one of Example 36 (5 g.) in 40 ml. of dimethylformamide is added under nitrogen to a suspension of one equivalent of NaH in 40 ml. of dimethylformamide. The mixture is stirred for 0.5 hours at room temperature. Benzyl bromide (1.1 equivalents) is added dropwise over 15 minutes. After stirring for 16 hours at room temperature, the reaction mixture is filtered and stripped to yield the title product. Any residual salt is removed by taking the reaction product up in ethyl acetate, filtering and reevaporating to dryness. Alternatively the mixed cis- and trans-fused isomers of Example 36 are benzylated, and the resulting benzylated isomers separated by chromatography on silica gel.

By the same method the other phenols of Example 36, as well as the phenols of Example 55 are converted to the corresponding 8-benzyloxy-1H-pyrrolo[1,2-f]phenanthridin-6-ones and 9-benzyloxy-1H,2H-pyrido-[1,2-f]phenanthridin-6-ones.

EXAMPLE 63

8-Benzyloxy-1,2,3,3aS*,3bR*,4,5,6R*,7,7aR*-decahydro-6-hydroxy-10-(5-phenyl-2-pentyloxy)pyrrolo[1,2-f]phenanthridine By the procedure of Example 57, the title ketone of the preceding Example is reduced with sodium borohydride to yield primarily the title product, viz., the equatorial alcohol. In like manner, the other benzyl ethers of the preceding Example are reduced to the corresponding 8-benzyloxy-6-hydroxypyrrolo[1,2-f]phenanthridines and 9-benzyloxy-7-hydroxy-1H-pyrido[1,2-f]phenanthridines.

EXAMPLE 64

6-Acetoxy-8-benzyloxy- u 1,2,3,3aS*,3bR*,4,5,6R*,7,7aR*-decahydro-10-(5-phenyl-2-pentyloxy)pyrrolo[1,2-f]phenanthridine By the procedure of Example 8, the title compound of the preceding Example is acetylated to yield title product.

In like manner, the other benzyl ether-alcohols of the preceding Example are acetylated to yield the corresponding 6- and 7-acetates.

EXAMPLE 65

6-Acetoxy-1,2,3,3aS*,3bR*,4,5,6R*,7,7aR*-decahydro-8-hydroxy-10-(5-phenyl-2-pentyloxy)pyrrolo[1,2-f]phenanthridine By the procedure of Example 39, the title of the preceding Example is hydrogenated to yield the present product.

In like manner, other compounds of the preceding Example are converted to:
6-acetoxy-1,2,3,3aS,3bR,4,5,6R,7,7aR-decahydro-8-hydroxy-10-(5-phenyl-2R-pentyloxy)pyrrolo[1,2-f]phenanthridine;
6-acetoxy-1,2,3,3aR,3bS,4,5,6R,7,7aR-decahydro-8-hydroxy-10-(5-phenyl-2R-pentyloxy)pyrrolo[1,2-f]phenanthridine; and various
7-acetoxy-2,3,4,4aS*,4bR*,5,6,7R*,8,8aR*-8-hydroxy-11-(substituted)-1H-pyrido[1,2-f]phenanthridines.

EXAMPLE 66

8-Benzyloxy-1,2,3,3aS*,3bR*,4,5,6,7,7aR*-decahydro-6-methoxyimino-10-(5-phenyl-2-pentyloxy)pyrrolo[1,2-f]phenanthridine By the procedure of Example 87 below, the title ketone of Example 62 is converted to the present compound.

In like manner, the other ketones of Example 62 are converted to the corresponding 8-benzyloxy-6-methoxyiminopyrrolo[1,2-f]phenanthridines and 9-benzyloxy-7-methoxyimino-1H-pyrido[1,2-f]phenanthridines.

EXAMPLE 67

6-Amino-8-benzyloxy-1,2,3,3aS*,3bR*,4,5,6R*,7,7aR*-decahydro-10-(5-phenyl-2-pentyloxy)pyrrolo[1,2-f]phenanthridine By the procedure of Example 88, title product of the preceding Example is reduced to present title product.

In like manner, the other methoxyimines of the preceding Example are converted to the corresponding 6-amino-8-benzyloxypyrrolo[1,2-f]phenanthridines and 7-amino-9-benzyloxy-1H-pyrido[1,2-f]phenanthridines.

EXAMPLE 68

8-Benzyloxy-6-(1-propanesulfonamido)-1,2,3,3aS*,3bR*,4,5,6R*,7,7aR*-decahydro-10-(5-phenyl-2-pentyloxy)pyrrolo[1,2-f]phenanthridine By the procedure of Example 89, the title amine of the preceding Example is reacted with a slight excess of 1-propanesulfonyl chloride to yield the present title product.

Substitution of 1-propanesulfonyl chloride with 2-propanesulfonyl chloride, benzoyl chloride or isobutyryl chloride affords the corresponding 8-benzyloxy-6-(2-propanesulfonamido)-, 8-benzyloxy-6-benzamido- and 8-benzyloxy-6-isobutyramido-pyrrolo[1,2-f]phenanthridines.

By the same method the other amines of the preceding Example are converted to the corresponding 8-benzyloxy-6-acylaminopyrrolo[1,2-f]phenanthridines and 9-benzyloxy-7-acylamino-1H-pyrido[1,2-f]phenanthridines.

EXAMPLE 69

1,2,3,3aS*,3bR*,4,5,6R*,7,7aR*-Decahydro-8-hydroxy-6-(1-propanesulfonamido)-10-(5-phenyl-2-pentyloxy)pyrrolo[1,2-f]phenanthridine By the procedure of Example 9, the title benzyloxy compound of the preceding Example is hydrogenolyzed to yield present title product.

By the same procedure, other benzyl ethers of the previous Example are converted to
6-(1-propanesulfonamido)-, 6-(2-propanesulfonamido)-, 6-benzamido- and 6-isobutyramido-1,2,3,3aS,3bR,4,5,6R,7,7aR-decahydro-8-hydroxy-10-(5-phenyl-2R-pentyloxy)pyrrolo[1,2-f]phenanthridine;
6-(1-propanesulfonamido)-, 6-(2-propanesulfonamido)-, 6-benzamido- and 6-isobutyramido-1,2,3,3aR,3bS,4,5,6R,7,7aR-decahydro-8-hydroxy-10-(5-phenyl-2R-pentyloxy)pyrrolo[1,2-f]phenanthridine; and various
6-(1-propanesulfonamido)-, 6-(2-propanesulfonamido)-, 6-benzamido- and 6-isobutyramido-2,3,4,4aS*,4bR*,5,6,7R*,8,8aR*-decahydro-9-hydroxy-11-(substituted)-1H-pyrido[1,2-f]phenanthridines.

EXAMPLE 70 trans-1-(3,5-Dimethoxyphenyl)-2-nitroethylene

A solution of 3,5-dimethoxybenzaldehyde (34.5 g., 0.208 mole) and nitromethane (12.69 g., 0.208 mole) in 40 ml. of MeOH was cooled to 0° under $N_2$. A solution was prepared by dissolving NaOH (8.43 g., 0.211 mole) in 10 ml. of $H_2O$ then diluting to 20 ml. with ice-water. This solution was then added dropwise to the methanol mixture. After 15 minutes the reaction was diluted with ice-$H_2O$ and added slowly to a solution of 40 ml. concentrated HCl in 60 ml. $H_2O$. The resulting precipitate (44 g.) was filtered and recrystallized from methanol to give 28.6 g. of product, m.p. 132°; reported, J. Org. Chem. 27, p. 376 (1962), m.p. 133.5-134.5.

EXAMPLE 71

4-(2,5-Dimethoxyphenyl)-5-nitrocyclohexene

A steel bomb was charged with product of the preceding Example (28.6 g., 0.134 mole), butadiene (20 g., 0.378 mole), toluene (40 ml.) and a trace of hydroquinone. The bomb was cooled to −78° under $N_2$ atmosphere and sealed rapidly. The sealed tube was heated at 100° for 48 hours. The contents of the bomb were concentrated in a stream of $N_2$ and recrystallized from MeOH to give 29.8 g. of product, m.p. 80.5°-82°; reported, J. Org. Chem. 27, p. 376 (1962), m.p. 73°-75°; $^1$H—NMR (CDCl$_3$) includes 6.40 (3H, s) 5.75 (2H, s), 4.95 (1H, m) and 3.75 (6H, s) ppm.

EXAMPLE 72

6-(3,5-Dimethoxyphenyl)-3-cyclohexen-1-one

The Nef reaction was applied to the product of the preceding Example (28.7 g., 0.109 mole) in 163.5 ml. of ethanol, using 131 ml. of concentrated HCl and the procedure of Wildman, J. Org. Chem. 17, p. 588 (1952) for 6-phenyl-3-cyclohexen-1-ones. After recrystallization from isopropyl ether, there was obtained 23.6 g. of product, m.p. 60°-62°; reported, J. Org. Chem. 27, p. 376 (1962), 65.5°-66.6°.

EXAMPLE 73

2-(3,5-Dimethoxyphenyl)cyclohexanone

Method A

Product of the preceding Example (23.6 g.) in 300 ml. of ethanol was hydrogenated over 3 g. of 10% Pd/C at room temperature and 40 psig to yield, after recrystallization from isopropyl ether, 17 g. of title product, m.p. 61°-62°; reported, J. Org. Chem. 27, p. 376 (1962), 62.5°-63°.

Method B

The method is a modification of that employed by Arnold et al., J. Am. Chem. Soc., 72, 3154 (1950), for preparation of 2-phenylcyclopentanone. To an ice-cold stirred solution of 3,5-dimethoxyphenyl magnesium bromide, prepared from 25.5 g. of magnesium and 226 g. (1.04 mole) 3,5-dimethoxybromobenzene in 800 ml. dry ethyl ether, is added a solution of 130.5 g. 2-chlorocyclohexanone in 400 ml. dry ethyl ether. The ether is removed by distillation and is replaced with 200 ml. dry xylene. The resulting mixture is heated at 150°-170° C. for two hours, cooled, poured onto ice and diluted with 6N hydrochloric acid. The acidified mixture is extracted with benzene. The organic phase is washed with water and then dilute sodium hydroide solution, and dried over anhydrous sodium sulfate. The solvents were evaporated in vacuo and the product purified by distillation in vacuo.

EXAMPLE 74

1-(Carbomethoxymethylene)-2-(3,5-dimethoxyphenyl)-cyclohexane

To a suspension of NaH (3.9 g., 0.0814 mole of 50% in oil) in 500 ml. of THF was added dropwise a solution of trimethyl phosphonoacetate (16.2 g., 0.089 mole) in 50 ml. of THF. After stirring 10–15 minutes at room temperature, the ketone product of the preceding Example (17.4 g., 0.074 mole) in 100 ml. of THF was added in one portion. The reaction was heated at 70° for 3 hours, then cooled to 0°. Acetic acid (5.4 g.) was added and the reaction was diluted with H2O (1 liter) and extracted with ethyl acetate. The extract was dried over Na2SO4 and evaporated to give 22 g. of crude product. Recrystallization from isopropyl ether gave 20.4 g. of product, m.p. 80°–81°; $^1$H—NMR (CDCl3) includes 6.34 (3H, s), 5.20 (1H, s), 3.80 (6H, s) and 3.60 (3H, s) ppm.

EXAMPLE 75

1-(Carboxymethylene)-2-(3,5-dimethoxyphenyl)cyclohexane and

2-[2-(3,5-Dimethoxyphenyl)cyclohexen-1-yl]acetic Acid

Method A

To a solution of the ester product of the preceding Example (20 g.) in a mixture of 100 ml. MeOH, 50 ml. H2O and 50 ml. THF was added 42 ml. of 5N NaOH. The reaction was heated on a steam bath for 3 hours then diluted with ice-water. A solution of 1N HCl (220 ml.) was added and the reaction mixture was extracted with ethyl acetate, dried over Na2SO4 and evaporated to give 20 g. of crude product. Recrystallization from CH2Cl2/ether gave 16.7 g. of the carboxymethylene product, m.p. 154°–156°; $^1$H—NMR (CDCl3) 6.30 (3H, s), 3.70 (6H, s), 5.15 (1H, s), 10.90 (1H, s) ppm.

Method B

Product prepared according to the preceding Example (68.8 g., 0.230 mole) was combined with 350 ml. of methanol and 142.4 ml. (0.711 mole) of 5N NaOH and the mixture heated to reflux for 1.3 hours. The reaction mixture was cooled to room temperature, quenched with 62.2 ml. of concentrated HCl and water and extracted 3×with ethyl acetate. The combined organic extracts were washed with brine, dried over MgSO4, filtered and stripped of solvents. The residue was recrystallized from CH2Cl2/ether to yield the carboxymethylene product in two crops: 37.6 g., m.p. 155°–158°; 13.3 g., m.p. 156°–158°. The mother liquor from the second crop was evaporated to solids (13.5 g.) which on trituration with isopropyl ether gave a further 4 g. of the carboxymethylene product, m.p. 152°–156° C., ir (KBr) 1675 cm$^{-1}$. The isopropyl ether triturate was evaporated to yield the nonconjugated substituted acetic acid product [9 g., ir (KBr) 1705 cm$^{-1}$].

EXAMPLE 76

2S*-[2R*-(3,5-Dimethoxyphenyl)cyclohexyl]acetic Acid

Lithium metal (832 mg., 0.119 mole) was added to a solution of the alpha,beta-unsaturated acid of the preceding Example (15 g., 0.054 mole) in 1 liter liquid NH3 and 200 ml. THF at -33°. A blue color was allowed to form and persist for 2 minutes. The reaction was then quenched by addition of 15 g. of NH4Cl. The NH3 was evaporated under a stream of N2. Water (200 ml.) was added and the solution was acidified to pH 3.5 by addition of 6N HCl. The aqueous layer was then extracted with CH2Cl2 and the organic layer was dried over Na2SO4 and evaporated to give 15 g. of crude product which was triturated with hexane and filtered to give 14 g. of product, m.p. 110°–111.5°; $^1$H—NMR (CDCl3) includes 2.16 (2H, dd, J=14.7, 2.3), 2.17 (1H, td, J=11, 3), 1.90 (1H, d, J=14.6) ppm.

EXAMPLE 77

2,3,4,4aR*,10,10aS*-Hexahydro-6,8-dimethoxy-1H-phenanthren-9-one

Trifluoroacetic anhydride (20 ml.) was added dropwise to a solution of the acid of the preceding Example (14.7 g.) in trifluoroacetic acid (28 ml.) at 0°. After stirring for 15 minutes, the volatiles were evaporated and the residue was taken up in CH2Cl2 and washed with H2O, 20% NaHCO3 and brine, then dried over Na2SO4 and evaporated to give 15.7 g. of crude product which was recrystallized from ether to give 12.5 g. of product, m.p. 110°–111°; MS exact mass calcd. for C16H20O3: 260.3358; found: 260.1404.

EXAMPLE 78

2,3,4,4aR*,10,10aS*-Hexahydro-6,8-dihydroxy-1H-phenanthren-9-one

A solution of the ketone of the preceding Example (12.3 g.) in a mixture of 220 ml. acetic acid and 220 ml. of 48% HBr was heated at 100° in a N2 atmosphere for 36 hours. The volatiles were evaporated under reduced pressure and the residue was purified by chromatography on 120 g. of silica gel eluting with ethyl acetate to give 12 g. of material, m.p. 189°–200°. Recrystallization from ethyl acetate/CHCl3 gave 10 g. of product, m.p. 200°–201°; $^1$H—NMR (acetone-d6) includes 6.50-6.10 (2H, m) and 13.0 (1H, s); M.S. exact mass calcd. for C14H16O3: 232.2816; found: 232.1097.

EXAMPLE 79

2,3,4,4aR*,10,10aS*-Hexahydro-8-hydroxy-6-(5-phenyl-2-pentyloxy)-1H-phenanthren-9-one A mixture of the phenol of the preceding Example (9.9 g., 0.043 mole) and K2CO3 (7.1 g., 0.103 mole) in 120 ml. DMF was heated at 70° for 30 minutes. 5-Phenyl-2-pentyl mesylate (13.55 g., 0.056 mole) in 10 ml. of DMF was added in one portion and the mixture was heated in a nitrogen atmosphere at 80° overnight. The reaction was diluted with ice-H2O and extracted with ethyl acetate. The extract was dried over Na2SO4 and evaporated to give 21 g. of crude product. Chromatography on 750 g. of silica gel with CHCl3/hexane (50/50), then with CHCl3, and finally 20% ether in CHCl3 gave 14 g. of product as an oil; $^1$H—NMR (CDCl3) includes 13.10 (1H, s), 7.30 (5H, s), 6.50-6.20 (2H, m), 4.45 (1H, m), 1.40 (3H, d) ppm. As a result of the asymmetric carbon introduced in the 5-phenyl-2-pentyloxy side chain, this product is a mixture of two racemic compounds, i.e. two racemates or two racemic pairs.

By the same procedure, the appropriate mesylate esters are reacted with the phenol of the preceding Example to yield 2,3,4,4aR*,10,10aS*-hexahydro-8-hydroxy-6-(4-phenyl-1-butoxy)-1H-phenanthren-9-one;

2,3,4,4aR*,10,10aS*-hexahydro-8-hydroxy-6-[3-(3-pyridyl)-1-propoxy)-1H-phenanthren-9-one;

2,3,4,4aR*,10,10aS*-hexahydro-8-hydroxy-6-(2-decyloxy)-1H-phenanthren-9-one (two racemates); and 2,3,4,4aS,10,10aR-hexahydro-8-hydroxy-6-(5-phenyl-2R-pentyloxy)-1H-phenanthren-9-one and 2,3,4,4aR,10,10aS-hexahydro-8-hydroxy-6-(5-phenyl-2R-pentyloxy)-1H-phenanthren-6-one.

EXAMPLE 80

10-Formyl-2,3,4,4aR*,10,10aR*-hexahydro-8-hydroxy-6-(5-phenyl-2-pentyloxy)-1H-phenanthren-9-one In a 1 liter flask fitted with magnetic stirrer, condenser and $N_2$ inlet was placed 50% NaH in mineral oil (5.52 g., 0.115 mole) and washed with two portions of hexane to remove the mineral oil. In sequence, ether (800 ml.), title product of the preceding Example (12.5 g., 0.033 mole), and, dropwise, ethyl formate (41.2 ml.), followed by 4 drops of ethanol. The reaction mixture was refluxed for 3 hours, cooled to room temperature, stirred for 64 hours at room temperature then poured over crushed ice, acidified with 115 ml. 1 N HCl, and extracted with 3 portions of ethyl acetate. The combined organic extracts were washed with brine, dried over $MgSO_4$, filtered and stripped of solvents. The residue was chromatographed on 200 g. silica gel eluting with $CHCl_3$ and monitoring by tlc [$R_f$0.9 (20:1 $CHCl_3$:isopropyl ether)]. On evaporation, product fractions gave 10.1 g. of title product as an oil, $^1H$—NMR ($CDCl_3$) includes 7.20 (5H, s), 6.20 (2H, m), 12.30 (1H, s), 13.60 (1H, d) ppm. The product is a mixture of two racemates. No additional asymmetery is introduced by introduction of the 5-formyl group because of the tendency of this group to exist, together with the 6-ketone, in an enolic form.

By the same method, other ketones of the preceding Example are converted to:
10-formyl-2,3,4,4aR*,10,10aR*-hexahydro-8-hydroxy-6-(4-phenyl-1-butoxy)-1H-phenanthren-9-one;
10-formyl-2,3,4,4aR*,10,10aR*-hexahydro-8-hydroxy-6-[3-(3-pyridyl)-1-propoxy]-1H-phenanthren-9-one;
10-formyl-2,3,4,4aR*,10,10aR*-hexahydro-8-hydroxy-6-(2-decyloxy)-1H-phenanthren-9-one (two racemates);
10-formyl-2,3,4,4aR,10,10aR-hexahydro-8-hydroxy-6-(5-phenyl-2R-pentyloxy)-1H-phenanthren-9-one; and
10-formyl-2,3,4,4aS,10,10aS-hexahydro-8-hydroxy-6-(5-phenyl-2R-pentyloxy)-1H-phenanthren-9-one.

EXAMPLE 81

2,3,4,4aR*,10S*,10aR*-Hexahydro-8-hydroxy-10-(3-oxo-1-butyl)-6-(5-phenyl-2-pentyloxy)-1H-phenanthren-9-one Title product of the preceding Example (10.0 g., 24.6 mmoles) was combined with 40 ml. methanol, 18 ml. THF, methyl vinyl ketone (3.4 g., 49.2 mmoles) and triethylamine (0.829 g., 8.2 mmoles) and stirred under nitrogen for 16 hours, at which time an additional 0.329 g. (3.25 mmoles) of triethylamine and 1.34 g. of methyl vinyl ketone (19 mmoles) were added. After stirring for an additional 24 hours, the reaction mixture was stripped of solvents in vacuo, and the residue taken up in ethyl acetate, washed 2× with 10% $Na_2CO_3$, 1× with $H_2O$ and 1× with brine, dried over $MgSO_4$, filtered and evaporated to crude product. To ensure complete deformylation, the crude product was taken into 150 ml. methanol/30 ml. THF at 0°. $K_2CO_3$ (0.859 g.) was added and the mixture stirred for 2 hours, filtered and stripped of solvent. Chromatography of the residual oil on 200 g. of silica gel, eluting with 4-1 $CHCl_3$:ether and monitoring by tlc gave purified title product, as a mixture of at least two racemates. The relative stereochemistry at C-5 has not been established—while both diastereomeric pairs may be present, it is most likely that relative stereochemistry at C-5 is S*, and is thus unchanged in the process of the next Example. The yield of title product was 8.4 g. [oil; $R_f$0.45 (6:1 hexane:ether), 0.1 elongated ($CHCl_3$); $^1H$—NMR ($CDCl_3$) includes 13.20 (1H, s), 7.20 (5H, s), 6.30 (2H, m), 2.10 (3H, s), 1.30 (3H, d) ppm].

By the same method, the other 5-formyl derivatives of the preceding Example are converted to:
2,3,4aR*,10S*,10aR*-hexahydro-8-hydroxy-10-(3-oxo-1-butyl)-6-(4-phenyl-1-butoxy)-1H-phenanthren-9-one;
2,3,4aR*,10S*,10aR*-hexahydro-8-hydroxy-10-(3-oxo-1-butyl)-6-[3-(3-pyridyl)-1-propoxy]-1H-phenanthren-9-one;
2,3,4aR*,10S*,10aR*-hexahydro-8-hydroxy-10-(3-oxo-1-butyl)-6-(2-decyloxy)-1H-phenanthren-9-one;
2,3,4aR,10S,10aR-hexahydro-8-hydroxy-10-(3-oxo-1-butyl)-6-(5-phenyl-2R-pentyloxy)-1H-phenanthren-9-one; and
2,3,4aS,10R,10aS-hexahydro-8-hydroxy-10-(3-oxo-1-butyl)-6-(5-phenyl-2R-pentyloxy)-1H-phenanthren-9-one.

EXAMPLE 82

2,3,4,4aS*,4bS*, 5,6,12bR*-Octahydro-9-hydroxy 11-(5-phenyl-2-pentyloxy)-1H-triphenylen-7-one Under nitrogen, KOH (42.5 g., 0.759 mole) was dissolved with stirring in 380 ml. of methanol. Title product of the preceding Example (8.4 g., 18.8 mmoles) was added and the stirred reaction mixture heated at 50° C. for 1 hour, cooled and stirred at room temperature for 16 hours, cooled to 0° C. and neutralized by the addition of 45.6 g. (0.76 mole) of glacial acetic acid. Volatile materials were removed by evaporation and the residue dissolved in ethyl acetate, washed 2 × water and 1 × brine, dried over $MgSO_4$, filtered and stripped of solvent. The latter residue was chromatographed on 200 g. of silica gel, eluting first with $CHCl_3$ and then with 4:1 $CHCl_3$ ether and monitoring by tlc. Clean fractions were combined and evaporated to yield 7.0 g. of title product, a mixture of two racemates, m.p. 160°-165°; $R_f$0.3 (2:1 $CHCl_3$:ether); ir ($CHCl_3$) 1585, 1560 cm$^{-1}$. A sample triturated with ether gave m.p. 189°-190°.

By the same method, the other ketones of the preceding Example are cyclized, affording:
2,3,4,4aS*,4bS*,5,6,12bR*-octahydro-9-hydroxy-11-(4-phenyl-1-butoxy)-1H-triphenylen-7-one;
2,3,4,4aS*,4bS*,5,6,12bR*-octahydro-9-hydroxy-11-[3-(3-pyridyl)-1-propoxy]-1H-triphenylen-7-one;
2,3,4,4aS*,4bS*,5,6,12bR*-octahydro-9-hydroxy-11-(2-decyloxy)-1H-triphenylen-7-one;
2,3,4,4aS,4bS,5,6,12bR-octahydro-9-hydroxy-11-(5-phenyl-2R-pentyloxy)-1H-triphenylen-7-one; and
2,3,4,4aR,4bR,5,6,12bS-octahydro-9-hydroxy-11-(5-phenyl-2R-pentyloxy)-1H-triphenylen-7-one.

EXAMPLE 83

9-Acetoxy-2,3,4,4a S*,4bS*,5,6,8,8aR*,12bR*-decahydro-11-(5-phenyl-2-pentyloxy)-1H-triphenylen-7-one and

9-Acetoxy-2,3,4,4aS*,4bS*,5,6,8,8aS*,12bR*-decahydro-11-(5-phenyl-2-pentyloxy)-1H-triphenylene-7-one The title ketone of the preceding Example (2.66 g., 6.2 mmoles) was slurried in a mixture of 150 ml. of THF and 300 ml. of liquid NH₃ at −33°. Sufficient Li metal (in excess of 98 mg., 14 mmoles) was added in portions until the blue color persisted for 4 minutes. The reaction was then quenched by the addition of 2.6 g. of NH₄Cl (48 mmole) and the ammonia removed by evaporation under a stream of nitrogen. Water and ethyl acetate were added, the pH was adjusted to 6, and the aqueous layer separated and extracted with additional ethyl acetate. The organic layers were combined, washed with brine, dried over MgSO₄, filtered and stripped of solvent to yield a mixture of intermediate trans (4bS*,8aR*) and cis (4bS*,8aS*) phenolic ketones (2.7 g.). The mixed product was taken up in 50 ml. $CH_2Cl_2$. Triethylamine (5 g.) and acetic anhydride (2.5 g.) were added and the solution allowed to stand at room temperature under nitrogen for 16 hours. Solvent was removed by evaporation and the residue was taken into ether, washed with water and then brine, dried over MgSO₄, filtered and stripped of solvent to yield 3.3 g. of a mixture of title products. The mixture was chromatographed on 150 g. silica gel, gradiently eluted with 1:9, 1:4 and 1:1 ether:hexane. There was isolated 0.6 g. of the less polar, trans (4bS*,8aR*) fused product [oil; ¹H—NMR (CDCl₃) includes 7.20 (5H, s), 6.65 (1H, d), 6.40 (1H, d), 3.35 (2H, m), 2.30 (3H, s) ppm]. Additional mixed product from the column was rechromatographed on 400 g. of fresh silica gel, gradiently eluting with 1:20, 1:10, 1:5 and 2:3 ether:hexane, yielding an additional 0.7 g. of the less polar product, and 0.3 g. of the more polar cis (4bS*,8aS*) fused product [oil; ¹H—NMR (CDCl₃) includes 7.20 (5H, s), 6.65 (1H, d), 6.40 (1H, d), 2.30 (3H, s). Each of these products is a pair of racemates.

By the same method the following compounds are prepared from other ketones of the preceding Example 9-acetoxy-2,3,4,4aS*,4bS*,5,6,8,8aR*,12bR*-decahydro-11-(4-phenyl-1-butoxy)-1H-triphenylene-7-one (4b,8a-trans) and the corresponding 4b,8a-cis compound;

9-acetoxy-2,3,4,4aS*,4bS*,5,6,8,8aR*,12bR*-decahydro-11-[3-(3-pyridyl)-1-propoxy]-1H-triphenylen-7-one (4b,8a-trans) and the corresponding 4b,8a-cis compounds;

9-acetoxy-2,3,4,4aS*,4bS*,5,6,8,8aR*,12bR*-decahydro-11-(2-decyloxy)-1H-triphenylen-7-one (4b,8a-trans, two racemates) and the corresponding 4b,8a-cis compounds;

9-acetoxy-2,3,4,4aS,4bS,5,6,8,8aR,12bR-decahydro-11-(5-phenyl-2R-pentyloxy)-1H-triphenylene-7-one (4b,8a-trans) and the corresponding 4b,8a-cis isomer; and 9-acetoxy-2,3,4aR,4bR,5,6,8,8aR,12bS-decahydro-11-(5-phenyl-2R-pentyloxy)-1H-triphenylen-7-one (4b,8a-cis) and the corresponding 4b,8a-trans isomer.

Substituting an equivalent amount of benzoic anhydride, succinic anhydride or 5-(4-methylpipera-zino)-valeroyl chloride hydrochloride for the acetic anhydride in this Example affords the corresponding 9-benzoate, 9-(3-carboxypropionate) and 9-[5-(4-methyl-piperazino)valerate] esters.

EXAMPLE 84

9-Acetoxy-1,2,3,4,4aS*,4bS*,5,6,7R*,8,8aR*,12bR*-dodecahydro-7-hydroxy-11(5-phenyl-2-pentyloxy)-triphenylene and 9-Acetoxy-1,2,3,4,4aS*,4bS*,5,6,7S*,8,8aR*,12bR*-dodecahydro-7-hydroxy-11-(5-phenyl-2-pentyloxy)-triphenylene The less polar 4bS*,8aR*-ketone, i.e. the 4b,8a-trans ketone of the preceding Example (0.6 g.), was dissolved in 60 ml. of ethanol at 0°. NaBH₄ (0.276 g.) was added in one portion. After 10 minutes at 0° the reaction was poured into 130 ml. 5% CH₃CO₂H and 300 ml. of ether. After stirring for 10 minutes the ether layer was separated, washed 2×H₂O, 1× saturated NaHCO₃ and 1 ×brine, dried over MgSO₄, filtered and evaporated to a mixture of title products (0.66 g.). The latter were separated by chromatography on 60 g. silica gel gradiently eluting with 1:1 ether:hexane, 3:1 ether:hexane and finally ether. The less polar 7S* product eluted first [30 mg., m/e: 476 (parent), 458 (p-H₂O), 270 (base)]. The more polar, equatorial 7R* alcohol eluted secondarily [0.57 g., m/e: 476 (parent), 288 (base)]. Each of these products is a mixture of two racemates.

By the same method, other compounds of the preceding Example are converted primarily to the equatorial alcohols, as follows:

9-acetoxy-1,2,3,4,4aS*,4bS*,5,6,7R*,8,8aR*,12bR*-dodecahydro-7-hydroxy-11-(4-phenyl-1-butoxy)-triphenylene;

9-acetoxy-1,2,3,4,4aS*,4bS*,5,6,7R*,8,8aR*,12bR*-dodecahydro-7-hydroxy-11-[3-(3-pyridyl)-1-propoxy]-triphenylene;

9-acetoxy-1,2,3,4,4aS*,4bS*,5,6,7R*,8,8aR*,12bR*-dodecahydro-7-hydroxy-11-(2-decyloxy)triphenylene (two racemates);

9-acetoxy-1,2,3,4,4aS,4bS,5,6,7R,8,8aR,12bR-dodecahydro-7-hydroxy-11-(5-phenyl-2R-pentyloxy)triphenylene; and 9-acetoxy-1,2,3,4,4aR,4bR,5,6,7R,8,8aR,12bS-dodecahydro-7-hydroxy-11-(5-phenyl-2R-pentyloxy)triphenylene.

Lesser quantities of the axial alcohols are formed, e.g.:

9-acetoxy-1,2,3,4,4aS,4bS,5,6,7S,8,8aR,12bR-dodecahydro-7-hydroxy-11-(5-phenyl-2R-pentyloxy)triphenylene; and 9-acetoxy-1,2,3,4,4aR,4bR,5,6,7S,8,8aR,12bS-dodecahydro-7-hydroxy-11-(5-phenyl-2R-pentyloxy)triphenylene.

The corresponding 9-benzoate, 9-(3-carboxy-propionate), and 9-[5-(4-methylpierazino)valerate|esters are also obtained from appropriate esters of the preceding Example by the method of this Example.

The method of Example 8, substituting acetic anhydride with benzoic anhydride, butyric anhydride or acetoformic acid reagent as appropriate, affords the corresponding 7-acetate, 7-benzoate, 7-butyrate and 7-formate ester derivatives of the compounds of the present Example.

EXAMPLE 85

9-Acetoxy-1,2,3,4,4aS*,4bS*,5,6,7R*,8,8aS*,12bR*-dodecahydro-7-hydroxy-11-(5-phenyl-2-pentyloxy)-triphenylene and 9-Acetoxy-1,2,3,4,4aS*,4bS*,5,6,7S*,8,8aS*,12bR*-dodecahydro-7-hydroxy-11-(5-phenyl-2-pentyloxy)-triphenylene The more polar 4bS*,8aS*-ketone, i.e., the 4b,8a-cis ketone of Example 83 (150 mg.) was dissolved in 15 ml. of ethanol at −10°. Sodium borohydride (70 mg.) was added in one portion. The mixture was stirred at −10° for 15 minutes and then poured into 35 ml. of 5% $CH_3CO_2H$ and 100 ml. of ether. The ether layer was separated, washed 2×$H_2O$, 1× saturated $NaHCO_3$ and 1× brine, dried over $MgSO_4$, filtered and evaporated to a mixture of title products (150 mg.). Title products were separated by chromatography on 15 g. silica gel, using 1:1 ether:hexane as eluant. This less polar 7R*-isomer eluted firstly [10 mg.; m/e: 476 (parent), 270 (base)], and the more polar 7S*-isomer secondly [80 mg.; m/e: 476 (parent), 416 (p-60), 330 (p-146), 270 (base)]. Each of these products is a mixture of two racemates. EXAMPLE 86

1,2,3,4,4aS*,4bS*,5,6,7R*,8,8aR*,12bR*-Dodecahydro-7,11-dihydroxy-(5-phenyl-2-pentyloxy)triphenylene The 7R* acetate of Example 84 (250 mg.) was dissolved in 6 ml. of methanol and diluted with 2 ml. of 1N NaOH. After standing 1 hour at room temperature, 1N HCl(2 ml.) was added and the reaction mixture extracted with ether. The ether extract was dried over $MgSO_4$, filtered and evaporated to yield title product (242 mg.). Recrystallization from diisopropyl ether gave purified title product (200 mg.; m.p. 158° ).

EXAMPLE 87

9-Acetoxy-1,2,3,4,4aS*,4bS*,5,6,7,8,8aR*,12bR*-dodecahydro-7-methoxyimino-11-(5-phenyl-2-pentyloxy)triphenylene The less polar 4bS*,8Ra*-ketone, i.e. the 4b,8a-trans ketone of Example 83 (770 mg., 1.6 mmoles) was dissolved in 20 ml. 1:1 ethanol:pyridine and cooled to 0°. Methoxyamine hydrochloride (142 mg., 1.7 mmoles) was added in one portion. After stirring for one hour at 0° C., the title product was isolated by evaporation of the reaction mixture. The crude product was taken into ether, washed with $H_2O$, dried over $MgSO_4$, filtered and reevaporated [770 mg.; $^1H$—NMR ($CDCl_3$) includes 7.10 (s, 5H, phenyl), 6.65 (d, 1H, aromatic), 6.35 (d, H, aromatic), 3.80 (s, 3H, $NOCH_3$) 2.25 ppm (s, 3H, $COCH_3$)]. This product is a mixture of two racemates.

EXAMPLE 88

7-Amino-1,2,3,4aS*,4bS*,5,6,7R*,8,8aR*,12bR*-dodecahydro-9-hydroxy-11-(5-phenyl-2-pentyloxy)-triphenylene Sodium borohydride (605 mg., 16 mmoles) was suspended in 16 ml. of THF. $F_3CCO_2H$ (1.82 g., 16 mmoles) in 2 ml. THF was added over 10 minutes at 20°. The mixture was cooled to 0° and methoxyimino compound of the preceding Example (770 mg., 1.6 mmoles) in 2 ml. of THF added. The reaction mixture was stirred for 1 hour at 0° C., 2 hours at room temperature and 2 hours at reflux. Excess reagent was destroyed by adding ice and water. The quenched reaction mixture was concentrated and extracted with methylene chloride. The organic extract was dried over $MgSO_4$, filtered and evaporated to yield the title amine (750 mg.), a mixture of two racemates.

EXAMPLE 89

7-Acetamido-9-acetoxy-1,2,3,4,4aS*,4bS*,5,6,7R*,8,8aR*,12bR*-dodecahydro-11-(5-phenyl-2-pentyloxy)-triphenylene The amine-alcohol of the preceding Example (750 mg.) was treated with a mixture of acetic anhydride (5 ml.) and pyridine (15 ml.) for 2 hours on a steam bath. The reaction mixture was stripped of volatiles and the residue taken up in ether, washed with water, dried and reevaporated to yield crude title product (850 mg.). The product was purified by chromatography on 100 g. silica gel, initially eluting with 1:1 hexane:ether, then ether, then 1:1 ethyl acetate:ether and finally ethyl acetate, monitoring by silica gel TLC (ether eluant, $R_f$ of product 0.1), and discarding less polar by-products. Clean product fractions were combined and evaporated to yield purified title product [620 mg.; $^1H$—NMR ($CDCl_3$): 7.15 (s, 5H, phenyl), 6.70 (d, 1H, aromatic), 6.30 (d, 1H, aromatic), 5.80 (d, 1H, N$\underline{H}$), 2.35 (s, 3H, $CO_2C\underline{H}_3$), 1.90 ppm (s, 3H, $NHCOC\underline{H}_3$)], a mixture of two racemates.

EXAMPLE 90

7-Acetamido-1,2,3,4aS*,4bS*,5,6,7R*,8,8aR*,12bR*-dodecahydro-9-hydroxy-11-(5-phenyl-2-pentyloxy)-triphenylene The acetate-acetamide of the preceding Example (620 mg., 1.2 mmoles) was dissolved in 20 ml. of methanol and cooled to −5°. 1N Sodium hydroxide (1.2 ml.) was added and the mixture stirred at 0° for 0.5 hour. 1N Hydrochloric acid (1.3 ml.) was added and the mixture stripped of solvents. The residue was taken up in ether, washed with water and then brine, dried over $MgSO_4$, filtered and reevaporated to yield title product (470 mg., m.p. 185°–186°), triturated with a small amount of ether [340 mg.; m.p. 195°–196°; m/e: 475 (parent), 270 (base)]. Evaporation of mother liquor gave 100 mg., chromatographed on 5 g. of silica gel with 1:1 ether:ethyl acetate as eluant gave 95 mg., which on recrystallization from diisopropyl ether gave an additional 35 mg. of purified title product (m.p. 192°–194°). This product is a mixture of two racemates.

EXAMPLE 91

7-Benzamido-9-benzoyloxy-1,2,3,4,4aS*,4bS*,5,6,7R*,8,8aR*,12bR*-dodecahydro-11-(5-phenyl-2-pentyloxy)triphenylene The amine-alcohol of Example 88 (165 mg.) was dissolved in a mixture of 3 ml. of pyridine and 1 ml. of benzoyl chloride. After standing at room temperature for four hours, the reaction mixture was diluted with ether, washed with water, dried over $MgSO_4$, filtered and evaporated to yield crude title product (380 mg.).

EXAMPLE 92

7-Benzamido-1,2,3,4,4aS*,4bS*,5,6,7R*,8,8aR*,12bR*-dodecahydro-9-hydroxy-11-(5-phenyl-2-pentyloxy)-triphenylene The benzamide-benzoate of the preceding Example (120 mg.) was hydrolyzed in methanol containing 0.5 ml. of 1N sodium hydroxide at room temperature for 5 hours. 1N Hydrochloric acid (0.5 ml.) was added and methanol removed by stripping. The aqueous residue was extracted with ethyl acetate. The extract was stripped of solvent to yield crude title product (70 mg.), purified by chromatography on 4 g. of silica gel to yield purified title product [44 mg.; m/e 537 (parent), 270 (base)].

EXAMPLE 93

2S*-[2S*-(2,5-Dimethoxyphenyl)-1-cyclohexyl]acetic Acid

2-[2-(3,5-Dimethoxyphenyl)cyclohexen-1-yl]acetic acid (3 g.) from Example 75 was hydrogenated in ethanol, otherwise according to Example 39. The catalyst was recovered by filtration and the filtrate saturated with dry hydrogen chloride, converting the title product to the ethyl ester, isolated by stripping the solvent. The crude ester was chromatographed on 300 g. of silica gel with 9:1 hexane:ether as eluant. Less polar impurities (20 mg.) were discarded and 2 g. of purified ethyl ester recovered from intermediate fractions. The ester was hydrolyzed with 4 ml. of 5N NaOH and 10 ml. of methanol gently refluxed for 1.5 hours. The reaction mixture was cooled, acidifed with dilute HCl and extracted with ethyl acetate. The organic extract was washed with brine, dried (MgSO4), filtered and stripped of solvent. Recrystallization of the residue from isopropyl ether gave purified title product (1.1 g., m.p. 139°–141° C.).

EXAMPLE 94

2,3,4aS*,10,10aS*-Hexahydro-6,8-dimethoxy-1H-phenanthren-9-one

By the method of Example 77, the acid of the preceding Example is cyclized to title product.

EXAMPLE 95

2,3,4aS*,10,10aS*-Hexahydro-6,8-dihydroxy-1H-phenanthren-9-one

By the method of Example 78, the dimethyl ether of the preceding Example is hydrolyzed to the title product.

EXAMPLE 96

2,3,4aS*,10,10aS*-Hexahydro-8-hydroxy-6-(5-phenyl-2-pentyloxy)-1H-phenanthren-9-one By the method of Example 79, the bis-phenol of the preceding Example is alkylated to title product.

By the same method the bis-phenol of the preceding Example is reacted with 5-phenyl-2S-pentyl mesylate to produce 2,3,4aS,10,10aS-hexahydro-8-hydroxy-6-(5-phenyl-2R-pentyloxy)-1H-phenanthren-9-one and 2,3,4aR,10,10aR-hexahydro-8-hydroxy-6-(5-phenyl-2R-pentyloxy)-1H-phena nthren-9-one.

EXAMPLE 97

10-Formyl-2,3,4aS*,10,10aR*-hexahydro-8-hydroxy-6-(5-phenyl-2-pentyloxy)-1H-phenanthren-9-one By the method of Example 80, the title product of the preceding Example is formylated to yield the title 10-formyl derivative.

By the same method the other compounds of the preceding Example are converted to:
10-formyl-2,3,4aR,10,10aS-hexahydro-8-hydroxy-6-(5-phenyl-2R-pentyloxy)-1H-phenanthren-9-one; and 10-formyl-2,3,4aS,10,10aR-hexahydro-8-hydroxy-6-(5-phenyl-2R-pentyloxy)-1H-phenanthren-9-one.

EXAMPLE 98

2,3,4,4aS*,10S*,10aR*-Hexahydro-8-hydroxy-10-(3-oxo-1-butyl)-6-(5-phenyl-2-pentyloxy)-1H-phenanthren-9-one and 2,3,4,4aS*,10R*,10aR*-Hexahydro-8-hydroxy-10-(3-oxo-1-butyl)-6-(5-phenyl-2-pentyloxy)-1H-phenanthren-9-one By the procedure of Example 81, title product of the preceding Example is reacted with methyl vinyl ketone and deformylated to produce a mixture of title products.

By the same method, the other products of the preceding Example are converted to:
2,3,4aR,10S, 10aS-hexahydro-8-hydroxy-10-(3-oxo-1-butyl)-6-(5-phenyl-2R-pentyloxy)-1H-phenanthren-9-one and 2,3,4aR,10R, 10aS-hexahydro-8-hydroxy-10-(3-oxo-1-butyl)-6-(5-phenyl-2R-pentyloxy)-1H-phenanthren-9-one; and
2,3,4aS,10R, 10aR-hexahydro-8-hydroxy-10-(3-oxo-1-butyl)-6-(5-phenyl-2R-pentyloxy)-1H-phenanthren-9-one and 2,3,4aS,10S, 10aR-hexahydro-8-hydroxy-10-(3-oxo-1-butyl)-6-(5-phenyl-2R-pentyloxy)-1H-phenanthren-9-one.

EXAMPLE 99

By the procedure of Example 82, the products of the preceding Example are cyclized, producing:
2,3,4aS*,4bS*,5,6,12bS*-octahydro-9-hydroxy-11-(5-phenyl-2-pentyloxy)-1H-triphenylen-7-one 4a,4b-trans);
2,3,4aS*,4bR*,5,6,12bS*-octahydro-9-hydroxy-11-(5-phenyl-2-pentyloxy)-1H-triphenylen-7-one 4a,4b-cis);
2,3,4aS,4bS,5,6,12bS-octahydro-9-hydroxy-11-(5-phenyl-2R-pentyloxy)-1H-triphenylen-7-one;
2,3,4aS,4bR,5,6,12bS-octahydro-9-hydroxy-11-(5-phenyl-2R-pentyloxy)-1H-triphenylen-7-one;
2,3,4aR,4bR,5,6,12bR-octahydro-9-hydroxy-11-(5-phenyl-2R-pentyloxy)-1H-triphenylen-7-one; and
2,3,4aR,4bS,5,6,12bR-octahydro-9-hydroxy-11-(5-phenyl-2R-pentyloxy)-1H-triphenylen-7-one.

EXAMPLE 100

By the procedure of Example 83, the following compounds are obtained by Li/NH3 reduction of the compounds of the preceding Example to preferentially yield 4b,8a-trans-fused compounds as follows:
2,3,4,4aS*,4bS*,5,6,8,8aR*, 12bS*-decahydro-9-hydroxy-11-(5-phenyl-2-pentyloxy)-1H-triphenylene-7-one (4a,4b-trans, 4b,8a-trans);
2,3,4,4aS*,4bR*,5,6,8,8aS*, 12bS*-decahydro-9-hydroxy-11-(5-phenyl-2-pentyloxy)-1H-triphenylen-7-one (4a,4b-cis, 4b,8a-trans);
2,3,4,4aS,4bS,5,6,8,8aR, 12bS-decahydro-9-hydroxy-11-(5-phenyl-2R-pentyloxy)-1H-triphenylen-7-one;
2,3,4,4aS,4bR,5,6,8,8aS,12bS-decahydro-9-hydroxy-11-(5-phenyl-2R-pentyloxy)-1H-triphenylen-7-one;
2,3,4,4aR,4bR,5,6,8,8aS,12bR-decahydro-9-hydroxy-11-(5-phenyl-2R-pentyloxy)-1H-triphenylen-7-one; and
2,3,4,4aR,4bS,5,6,8,8aR,12bR-decahydro-9-hydroxy-11-(5-phenyl-2R-pentyloxy)-1H-triphenylen-7-one.

EXAMPLE 101

By the procedure of Example 83, the compounds of the preceding Example are acetylated to yield the corresponding 9-acetoxy derivatives.

EXAMPLE 102

By the procedure of Example 84, the compounds of the preceding Example are reduced with sodium borohydride to yield preferentially the equatorial alcohols:

9-acetoxy-1,2,3,4,4aS*,4bS*,5,6,7R*,8,8aR*,12bS*-dodecahydro-7-hydroxy-11-(5-phenyl-2-pentyloxy)triphenylene;

9-acetoxy-1,2,3,4,4aS*,4bR*,5,6,7S*,8,8aS*,12bS*-dodecahydro-7-hydroxy-11-(5-phenyl-2-pentyloxy)triphenylene, alternatively named 9-acetoxy-1,2,3,4,4aR*,4bS*, 5,6,7R*,8,8aR*,12bR*-dodecahydro-7-hydroxy-11-(5-phenyl-2-pentyloxy)triphenylene;

9-acetoxy-1,2,3,4,4aS,4bS,5,6,7R,8,8aR,12bS-dodecahydro-7-hydroxy-11-(5-phenyl-2R-pentyloxy)triphenylene;

9-acetoxy-1,2,3,4aS,4bR,5,6,7S,8,8aS,12bS-dodecahydro-7-hydroxy-11-(5-phenyl-2R-pentyloxy)triphenylene;

9-acetoxy-1,2,3,4aR,4bR,5,6,7S,8,8aS,12bR-dodecahydro-7-hydroxy-11-(5-phenyl-2R-pentyloxy)triphenylene; and 9-acetoxy-1,2,3,4aR,4bS,5,6,7R,8,8aR,12bR-dodecahydro-7-hydroxy-11-(5-phenyl-2R-pentyloxy)triphenylene.

EXAMPLE 103

2-[3-Methoxy-5-(2-undecyl)]cyclohexanone

Method A

By the sequential methods of Examples 70 to 73, 3-methoxy-5-(2-undecyl)benzaldehyde is converted to title product.

Method B

By method B of Example 73, 3-bromo-5-(2-undecyl)anisole is converted to title product.

Using one or the other of these methods, the following compounds are prepared from the corresponding 3-methoxy-5-(substituted)benzaldehyde or 3-bromo-(substituted)anisole:

2-[3-methoxy-5-(5-phenyl-2-methyl-1-pentyl)]cyclohexanone;

2-[3-methoxy-5-(5-phenyl-2R-methyl-1-pentyl)]cyclohexanone;

2-[3-methoxy-5-(1-(1-heptyloxy)-2-propyl)]cyclohexanone;

2-[3-methoxy-5-(5-(2-chlorophenyl)-1-hexyl)]cyclohexanone;

2-[3-methoxy-5-(7-(3-fluorophenyl)-3-heptyl)]cyclohexanone; and

2-[3-methoxy-5-(8-(3-pyridyl)-1-octyl)]cyclohexanone.

EXAMPLE 104

2S*-[2R*-[3-Methoxy-5-(2-undecyl)]cyclohexyl]acetic Acid

Following the procedures of Examples 74 to 76, title compound of the preceding Example is converted to title product.

In like manner other compounds of the preceding Example are converted to:

2S*-[2R*-[3-methoxy-5-(5-phenyl-2-methyl-1-pentyl)-]cyclohexyl]acetic acid;

2S-[2R-[3-methoxy-5-(5-phenyl-2R-methyl-1-pentyl)-]cyclohexyl]acetic acid and 2R-[2S-[3-methoxy-5-(5-phenyl-2R-methyl-1-pentyl)]cyclohexyl]acetic acid;

2S*-[2R*-[3-methoxy-5-[5-(2-chlorophenyl)-1-hexyl)-]cyclohexyl]acetic acid;

2S*-[2R*-[3-methoxy-5-(7-(3-fluorophenyl)-3-heptyl)-]cyclohexyl]acetic acid; and 2S*-[2R*-[3-methoxy-5-(8-(3-pyridyl)-1-octyl)]cyclohexyl]acetic acid.

If desired, these acids are resolved at this stage via conversion to diastereomeric optically active amine salts. For example, the following compounds are so obtained:

2S-[2R-[3-methoxy-5-(8-(3-pyridyl)-1-octyl)]cyclohexyl]acetic acid; and

2R-[2S-[3-methoxy-5-(8-(3-pyridyl)-1-octyl)]cyclohexyl]acetic acid.

EXAMPLE 105

2S*-[2R*[3-Hydroxy-5-(2-undecyl)]cyclohexyl]acetic Acid

By the procedure of Example 24, title compound of the preceding Example is converted to title product.

In like manner, the other anisoles of the preceding Example are converted to the corresponding phenols.

EXAMPLE 106

By the sequence and procedures of Examples 80-85, compounds of the preceding Example are converted, for example, to:

9-acetoxy-1,2,3,4,4aS*,4bS*,5,6,7R*,8,8aR*,12bR*-dodecahydro-7-hydroxy-11-(2-undecyl)triphenylene (two racemates);

9-acetoxy-1,2,3,4,4aS,4bS,5,6,7R,8,8aR,12bR-dodecahydro-7-hydroxy-11-(5-phenyl-2R-methyl-1-pentyl)triphenylene;

9-acetoxy-1,2,3,4,4aS,4bS,5,6,7S,8,8aS,12bR-dodecahydro-7-hydroxy-11-(5-phenyl-2R-methyl-1-pentyl)triphenylene;

9-acetoxy-1,2,3,4,4aR,4bR,5,6,7S,8,8aS,12bS-dodecahydro-7-hydroxy-11-(5-phenyl-2S-methyl-1-pentyl)triphenylene;

9-acetoxy-1,2,3,4,4aR,4bR,5,6,7R,8,8aR,12bS-dodecahydro-7-hydroxy-11-(5-phenyl-2S-methyl-1-pentyl)triphenylene;

9-acetoxy-1,2,3,4,4aS*,4bS*,5,6,7R*,8,8aR*,12bR*-dodecahydro-7-hydroxy-11-[5-(2-chlorophenyl)-1-hexyl]triphenylene;

9-acetoxy-1,2,3,4,4aS*,4bS*,5,6,7R*,8,8aR*,12bR*-dodecahydro-7-hydroxy-11-[7-(3-fluorophenyl)-3-heptyl]triphenylene;

9-acetoxy-1,2,3,4,4aS,4bS,5,6,7R,8,8aR,12bR-dodecahydro-7-hydroxy-11-[8-(3-pyridyl)-1-octyl]triphenylene; and 9-acetoxy-1,2,3,4,4aR,4bR,5,6,7R,8,8aR,12bS-dodecahydro-7-hydroxy-11-[8-(3-pyridyl)-1-octyl]triphenylene.

EXAMPLE 107

2-(3,5-Dimethoxyphenyl)cyclopentanone

The procedure of Example 73, Method B, substituting an equivalent of cyclopentanone for cyclohexanone produces the title product.

Substituting the appropriate Grignard reagent for 3,5-dimethoxyphenyl magnesium bromide in like manner produces the following compounds:
2-[3-methoxy-5-(2-hexyl)phenyl]cyclopentanone;
2-[3-methoxy-5-(3-ethyl-1-pentyl)phenyl]cyclopentanone;
2-[3-methoxy-5-(5-phenyl-1-hexyl)phenyl]cyclopentanone;
2-[3-methoxy-5-(6-phenyl-2-hexyl)phenyl]cyclopentanone;
2-[3-methoxy-5-[6-(4-chlorophenyl-2-hexyl]phenyl]cyclopentanone;
2-[3-methoxy-5-[5-(4-fluorophenyl)-2-pentyl]phenyl]cyclopentanone;
2-[3-methoxy-5-[6-(4-pyridyl)-2-hexyl]phenyl]cyclopentanone;
2-[3-methoxy-5-[1-(1-heptyloxy)-2-propyl]phenyl]cyclopentanone; and
2-[3-methoxy-5-[2-(2-phenylethoxy)-1-propyl]phenyl]cyclopentanone.

EXAMPLE 108

2S*-[2R*-(3,5-dihydroxyphenyl)cyclopentyl]acetic Acid

By the sequence and procedures of Examples 74–76, the title product of the preceding Example is converted to present title product.

In like manner, the other cyclopentanones of the preceding Example are converted to the corresponding 2S*-[2R*-(3-methoxy-5-substituted phenyl)]acetic acids.

If desired, the compounds of this Example are resolved at this point in the synthesis by the usual method of separating diastereomeric salts formed with an optically active amine. Exemplary of compounds so prepared are:
2S-[2R-(3,5-dihydroxyphenyl)cyclopentyl]acetic acid; and
2R-[2S-[3-methoxy-5-(3-ethyl-1-pentyl)phenyl]cyclopentyl]acetic acid.

EXAMPLE 109

3,3aS*,4,9bR*-Tetrahydro-6,8-dihydroxy-1H,2H-cyclopenta[a]naphthalen-5-one

By the sequence and procedures of Examples 77 and 78, the title compound of the preceding Example is converted to the title product of the present Example.

In like manner the other compounds of the preceding Example are converted to the corresponding:
3,3aS*,4,9bR*-tetrahydro-6-hydroxy-8-(substituted)-1H,2H-cyclopenta[a]naphthalen-5-ones;
3,3aS,4,9bR-tetrahydro-6,8-dihydroxy-1H,2H-cyclopenta[a]naphthalen-5-one; and
3,3aS,4,9bR-tetrahydro-6-hydroxy-8-(3-ethyl-1-pentyl)-1H,2H-cyclopenta[a]naphthalen-5-one.

EXAMPLE 110

3,3aS*,4,9bR*-Tetrahydro-6-hydroxy-8-(5-phenyl-2-pentyloxy)-1H,2H-cyclopenta[a]naphthalen-5-one By the procedure of Example 79, title product of the preceding Example is converted to title product of the present Example.

Substituting the appropriate mesylate ester for 5-phenyl-2-pentyl mesylate the following compounds are likewise prepared:
3,3aS*,4,9bR*-tetrahydro-6-hydroxy-8-(1-dodecyloxy)-1H,2H-cyclopenta[a]naphthalen-5-one; and
3,3aS*,4,9bR*-tetrahydro-6-hydroxy-8-[1-(3-fluorophenyl)-1-propoxy]-1H,2H-cyclopenta[a]naphthalen-5-one.

Substituting the optically active bis-phenol of the preceding Example and the appropriate optically active mesylate ester of opposite configuration, the following compounds are prepared:
3,3aS,4,9bR-tetrahydro-6-hydroxy-8-(4-phenyl-2R-butyloxy)-1H,2H-cyclopenta[a]naphthalen-5-one;
3,3aS,4,9bR-tetrahydro-6-hydroxy-8-(6-phenyl-2R-hexyloxy)-1H,2H-cyclopenta[a]naphthalen-5-one; and
3,3aS,4,9bR-tetrahydro-6-hydroxy-8-(2R-octyloxy)-1H,2H-cyclopenta[a]naphthalen-5-one.

EXAMPLE 111

By the sequence and procedures of Examples 80–84, monophenolic compounds of the preceding Examples are converted to:
8-acetoxy-2,3,3aS*,3bS*,4,5,6R*,7,7aR*,11bR*-decahydro-6-hydroxy-10-(2-hexyl)-1H-cyclopenta[1]phenanthrene (two racemates);
8-acetoxy-2,3,3aS*,3bS*,4,5,6R*,7,7aR*,11bR*-decahydro-6-hydroxy-10-(3-ethyl-1-pentyl)-1H-cyclopenta[1]phenanthrene;
8-acetoxy-2,3,3aS*,3bS*,4,5,6R*,7,7aR*,11bR*-decahydro-6-hydroxy-10-(5-phenyl-1-hexyl)-1H-cyclopenta[1]phenanthrene (two racemates);
8-acetoxy-2,3,3aS*,3bS*,4,5,6R*,7,7aR*,11bR*-decahydro-6-hydroxy-10-(6-phenyl-2-hexyl)-1H-cyclopenta[1]phenanthrene (two racemates);
8-acetoxy-2,3,3aS*,3bS*,4,5,6R*,7,7aR*,11bR*-decahydro-6-hydroxy-10-[5-(4-fluorophenyl)-2-pentyl]-1H-cyclopenta[1]phenanthrene (two racemates);
8-acetoxy-2,3,3aS*,3bS*,4,5,6R*,7,7aR*,11bR*-decahydro-6-hydroxy-10-[6-(4-pyridyl)-2-hexyl]-1H-cyclopenta[1]phenanthrene (two racemates);
8-acetoxy-2,3,3aS*,3bS*,4,5,6R*,7,7aR*,11bR*-decahydro-6-hydroxy-10-[1-(1-heptyloxy)-2-propyl]-1H-cyclopenta[1]phenanthrene (two racemates);
8-acetoxy-2,3,3aS*,3bS*,4,5,6R*,7,7aR*,11bR*-decahydro-6-hydroxy-10-[2-(2-phenylethoxy)-1-propyl]-1H-cyclopenta[1]phenanthrene (two racemates);
8-acetoxy-2,3,3aS*,3bS*,4,5,6R*,7,7aR*,11bR*-decahydro-6-hydroxy-10-(5-phenyl-2-pentyloxy)-1H-cyclopenta[1]phenanthrene (two racemates);
8-acetoxy-2,3,3aS*,3bS*,4,5,6R*,7,7aR*,11bR*-decahydro-6-hydroxy-10-(1-dodecyloxy)-1H-cyclopenta[1]phenanthrene;
8-acetoxy-2,3,3aS*,3bS*,4,5,6R*,7,7aR*,11bR*-decahydro-6-hydroxy-[1-(3-fluorophenyl)-1-propoxy]-1H-cyclopenta[1]phenanthrene (two racemates);
8-acetoxy-2,3,3aS,3bS,4,5,6R,7,7aR,11bR-decahydro-6-hydroxy-10-(3-ethyl-1-pentyl)-1H-cyclopenta[1]phenanthrene;
8-acetoxy-2,3,3aS,3bS,4,5,6R,7,7aR,11bR-decahydro-6-hydroxy-10-(4-phenyl-2R-butoxy)-1H-cyclopenta[1]phenanthrene;
8-acetoxy-2,3,3aS,3bS,4,5,6R,7,7aR,11bR-decahydro-6-hydroxy-10-(6-phenyl-2R-hexyloxy)-1H-cyclopenta[1]phenanthrene; and
8-acetoxy-2,3,3aS,3bS,4,5,6R,7,7aR,11bR-decahydro-6-hydroxy-(2R-octyloxy)-1H-cyclopenta[1]phenanthrene.

EXAMPLE 112

9-Benzyloxy-2,3,4,4aS*,4bS*,5,6,8,8aR*,12bR*-decahydro-11-(5-phenyl-2-pentyl-oxy)-1H-triphenylene-7-one By the procedure of Example 62, the intermediate phenolic ketones of Example 83 are converted to title 4bS*,8aR*-trans-fused product together with the corresponding 4bS*,8aS*-cis-fused compounds, separable by chromatography on silica gel.

By the same procedure, the analogous phenolic ketone intermediates of Example 111 are converted to:
8-benzyloxy-3,3aS*,3bS*,4,5,7,7aR*,11bR*-octahydro-10-(5-phenyl-2-pentyloxy)-1H,2H-cyclopenta[1]phenanthrene;
8-benzyloxy-3,3aS,3bS,4,5,7,7aR,11bR-octahydro-10-(5-phenyl-2R-hexyloxy)-1H,2H-cyclopenta[1]phenanthrene; and
8-benzyloxy-3,3aS,3bS,4,5,7,7aR,11bR-octahydro-10-(3-ethyl-1-pentyl)-1H,2H-cyclopenta[1]phenanthrene.

EXAMPLE 113

By the sequence and procedures of Examples 87-89, compounds of the preceding Example are converted to:
7-acetamido-9-benzyloxy-1,2,3,4,4aS*,4bS*,5,6,7R*,8,8aR*,12bR*-dodecahydro-11-(5-phenyl-2-pentyloxy)triphenylene;
6-acetamido-8-benzyloxy-2,3,3aS*,3bS*,4,5,6R*,7,7aR*,11bR*-decahydro-10-(5-phenyl-2-pentyloxy)-1H-cyclopenta[1]phenanthrene;
6-acetamido-8-benzyloxy-2,3,3aS,3bS,4,5,6R,7,7aR,11bR-decahydro-10-(6-phenyl-2R-hexyloxy)-1H,2H-cyclopenta[1]phenanthrene; and
6-acetamido-8-benzyloxy-2,3,3aS,3bS,4,5,6R,7,7aR,11bR-decahydro-10-(3-ethyl-1-pentyl)-1H-cyclopenta[1]phenanthrene.

EXAMPLE 114

By the procedure of Example 39, the compounds of the preceding Example are hydrogenolyzed to produce:
7-acetamido-1,2,3,4,4aS*,4bS*,5,6,7R*,8,8aR*, 12bR*-dodecahydro-9-hydroxy-11-(5-phenyl-2-pentyloxy)triphenylene (two racemates);
6-acetamido-2,3,3aS*,3bS*,4,5,6R*,7,7aR*,11bR*-decahydro-8-hydroxy-10-(5-phenyl-2-pentyloxy)-1H-cyclopenta[1]phenanthrene (two racemates);
6-acetamido-2,3,3aS,3bS,4,5,6R,7,7aR,11bR-decahydro-8-hydroxy-10-(6-phenyl-2R-hexyloxy)-1H-cyclopenta[1]phenanthrene; and
6-acetamido-2,3,3aS,3bS,4,5,6R,7,7aR,11bR-decahydro-8-hydroxy-10-(3-ethyl-1-pentyl)-1H-cyclopenta[1]phenanthrene.

EXAMPLE 115

By the procedure of Example 89, substituting succinic anhydride for acetic anhydride, the compounds of the preceding Example are converted to:
7-acetamido-9-(3-carboxypropionyloxy)-1,2,3,4,4aS*,4bS*,5,6,7R*,8,8aR*,12bR*-dodecahydro-11-(5-phenyl-2-pentyloxy)triphenylene (two racemates);
6-acetamido-8-(3-carboxypropionyloxy)-2,3,3aS*,3bS*,4,5,6R*,7,7aR*,11bR*-decahydro-10-(5-phenyl-2-pentyloxy)-1H-cyclopenta[1]phenanthrene (two racemates);
6-acetamido-8-(3-carboxypropionyloxy)-2,3,3aS,3bS,4,5,6R,7,7aR,11bR-decahydro-10-(6-phenyl-2R-hexyloxy)-1H-cyclopenta[1]phenanthrene; and
6-acetamido-8-(3-carboxypropionyloxy)-2,3,3aS,3bS,4,5,6R,7,7aR,11bR-decahydro-10-(3-ethyl-1-pentyl)-1H-cyclopenta[1]phenanthrene.

EXAMPLE 116

By the procedure of Example 89, substituting diethylaminoacetyl chloride hydrochloride for acetic anhydride, the compounds of Example 114 are converted to:
7-acetamido-9-(2-diethylaminoacetoxy)-1,2,3,4,4aS*,4bS*,5,6,7R*,8,8aR*,12bR*-dodecahydro-11-(5-phenyl-2-pentyloxy)triphenylene (two racemates);
6-acetamido-8-(2-diethylaminoacetoxy)-2,3,3aS*,3bS*,4,5,6R*,7,7aR*,11bR*-decahydro-10-(5-phenyl-2-pentyloxy)-1H-cyclopenta[1]phenanthrene (two racemates);
6-acetamido-8-(2-diethylaminoacetoxy)-2,3,3aS,3bS,4,5,6R,7,7aR,11bR-decahydro-10-(6-phenyl-2R-hexyloxy)-1H-cyclopenta[1]phenanthrene; and
6-acetamido-8-(2-diethylaminoacetoxy)-2,3,3aS,3bS,4,5,6R,7,7aR,11bR-decahydro-10-(3-ethyl-1-pentyl)-1H-cyclopenta[1]phenanthrene.

PREPARATION 1

5-Phenyl-2-pentyl Mesylate

To a stirred solution of 5-phenyl-2-pentanol (482 g.; 2.94 moles) in tetrahydrofuran (2250 ml.) at 0° C. was added methanesulfonyl chloride (300 ml.) at such a rate that the internal temperature does not rise above 10° C. (total addition time 4.5 hours). After addition is complete, the reaction mixture was allowed to warm to room temperature and stirring was continued for an additional hour. The reaction mixture was filtered and the supernate concentrated to a light yellow oil (2800 g.) which was dissolved in chloroform (2 liters) and washed with water (4×1 liter), brine (1×1 liter), charcoal treated (50 g.), dried (MgSO4), filtered through diatomaceous earth and concentrated to a light orange oil (687 g., 95% yield). This material was suitable for use without further purification.

$^1$H—NMR (CDCl$_3$): 7.23 (s, 5H, aromatic), 4.53–5.13 (m, 1H, —CH—O—), 2.93 (s, 3H, O—SO$_2$—CH$_3$), 2.42–2.93 (m, 2H, —CH$_2$C$_6$H$_5$), 1.50–1.92 [m, 4H, —(CH$_2$)$_2$—], 1.23 (s, 3H, O—CH—CH$_3$) ppm.

PREPARATION 2

5-Phenyl-2R-pentyl Mesylate

By the method of Preparation 1, 5-phenyl-2R-pentanol is converted to title product.

PREPARATION 3

5-Phenyl-2S-pentyl Mesylate

By the method of Preparation 1, 5-phenyl-2S-pentanol was converted to title product.

Likewise, 4-phenyl-2S-butanol and 6-phenyl-2S-hexanol are converted to the corresponding mesylates.

PREPARATION 4

4-Phenyl-1-butyl Mesylate

By the method of Preparation 1, 4-phenyl-1-butanol was converted to title product, a yellow oil; m/e 228; $^1$H—NMR (CDCl$_3$): 7.22 (bs, 5H, aromatic), 4.08–4.34 (m, 2H, —CH$_2$—O—), 3.93 (s, 3H, SO$_2$CH$_3$), 2.40–2.82

(m, 2H, CH$_2$C$_6$H$_5$), 1.51-1.93 (m, 4H, —CH$_2$CH$_2$—) ppm.

PREPARATION 5 d(+)-2-Octyl mesylate and l(—)-2-Octyl mesylate

By the method of Preparation 1, the optically active forms of 2-octanol were converted to:

l(—)-2-octyl mesylate, a colorless oil, [alpha]$_D^{25}$=—9.695° (CHCl$_3$,C=2.6), $^1$H—NMR (CDCl$_3$): 4.79 (bg, 1H, —CH—O—), 2.97 (s, 3H, S—CH$_3$), 1.40 (d, 3H, CH$_3$—CH), 0.87 (t, 3H, CH$_3$CH$_2$), 1.0-2.0 [m, 10H, —(CH$_2$)$_5$—] ppm; and d(+)-2-octyl mesylate, [alpha]$_D^{25}$=+9.238° (CHCl$_3$, C=2.8), $^1$H—NMR identical to the l(—) form.

PREPARATION 6

By the method of Preparation 1, the following mesylates are prepared from the corresponding alcohols:
2-phenyl-1-butyl mesylate;
3-phenyl-1-butyl mesylate;
1-phenyl-2-butyl mesylate;
4-phenyl-2-butyl mesylate;
5-phenyl-1-pentyl mesylate;
3-(3-pyridyl)-1-propyl mesylate;
1-tridecanyl mesylate;
1-dodecyl mesylate;
2-decyl mesylate;
4-decyl mesylate;
3-octyl mesylate;
4-heptyl mesylate;
5-methyl-2-hexyl mesylate;
4-methyl-1-pentyl mesylate;
1-(3-chlorophenyl)-1-butyl mesylate; and
1-(3-fluorophenyl)-1-propyl mesylate.

PREPARATION 7

Ethyl 2-(2-Phenylethyl)acetoacetate

Ethyl acetoacetate (53.8 g., 0.29 mole) was dissolved in 110 ml. of anhydrous ethanol. Sodium methoxide (17.3 g., 0.36 mole) was added portionwise to the stirred solution, allowing the temperature to rise to 40°-50°. The mixture was then heated to reflux (80°-82°) and phenethyl bromide (53.8 g., 0.32 mole) added dropwise over 1 hour. Reflux was continued for 20 hours. The reaction mixture was cooled to 30°-35° and filtered over diatomaceous earth with ethanol wash. The combined filtrate and wash were concentrated in vacuo to a pot temperature of 50°, cooled to 25°, diluted with 150 ml. of hexane and 40 ml. of water, acidified to pH 6.5-7.0 with 6N HCl. The hexane layer was separated and washed with 25 ml. of fresh water. The aqueous layers were combined and back-washed with 40 ml. of fresh hexane. The hexane layers were combined, washed with 60 ml. of water, dried over 15 g. MgSO$_4$, filtered and evaporated to yield title product as an oil (62 g., 91%).

PREPARATION 8

5-Phenyl-2-pentanone

Product of the preceding Preparation (30.5 g., 0.13 mole) was combined with 130 ml. of ethanol, 25 ml. of water and KOH (85%, 20.6 g., 0.31 mole). The reaction mixture was refluxed for 3 hours, cooled, concentrated in vacuo to 80 ml., and diluted with 90 ml. of water and 60 ml. of hexane. The water layer was separated and washed with 40 ml. of fresh hexane. The combined organic layers were back-washed with 30 ml. of water, dried (MgSO$_4$), filtered and stripped of solvent to yield 12.8 g. of crude product as an oil, purified by distillation (9.5 g., b.p. 104°/2 mm.).

PREPARATION 9

5-Phenyl-2-pentanol

Under nitrogen, sodium borohydride (755 mg., 0.02 mole) was dissolved in 30 ml. of absolute ethanol and cooled to 0-5°. Ketone of the preceding Preparation (10.3 g., 0.064 mole) was added dropwise with stirring over 30 minutes, maintaining the temperature 5-15°. The temperature was increased to 22° for 2 hours, and then reduced to 10-12° as 3 ml. of methanol was added over 5 minutes and 2 ml. of concentrated HCl was added over 30 minutes. The quenched reaction mixture was poured into 20 ml. of water and extracted with hexane (50 ml.). The extract was dried (MgSO$_4$), filtered, concentrated to an oil and distilled to yield title product (8.7 g., 83%, b.p. 90-100°/0.3 mm.).

PREPARATION 10

5-Phenyl-2-pentyl Hydrogen Phthalate

Phthalic anhydride (21.5 g., 0.145 mole) was stirred with the alcohol of the preceding Preparation (23.7 g., 0.145 mole) and heated to 90°. The temperature is gradually increased to 130°, an exotherm occuring at some point above 90°. The temperature, when the exotherm occurs is not allowed to rise above 155°. Following the exotherm, the reaction is maintained at 130-140° for 1 hour, then cooled to 50° and diluted with 125 ml. of acetonitrile. The resulting solution of title product is used directly in the next step.

PREPARATION 11

5-Phenyl-2S-pentyl Brucine Phthalate

Brucine (57.6 g., 0.146 mole) in 105 ml. of acetonitrile was added to the acetonitrile solution of ester from the preceding Preparation and the mixture heated to 55-60°. Maintaining this temperature, isopropyl ether (610 ml.) is added in a steady stream. The solution is cooled gradually to 23°, and the crystalline material which begins to form at 45-55°, granulated for 16 hours, recovered by filtration and air dried at 55° (33 g.). Highly resolved material has [alpha]$_D^{CHC_3}$ +40.0. If at this stage the rotation is less than +38.5°, it is recrystallized from acetonitrile-isopropyl ether (for 33 g. of crude, 130 ml. of acetonitrile and 300 ml. of isopropyl ether was used, with recovery of 26 g. of purified title product).

PREPARATION 12

5-Phenyl-2S-pentanol

S-Brucine salt of the preceding Preparation (10.0 g., 14.2 mmoles) was combined with 125 ml. of toluene and 150 ml. of water. With stirring the pH was adjusted to 1.7 with about 6 ml. of 3N HCl. The aqueous layer was separated and extracted 2×40 ml. toluene. Brucine was precipitated from the aqueous layer by adjusting the pH to 11.5 with 50% NaOH. Recrystallization from isopropyl alcohol provides material suitable for reuse. The toluene layers were combined, back-washed with 75 ml. of water, concentrated to 45-50 ml. Fresh water (65 ml.) and then KOH (85%, 1.90 g., 28.8 mmoles) were added and the mixture stirred for 1 hour at room temperature and then 2 hours at 82–84°. The reaction mixture was cooled to 25°, the toluene layer separated and the aqueous layer washed 3×20 ml. toluene. The toluene layers were combined, washed 1×20 ml. saturated NaCl, dried (MgSO$_4$), filtered and concentrated to yield title product as an oil (1.91 g.), purified by distillation in vacuo (1.64 g., b.p. 85–92°/0.1 mm., [alpha]$_D^{25}$+8.24 to +8.57°).

PREPARATION 13

5-Phenyl-2R-pentanol

To a solution of racemic 5-phenylpentan-2-ol (4.9 g., 0.03 mole) in 50 ml. toluene was added d-mandelic acid (4.5 g., 0.03 mole) and a trace of p-toluenesulfonic acid. This mixture was heated for 10 hours at reflux using a Dean Stark device to remove water. Upon cooling, 50 ml. of benzene was added and the reaction washed with 3×100 ml. of saturated NaHCO$_3$ solution, the organic phase dried (MgSO$_4$) and concentrated to yield 7.0 g. of a colorless oil (78%). A portion of this oil (5.4 g.) was subjected to column chromatographic separation using 500 g. of silica gel and an ethyl ether-hexane (1 to 4) solvent system. The separation of the diastereomeric mandelates could conveniently be followed by $^1$H—NMR. The first eluting 5-phenyl-2R-pentanol had the CH$_3$ doublet (J=7.0) centered at 1.05 ppm and the second eluting 5-phenyl-2S-pentanol at 1.25 ppm. Using a fraction collector, 150 15 ml. fractions were collected from the above column. Fractions 101–110 show an isomer ratio of ca. 95:5 of the first eluting isomer (HPLC). These fractions were combined and concentrated to yield 0.90 g.; [alpha]$_D^{25}$=37.56° (CHCl$_3$).

A portion of the purified first eluting isomer (0.80 g., 0.0027 mole) was dissolved in 25 ml. of methanol and 2.0 ml. of H$_2$O and 0.50 g. of K$_2$CO$_3$ (0.0036 mole) was added and this reaction stirred for 24 hours at 25°. Water (10 ml.) was then added and the reaction extracted with 2×25 ml. of EtOAc; the organic layers combined, dried (MgSO$_4$) and concentrated to yield 0.40 g. (90%) of 5-phenylpentan-2-ol, [alpha]$_D^{25}$=−7.16° (CHCl$_3$).

PREPARATION 14

5-Phenyl-2S-pentanol

A sample of 9.9 g. (0.043 mole) of S(+)-propylene glycol 1-tosylate prepared from L-ethyl lactate according to Gombos et al., Chem. Ber. 109, p. 2145 (1976), was dissolved in 20 ml. of dry THF. This solution was added dropwise over 15 minutes to a rapidly stirred mixture of 98 ml. of 1.1M phenethyl magnesium bromide in THF (0.11 mole), immediately after 1.05 g. of cuprous chloride was added in one portion to the Grignard. The temperature of the initial cuprous chloride addition and of the subject tosylate addition was maintained at 18–25° (upon the addition of the CuCl$_2$, the Grignard solution turned a deep purple). The reaction was then stirred for 1 hour at 25°, and quenched into 30 ml. of saturated NH$_4$Cl solution. The aqueous phase was separated and extracted 2x with 100 ml. portions of ethyl ether. The combined organic layer and washings were washed with brine (2×100 ml.), dried (MgSO$_4$) and concentrated to give 10.98 g. of crude title product as an oil. The pure S(+)-5-phenylpentan-2-ol was obtained by fractional high vacuum distillation. The purified S(+)-5-phenylpentan-2-ol had [alpha]$_D^{25}$=+7.94 (CHCl$_3$).

Other appropriate Grignard reagents are substituted for phenylethyl magnesium bromide to prepare a wide variety of other optically active alcohols useful in the present invention. Exemplary are:
4-phenyl-2S-butanol;
6-phenyl-2S-hexanol; and
2S-octanol.

PREPARATION 15

3-Bromo-5-(2-undecyl)anisole

3-Amino-5-(2-undecyl)anisole, prepared according to methods set forth by Johnson, U.S. Pat. No. 4,260,764 is diazotized and converted to the title compound according to procedures set forth by Bigelow, Org. Syntheses, Coll. Vol. I, pp. 135–137 (1941).

In the same manner, other aminoanisoles, also prepared by methods set forth by Johnson, are converted to:
3-bromo-5-(2-hexyl)anisole;
3-bromo-5-(3-ethyl-1-pentyl)anisole;
3-bromo-5-(5-phenyl-1-hexyl)anisole;
3-bromo-5-(6-phenyl-2-hexyl)anisole;
3-bromo-5-(6-phenyl-3-hexyl)anisole;
3-bromo-5-[6-(4-chlorophenyl)-2-hexyl]anisole;
3-bromo-5-[5-(4-fluorophenyl)-2-pentyl]anisole;
3-bromo-5-[6-(4-pyridyl)-2-hexyl]anisole;
3-bromo-5-[1-(1-heptyloxy)-2-propyl]anisole; and
3-bromo-5-[2-(2-phenylethoxy)-1-propyl]anisole.

PREPARATION 16

3-Methoxy-5-(2-undecyl)benzonitrile

3-Amino-5-(2-undecyl)anisole is diazotized and reacted with cuprous cyanide according to procedures set forth by Clarke and Read, Org. Syntheses, Coll. Vol. I, pp. 514–516 (1941) to produce the title product.

In the same manner other appropriate aminophenols are converted to:
3-methoxy-5-(5-phenyl-2-methyl-1-pentyl)benzonitrile;
3-methoxy-5-[5-(2-chlorophenyl)-1-hexyl]benzonitrile;
3-methoxy-5-[7-(3-fluorophenyl)-3-heptyl]benzonitrile; and
3-methoxy-5-[8-(3-pyridyl)-1-octyl]benzonitrile.

PREPARATION 17

3-Methoxy-5-(2-undecyl)benzoic Acid

Using the method of Example 92, the title nitrile of the preceding Preparation is hydrolyzed to the title acid.

By the same method, the other nitriles of the preceding Preparation are converted to:
3-methoxy-5-(5-phenyl-2-methyl-1-pentyl)benzoic acid;
3-methoxy-5-[5-(2-chlorophenyl)-1-hexyl]benzoic acid;
3-methoxy-5-[7-(3-fluorophenyl)-3-heptyl]benzoic acid; and
3-methoxy-5-[8-(3-pyridyl)-1-octyl]benzoic acid.

If desired, the 3-methoxy-5-(2-undecyl)benzoic acid is resolved into its enantiomeric forms via salt formation with an optically active base, as set forth by Feiser and Fieser, Reagents for Organic Syntheses, John Wiley and Sons, 1967, pp. 977–978, thus affording:
3-methoxy-5-(2S-undecyl)benzoic acid; and
3-methoxy-5-(2R-undecyl)benzoic acid.

In like manner, 3-methoxy-5-(5-phenyl-2-methyl-1-pentyl)benzoic acid is resolved to yield:
3-methoxy-5-(5-phenyl-2S-methyl-1-pentyl)benzoic acid; and 3-methoxy-5-(5-phenyl-2R-methyl-1-pentyl)benzoic acid.

PREPARATION 18

3-Methoxy-5-(2-undecyl)benzoyl Chloride

The title acid of the preceding Preparation is reacted with excess thionyl chloride in methylene chloride diluent in the presence of a trace of dimethylformamide. After refluxing for 3 hours the acid chloride is recovered by evaporation of the solvent and excess thionyl chloride chased with toluene.

By the same method, the other acids of the preceding Preparation are converted to:
3-methoxy-5-(5-phenyl-2-methyl-1-pentyl)benzoyl chloride;
3-methoxy-5-[5-(2-chlorophenyl)-1-hexyl]benzoyl chloride;
3-methoxy-5-[7-(3-fluorophenyl)-3-heptyl]benzoyl chloride;
3-methoxy-5-[8-(3-pyridyl)-1-octyl]benzoyl chloride;
3-methoxy-5-(2S-undecyl)benzoyl chloride;
3-methoxy-5-(2R-undecyl)benzoyl chloride;
3-methoxy-5-(5-phenyl-2S-methyl-1-pentyl)benzoyl chloride; and
3-methoxy-5-(5-phenyl-2R-methyl-1-pentyl)benzoyl chloride.

PREPARATION 19

3-Methoxy-5-(2-undecyl)benzaldehyde

Method A

The title acid chloride of the preceding Preparation is subjected to hydrogenation under Rosenmund conditions, as set forth by Mosettig and Mozingo in Organic Reactions, Vol. 4, John Wiley and Sons, New York, 1948, pp. 362–377, producing the title product.

Method B

The title nitrile of Preparation 16 is subjected to the Stephen reduction under conditions set forth by Williams, Org. Syntheses, Coll. Vol. III, pp. 626–627 (1955).

Method C

The title acid chloride of the preceding Preparation is reacted with excess ethyl mercaptan to yield the corresponding thiol ester. Hydrogenolysis to the title aldehyde is effected by refluxing the thiol ester with Raney nickel in ethanol under conditions set forth by Wolfrom and Karbinos, J. Am. Chem. Soc. 68, pp. 1455–1456 (1946).

Method D

3-Methoxy-5-(2-undecyl)benzyl bromide is oxidized according to methods set forth by Kornblum et al., J. Am. Chem. Soc. 81, pp. 4113–4114 (1959). The required benzyl bromide is prepared according to methods set forth by Althuis et al., U.S. Pat. No. 4,188,495.

Method E

3-Bromo-5-(2-undecyl)anisole is reacted with magnesium in ether to form the corresponding Grignard reagent, then reacted with ethyl orthoformate and hydrolyzed to title product according to procedures set forth by Smith and Nichols, J. Org. Chem. 6, pp. 489–506 (1941).

By methods A–D, the appropriate acid chlorides, nitriles or bromomethyl compounds are converted to:
3-methoxy-5-(5-phenyl-2-methyl-1-pentyl)benzaldehyde;
3-methoxy-5-[5-(2-chlorophenyl)-1-hexyl]benzaldehyde;
3-methoxy-5-[7-(3-fluorophenyl)-3-heptyl]benzaldehyde;
3-methoxy-5-[8-(3-pyridyl)-1-octyl]benzaldehyde;
3-methoxy-5-(2S-undecyl)benzaldehyde;
3-methoxy-5-(2R-undecyl)benzaldehyde;
3-methoxy-5-(5-phenyl-2S-methyl-1-pentyl)benzaldehyde; and
3-methoxy-5-(5-phenyl-2R-methyl-1-pentyl)benzaldehyde.

By method E, aryl bromides from an earlier Preparation are converted to:
3-hydroxy-5-(2-hexyl)benzaldehyde;
3-hydroxy-5-(3-ethyl-1-pentyl)benzaldehyde;
3-hydroxy-5-(5-phenyl-1-hexyl)benzaldehyde;
3-hydroxy-5-(6-phenyl-2-hexyl)benzaldehyde;
3-hydroxy-5-[6-(4-chlorophenyl)-2-hexyl]benzaldehyde;
3-hydroxy-5-[6-(4-fluorophenyl)-2-pentyl]benzaldehyde;
3-hydroxy-5-[6-(4-pyridyl)-2-hexyl]benzaldehyde;
3-hydroxy-5-[1-(1-heptyloxy)-2-propyl]benzaldehyde; and
3-bromo-5-[2-(2-phenylethoxy)-1-propyl]benzaldehyde.

PREPARATION 20

Benzyl Methanesulfonate

Under nitrogen methylene chloride (1.4 liter), benzyl alcohol (129.6 g., 1.2 moles) and triethylamine (182 g., 1.8 moles) were combined, stirred and cooled to $-5°$ C. in an ice-water-acetone bath. A solution of methanesulfonyl chloride (150 g., 1.31 moles) in 100 ml. of methylene chloride was added over 49 minutes, maintaining the temperature between $-5°$ and $2°$ C. After stirring for 10 minutes at $0°-2°$ C., the reaction was diluted with 500 ml. of water, precooled to $5°$ C. The organic layer was separated, washed $2\times500$ ml. of cold water, dried over $MgSO_4$, filtered and evaporated in vacuo to yield title product as a light yellow oil [190 g.; 85%; $^1$H—NMR ($CDCl_3$) delta (ppm): 2.9 (s, 3H), 5.2 (s, 2H), 7.4 (m, 5H); $R_f$ 0.75 ($CH_2Cl_2$)]. This product was refrigerated until used in the next step.

PREPARATION 21

Ethyl 2S-Benzyloxypropionate

Under nitrogen, benzyl methanesulfonate (181.5 g., 0.975 mole) was combined and stirred with S ethyl lactate (ethyl 2S-hydroxypropionate; 393 g., 3.33 moles) and the resulting solution heated on a steam bath to $94°$ C. over 15 minutes and held for 1.5 hours at this temperature. The reaction mixture was cooled to $45°$ C., poured into 2 liters of cold toluene. Water (500 ml.) was added and the mixture stirred for 5 minutes. The aqueous phase was separated and extracted with 200 ml. fresh toluene. The organic layers were combined, washed in sequence $2\times500$ ml. $H_2O$, $1\times500$ ml. saturated $NaHCO_3$, $2\times500$ ml. water and $1\times500$ ml. saturated NaCl, dried over $MgSO_4$, filtered, and evaporated in vacuo to yield crude product as an oil [228 g., 112% $[alpha]_D^{25} -60.8°$, C=1.11 ($CHCl_3$)], which $^1$H—NMR indicated to be contaminated with ethyl lactate. Distillation in vacuo gave, after an early boiling solvent fraction 1 [25 ml., b.p. to 79° C./1.2 mm.; [alpha]$_d$−6.9°, C=1.13 (CHCl$_3$)]; fractions 2-8 [74 ml., b.p. 82° C./1.3 mm to 114° C./3 mm.; [alpha]$_D$−42.1° to −76.2°, C=1.09-1.16 (CHCl$_3$)] as a mixture of S ethyl lactate and title product; and fractions 9-12 [57 ml.; b.p. 115° C./3 mm., 98°-100°/0.75 mm., 102°-106° C./1.0 mm.; [alpha]$_D$−80.0° to −83.7°, C=1.01-1.17 (CHCl$_3$)] of substantially pure title product. A higher boiling pot residue of 49 g. remained. A portion of fraction 10 (3 g.) was voided of traces of ethyl lactate by taking up in 100 ml. of hexane and equilibrating with 30 ml. H$_2$O. The hexane layer was separated, washed 3×30 ml. H$_2$O, dried over MgSO$_4$, filtered and concentrated to an oil [2.4 g.; R$_f$ 0.32 (6:1 hexane:ethyl acetate); [alpha]$_D^{25}$−83.3°, C=1.13 (CHCl$_3$)].

PREPARATION 22

2S-Benzyloxy-1-propanol

Fractions 2-9 and 12 from the above distillation (106.1 g. total weight, 0.45 moles of ethyl 2S-benzyloxypropionate and 0.25 moles of S ethyl lactate) was dissolved in 100 ml. of anhydrous ethanol and the solution added dropwise to a stirred mixture of NaBH$_4$ (37.85 g., 1.0 mole) and 500 ml. of anhydrous ethanol under nitrogen over a one hour period. The temperature was maintained at 25°-30° C. during addition by cooling with a 20° C. ater bath. After stirring for 20 hours at ambient temperature, the reaction mixture was cooled to 10° C. and 95 ml. of 12N HCl (1.14 mole) added dropwise over 15 minutes under a sweep of nitrogen. The resulting slurry was filtered with 100 ml. ethanol wash. The filtrate and wash were combined and concentrated in vacuo to 150 ml. The concentrate was diluted with 200 ml. of water and 300 ml. of ethyl acetate, the pH was adjusted from 1.5 to 9.0 with 50 ml. of 4N NaOH (causing precipitated solids to dissolve) and the layers were separated. The aqueous phase was washed 1×100 ml. and then 1×50 ml. of ethyl acetate. The three organic layers were combined, washed 2×150 ml. H$_2$O and then 1×150 ml. saturated NaCl, dried over MgSO$_4$, filtered, and evaporated to yield title product as an oil [50.5 g.; [alpha]$_D^{25}$+47.9, C=1.08 (CHCl$_3$); +27.736 (neat); R$_f$ 0.1 (CH$_2$Cl$_2$)].

PREPARATION 23

2S-Benzyloxy-1-propyl Mesylate

Under nitrogen, 2S-benzyloxy-1-propanol (49.8 g., 0.3 mole), 400 ml. of CH$_2$Cl$_2$ and triethylamine (40.5 g., 0.4 mole) were combined, stirred and cooled to −5° C. in an ice-water-acetone bath. Maintaining −5° C., methanesulfonyl chloride (37.8 g., 0.33 mole) in 30 ml. CH$_2$Cl$_2$ was added over one hour. After stirring at −5° C. for 0.5 hour, H$_2$O (200 ml. at 5° C.) was added. The layers were separated and the aqueous layer washed 1×100 ml. CH$_2$Cl$_2$. The combined organic layers were washed in sequence 1×100 ml. H$_2$O, 1×100 ml. 1N HCl, 1×100 ml. H$_2$O, 1×100 ml. saturated NaHCO$_3$ and 1×100 ml. H$_2$O, dried over MgSO$_4$, filtered, and concentrated in vacuo to yield title product as an oil [72.2 g., 98.5%; [alpha]$_D^{25}$+7.7, C=1.00 (CHCl$_3$); R$_f$ 0.6 (CH$_2$Cl$_2$)].

PREPARATION 24

2S-Benzyloxy-1-propyl Iodide

Under nitrogen with stirring, sodium iodide (90 g., 0.6 mole) was dissolved in one liter dry acetone. At 32° C., 2S-benzyloxy-1-propyl mesylate (71.5 g., 0.293 mole) was added. The reaction mixture was warmed to 59°-60° C. (gentle reflux) and held for 20 hours, at which time tlc indicated about 20% starting material to remain. Additional sodium iodide (30 g., 0.2 mole) was added and refluxing continued for 3 hours. The reaction was cooled to room temperature and filtered with acetone wash. The combined filtrate and wash was concentrated to 150 ml. of oily solids, diluted with 300 ml. toluene and 200 ml. H$_2$O, the layers separated and the aqueous phase extracted 2×100 ml. toluene. The three organic layers were combined, washed 2×200 ml. H$_2$O, dried over MgSO$_4$, filtered and evaporated to yield title product as an oil [79 g., 96%; [alpha]$_D$=+8.0°, C=1.08 (CHCl$_3$), $^1$H—NMR (CDCl$_3$) delta (ppm): 1.4 (d, 3H), 3-3.6 (m, 3H), 4.6 (s, 2H), 7.35 (s, 5H)].

PREPARATION 25

Ethyl 2-Benzoyl-4S-benzyloxyvalerate

Under nitrogen, sodium hydride (50% in oil, 13.6 g., 0.283 mole) was washed with 3×200 ml. of dry hexane. To the resulting hexane wet NaH, 130 ml. dimethylformamide was added, followed by the dropwise addition of ethyl benzoylacetate (54.4 g., 0.283 mole) over 45 minutes, maintaining the temperature 28°-32° C. with a 10° C. water bath and sweeping away evolved H$_2$ with N$_2$. After stirring for 85 minutes at 25° C., 2S-benzyloxy-1-propyl iodide (78 g., 0.283 mole) was added with 40 ml. of dimethylformamide for rinse. The reaction mixture was then heated and stirred at 122°-126° C. for 2 hours (during which solids precipitated), cooled to 70° C., diluted with 350 ml. toluene and 560 ml. of ice water, and the resulting layers separated. The aqueous layer was extracted 3×150 ml. toluene. The four organic layers were combined, washed 3×150 ml. H$_2$O and then 1×150 ml. saturated NaCl, dried over MgSO$_4$, filtered and concentrated in vacuo to yield title product as an oil (90 g., 94%; [alpha]$_D^{25}$+15.8°, C=1.12 (CHCl$_3$); R$_f$ 0.35 (6:1 hexane:ethyl acetate)].

Substitution of an equivalent amount of S-propylene oxide for 2S-benzyl-1-propyl iodide in this process and operating in a closed container (i.e. under pressure) to avoid loss of the volatile epoxide affords a method for the preparation of ethyl 2-benzoyl-4S-hydroxyvalerate.

PREPARATION 26

4S-Benzyloxy-1-phenyl-1-pentanone

Ethyl 2-benzoyl-4S-benzyloxyvalerate (89 g., 0.26 mole), ethanol (175 ml.), water (175 ml.) and KOH (85%, 51 g., 0.8 mole) were combined with stirring under nitrogen, during which the temperature rose to 45° C. The reaction mixture was heated to 79° C. under a reflux condenser and held for 18 hours. The reaction mixture was cooled to 25° C., diluted with 350 ml. of water and 300 ml. of toluene, the layers separated, and the aqueous layer washed 1×200 ml. and 2×150 ml. toluene. The organic layers were combined, washed 2×200 ml. H$_2$O and 1×200 ml. saturated NaCl, dried over MgSO$_4$, filtered and concentrated in vacuo to yield title product as an oil [45.5 g., 65%; [alpha]$_D^{25}$+21.92°, C=1.20 (CHCl$_3$); R$_f$ 0.55 (6:1 hexane:ethyl acetate)].

The same method is used to convert ethyl 2-benzoyl-4S-hydroxyvalerate to 4S-hydroxy-1-phenyl-1-pentanone.

PREPARATION 27

5-Phenyl-2S-pentanol

4S-Benzyloxy-1-phenyl-1-pentanone (45 g., 0.168 mole) in 150 ml. of toluene, 15 ml. of absolute alcohol and 3 drops concentrated HCl were hydrogenated over 4 g. 50% water wet 5% Pd/C at 50-60 psig and 25° C. After hydrogenating for 6 hours, an additional 4 g. catalyst was charged and hydrogenation continued for 2.5 hours, by which time three equivalents of hydrogen were consumed and there had been no uptake over the final 1.5 hour period. The catalyst was recovered by filtration. The filtrate was neutralized by stirring over a 5 cc volume of solid NaHCO$_3$, dried over MgSO$_4$, filtered and concentrated in vacuo to yield title product as an oil [22 g., 80%; [alpha]$_D^{25}$+8.63, C=1.02 (CHCl$_3$); R$_f$ 0.2 (6:1 hexane:ethyl acetate)]. If desired the title product was further purfied by simple distillation to remove traces of tlc origin material, b.p. 90-94/0.7 mm. with nearly quantitative recovery.

By the same procedure, with uptake of two rather than three equivalents of hydrogen, 4S-hydroxy-1-phenyl-1-pentanone is converted to 5-phenyl-2S-pentanol.

We claim:

1. A compound having the formula

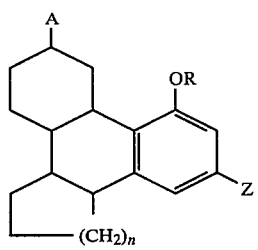

wherein
n is 1 or 2;
A is OH, (C$_1$-C$_5$)alkanoyloxy, (C$_1$-C$_5$)alkanoylamino or (C$_1$-C$_4$)alkanesulfonamido;
R is H, benzoyl, (C$_1$-C$_5$)alkanoyl or —CO(CH$_2$)$_m$Y, wherein m is 1, 2, 3 or 4, Y is —COOH, or -NR'R", R' and R" when taken separately are each independently H or (C$_1$-C$_4$)alkyl, and R' and R" when taken together with the nitrogen to which they are attached are piperidino, pyrrolo, pyrrolidino, morpholino or N-[(C$_1$-C$_4$)alkyl]piperazino; and
Z is (C$_5$-C$_{13}$)alkyl, (C$_5$-C$_{13}$)alkoxy, (C$_5$-C$_{13}$)-alkoxyalkyl, (C$_8$-C$_{13}$)pyridylalkyl, (C$_8$-C$_{13}$)pyridylalkoxy, (C$_8$-C$_{13}$)pyridyloxyalkyl, (C$_8$-C$_{13}$)pyridylalkoxyalkyl, (C$_9$-C$_{14}$)phenylalkyl, (C$_9$-C$_{14}$)-phenylalkoxy, (C$_9$-C$_{14}$)phenoxyalkyl, or (C$_9$-C$_{14}$)phenylalkoxyalkyl, wherein said phenyl groups are optionally substituted with a chloro or a fluoro;
a pharmaceutically-acceptable acid addition salt thereof when R is —CO(CH$_2$)$_m$Y and Y is —NR'R"; or
a pharmaceutically-acceptable cationic salt thereof when R is —CO(CH$_2$)$_m$Y and Y is —COOH.

2. A compound of claim 1 having the absolute or relative stereochemical formula

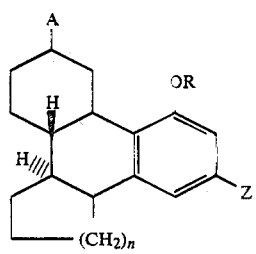

3. A compound of claim 2 having the absolute or relative stereochemical formula

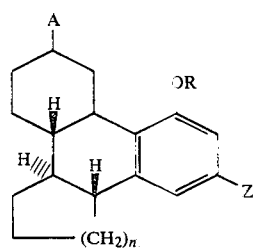

4. A compound of claim 3 having the absolute or relative stereochemical formula

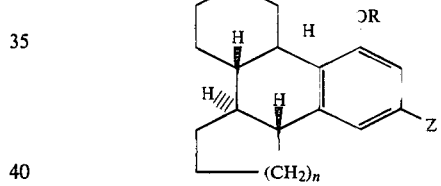

5. A compound of claim 4 having the absolute or relative stereochemical formula

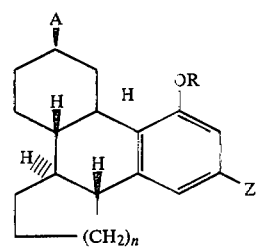

6. A compound of any one of claims 1, 2, 3, 4 or 5 wherein Z is 5-phenyl-2-pentyloxy.

7. A compound of claim 6 wherein A is hydroxy and R is acetyl.

8. A compound of claim 7 wherein Z is 5-phenyl-2R-pentyloxy.

9. A compound of claim 8 wherein n is 2.

* * * * *